(12) United States Patent
Frey et al.

(10) Patent No.: US 7,456,271 B2
(45) Date of Patent: Nov. 25, 2008

(54) GLUTAMATE 2,3-AMINOMUTASES AND METHODS OF USE THEREOF

(75) Inventors: Perry A. Frey, Madison, WI (US); Frank J. Ruzicka, Lodi, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/546,029

(22) Filed: Oct. 11, 2006

(65) Prior Publication Data

US 2007/0092952 A1 Apr. 26, 2007

Related U.S. Application Data

(60) Provisional application No. 60/725,350, filed on Oct. 11, 2005.

(51) Int. Cl.
*C07H 21/04* (2006.01)
(52) U.S. Cl. .................. 536/23.2; 435/69.1; 435/183; 435/233; 435/252.3
(58) Field of Classification Search ........................ None
See application file for complete search history.

(56) References Cited

U.S. PATENT DOCUMENTS

| 4,036,945 | A | 7/1977 | Haber |
| 4,331,647 | A | 5/1982 | Goldenberg |
| 4,946,778 | A | 8/1990 | Ladner et al. |
| 6,248,874 | B1 | 6/2001 | Frey et al. |
| 2002/0173637 | A1 | 11/2002 | Frey et al. |
| 2003/0113882 | A1 | 6/2003 | Frey et al. |

OTHER PUBLICATIONS

Ballinger, M.D., Frey, P.A. and Reed, G.A. (1995) Biochemistry 34, 1008610093.
Ballinger, M.D., Frey, P.A. and Reed, G.A. (1992) Biochemistry 31, 10782-10789.
Cardillo and Tomasini, Chem. Soc. Rev. 25:77 (1996).
Frey and Reed, Adv. Enzymol. 66:1 (1993).
Moss, M. and Frey, P.A. (1987) J. Biol.Chem. 262, 14859-14862.
Petrovich, R.M., Ruzicka, F.J., Reed, G.H., and Frey, P.A. (1992) Biochemistry 31, 10774-10781.
International Search Report for PCT/US06/39827 dated Mar. 27, 2008.

*Primary Examiner*—Anand U Desai
(74) *Attorney, Agent, or Firm*—Foley & Lardner LLP

(57) ABSTRACT

There are provided nucleic acids, including isolated DNA molecules, which encode glutamate 2,3-aminomutase enzymes, polypeptides produced from such nucleic acids and methods of making the nucleic acids and polypeptides. There are further provided methods of producing β-glutamate from glutamate using glutamate 2,3-aminomutase.

21 Claims, 9 Drawing Sheets

SEQUENCE LISTING

```
<160> NUMBER OF SEQ ID NOS: 31

<210> SEQ ID NO 1
<211> LENGTH: 1269
<212> TYPE: DNA
<213> ORGANISM: Clostridium difficile

<400> SEQUENCE: 1
atgaatgaac aaactagaat atccttagag agagctgctg aattaaaatc aaaaattgat     60
gattatattc aggctagaaa aacgattaac agaggtcttg aaaaagaaga agagataaat    120
aaacgaaaac agaaaatatt aagtatctta aatggaactg aagaggattg gaataactac    180
aaatggcaat tatcaaatag aataacagat gtagatactt tatcaaaaat tataactcta    240
actaaaaaag aaaaagaata tataaagag gttggtactc aatttagatg ggcaatatct    300
ccatattatt tgagtcttat agaccagaa gatatatgtg acccaataaa attactgtct    360
```

-continued

```
ataccaacac atatagagtt ggaagatgaa caagaagatt tggacccaat gggagaagag      420
tatacaaacc cagcaggatg tataactaga agatacccgg atagattaat aataaatgta      480
acaaatgagt gtgctatgta ttgtagacac tgtcagagaa gaagaaatat tggacaacaa      540
gattctcata agtcaaaagc tattatccaa gaatctatag actatatcag agaaaatgaa      600
gaaataagag atgtactagt aactggtgga gatgctctta cattaaaaga tgattattta      660
gagtggattc ttagccaact taagagata ccacatgttg attatgttag attaggtact       720
aggactcttg ttacaatgcc acaagaatt acagatgaat tttgcaatat gctaaaaaaa       780
tatcacccta tatatataaa tactcatttt aatcatccaa tggaaataac taaggaatct     840
aaagaagctt gtgaaaagtt agcaaatgca ggagttccat taggaaatca ggcagtatta    900
ttaaatggaa taataatga taaatttgta atgagatgtt taaatcaaga attactgaaa      960
ataagagtaa aaccttatta tatattccaa agtaaacatg taaagggaac aaaacatttc    1020
aatacatcag tagatgatgg tcttgaaatc atggagtatt taagaggata tacatcagga    1080
atggctatac caacatatat agtaaatgct ccaaaaggag gaggaaagac tcctttgctt    1140
cctcaatacc ttgtatcaaa aggaacagat tacgttatgc ttagaacatg ggaaggaaaa    1200
gttataaaaa tggaagatga acctgctgta gatataaaga aacttataaa agaacaagca    1260
caggattaa                                                             1269
```

<210> SEQ ID NO 2
<211> LENGTH: 422
<212> TYPE: PRT
<213> ORGANISM: Clostridium difficile

<400> SEQUENCE: 2

```
Met Asn Glu Gln Thr Arg Ile Ser Leu Glu Arg Ala Ala Glu Leu Lys
  1               5                  10                  15
Ser Lys Ile Asp Asp Tyr Ile Gln Ala Arg Lys Thr Ile Asn Arg Gly
             20                  25                  30
Leu Glu Lys Glu Glu Glu Ile Asn Lys Arg Lys Gln Lys Ile Leu Ser
         35                  40                  45
Ile Leu Asn Gly Thr Glu Glu Asp Trp Asn Asn Tyr Lys Trp Gln Leu
     50                  55                  60
Ser Asn Arg Ile Thr Asp Val Asp Thr Leu Ser Lys Ile Ile Thr Leu
 65                  70                  75                  80
Thr Lys Lys Glu Lys Glu Tyr Ile Lys Glu Val Gly Thr Gln Phe Arg
                 85                  90                  95
Trp Ala Ile Ser Pro Tyr Tyr Leu Ser Leu Ile Asp Pro Glu Asp Ile
            100                 105                 110
Cys Asp Pro Ile Lys Leu Leu Ser Ile Pro Thr His Ile Glu Leu Glu
        115                 120                 125
Asp Glu Gln Glu Asp Leu Asp Pro Met Gly Glu Glu Tyr Thr Asn Pro
    130                 135                 140
Ala Gly Cys Ile Thr Arg Arg Tyr Pro Asp Arg Leu Ile Ile Asn Val
145                 150                 155                 160
Thr Asn Glu Cys Ala Met Tyr Cys Arg His Cys Gln Arg Arg Arg Asn
                165                 170                 175
Ile Gly Gln Gln Asp Ser His Lys Ser Lys Ala Ile Ile Gln Glu Ser
            180                 185                 190
Ile Asp Tyr Ile Arg Glu Asn Glu Glu Ile Arg Asp Val Leu Val Thr
        195                 200                 205
```

```
Gly Gly Asp Ala Leu Thr Leu Lys Asp Asp Tyr Leu Glu Trp Ile Leu
        210                 215                 220

Ser Gln Leu Lys Glu Ile Pro His Val Asp Tyr Val Arg Leu Gly Thr
225                 230                 235                 240

Arg Thr Leu Val Thr Met Pro Gln Arg Ile Thr Asp Glu Phe Cys Asn
                245                 250                 255

Met Leu Lys Lys Tyr His Pro Ile Tyr Ile Asn Thr His Phe Asn His
                260                 265                 270

Pro Met Glu Ile Thr Lys Glu Ser Lys Glu Ala Cys Glu Lys Leu Ala
            275                 280                 285

Asn Ala Gly Val Pro Leu Gly Asn Gln Ala Val Leu Leu Asn Gly Ile
        290                 295                 300

Asn Asn Asp Lys Phe Val Met Arg Cys Leu Asn Gln Glu Leu Leu Lys
305                 310                 315                 320

Ile Arg Val Lys Pro Tyr Tyr Ile Phe Gln Ser Lys His Val Lys Gly
                325                 330                 335

Thr Lys His Phe Asn Thr Ser Val Asp Asp Gly Leu Glu Ile Met Glu
                340                 345                 350

Tyr Leu Arg Gly Tyr Thr Ser Gly Met Ala Ile Pro Thr Tyr Ile Val
            355                 360                 365

Asn Ala Pro Lys Gly Gly Lys Thr Pro Leu Leu Pro Gln Tyr Leu
        370                 375                 380

Val Ser Lys Gly Thr Asp Tyr Val Met Leu Arg Thr Trp Glu Gly Lys
385                 390                 395                 400

Val Ile Lys Met Glu Asp Glu Pro Ala Val Asp Ile Lys Lys Leu Ile
                405                 410                 415

Lys Glu Gln Ala Gln Asp
            420

<210> SEQ ID NO 3
<211> LENGTH: 1260
<212> TYPE: DNA
<213> ORGANISM: Thermoanaerobacter tengcongensis

<400> SEQUENCE: 3
atgagcagca cgggttcact cacagtggag gaaaaaagga aaatagcact ccaaagagcg      60
gaagagttaa aaagaagat agagccatac ttgagagcat ctgaaaaaat agagacgggc     120
tttaagttat cagaaaaatt tagagaaaac aaggagaaaa ttaaaaactt atttggagca     180
acagaagagg aatggaatga ttggcgatgg cagataagaa atcgtataag tgatgttgaa     240
actctcaaaa agattgtaaa cctttctgag gaggaaattg aaaacataaa gagggtaagt     300
actcgctaca gatgggcaat ttcaccatac tatgcttctt taatggatcc ggataatcct     360
ttctgtccta ttcgaatgag agctatccca agtattaagg aacttacaga taaatatgga     420
gttccagacc cgatggcaga agaatatact tctcccgctc ctttaataac acgtcgttat     480
cctgatcgac tgattataaa cgtaacaaat caatgtggca tgttctgtag acattgtcag     540
aggagacgca acataggaga agtggattat cctgcaaaac acgaagacat agaagcggca     600
ttagaatata ttcgaaataa tccagaaatt agagatgtgc tgataacagg gggagaccct     660
ctcactcttg aggatgaaaa aatcgactgg attttgtcag aattagataa aattccacat     720
gtagaaataa aacgaatagg gacggctgcc ccagtgactt ttccacagag aattaccgat     780
gaattatgca gattttaac aaaacatctg cctctgtaca ttaataccca gtttaatcat     840
ccaaaagaag ttactgaaga agcaaagag gcttgcttta aattagcaag agctggggtg     900
```

-continued

```
gcattaggaa atcaagcagt gcttttaaaa gggataaata atgaccctca tgttatgaaa      960
aagttaaacc acgaattact tagaattatg gttaaacctt actacatttt ccatgcgaaa     1020
tctgttcaag ggactaccca ttttgttact acagttcaag atggattaga gattatggaa     1080
caacttcgcg gttatacttc agggcttgcc attccgtggt atataatcaa tgcacctgaa     1140
gggcatggga agactcctat tgtgcctcag tatctcctta tggttgggaa agaatatgtt     1200
cttataagaa attgggaagg aaaagttttt gaatatccga atggcttccc tgacgattaa     1260
```

<210> SEQ ID NO 4
<211> LENGTH: 419
<212> TYPE: PRT
<213> ORGANISM: Thermoanaerobacter tengcongensis

<400> SEQUENCE: 4

```
Met Ser Ser Thr Gly Ser Leu Thr Val Glu Glu Lys Arg Lys Ile Ala
 1               5                  10                  15

Leu Gln Arg Ala Glu Glu Leu Lys Lys Ile Glu Pro Tyr Leu Arg
                20                  25                  30

Ala Ser Glu Lys Ile Glu Thr Gly Phe Lys Leu Ser Glu Lys Phe Arg
            35                  40                  45

Glu Asn Lys Glu Lys Ile Lys Asn Leu Phe Gly Ala Thr Glu Glu Glu
        50                  55                  60

Trp Asn Asp Trp Arg Trp Gln Ile Arg Asn Arg Ile Ser Asp Val Glu
65                  70                  75                  80

Thr Leu Lys Lys Ile Val Asn Leu Ser Glu Glu Ile Glu Asn Ile
                85                  90                  95

Lys Arg Val Ser Thr Arg Tyr Arg Trp Ala Ile Ser Pro Tyr Tyr Ala
            100                 105                 110

Ser Leu Met Asp Pro Asp Asn Pro Phe Cys Pro Ile Arg Met Arg Ala
        115                 120                 125

Ile Pro Ser Ile Lys Glu Leu Thr Asp Lys Tyr Gly Val Pro Asp Pro
    130                 135                 140

Met Ala Glu Glu Tyr Thr Ser Pro Ala Pro Leu Ile Thr Arg Arg Tyr
145                 150                 155                 160

Pro Asp Arg Leu Ile Ile Asn Val Thr Asn Gln Cys Gly Met Phe Cys
                165                 170                 175

Arg His Cys Gln Arg Arg Arg Asn Ile Gly Glu Val Asp Tyr Pro Ala
            180                 185                 190

Lys His Glu Asp Ile Glu Ala Ala Leu Glu Tyr Ile Arg Asn Asn Pro
        195                 200                 205

Glu Ile Arg Asp Val Leu Ile Thr Gly Gly Asp Pro Leu Thr Leu Glu
    210                 215                 220

Asp Glu Lys Ile Asp Trp Ile Leu Ser Glu Leu Asp Lys Ile Pro His
225                 230                 235                 240

Val Glu Ile Lys Arg Ile Gly Thr Ala Ala Pro Val Thr Phe Pro Gln
                245                 250                 255

Arg Ile Thr Asp Glu Leu Cys Lys Ile Leu Thr Lys His Leu Pro Leu
            260                 265                 270

Tyr Ile Asn Thr Gln Phe Asn His Pro Lys Glu Val Thr Glu Ala
        275                 280                 285

Lys Glu Ala Cys Phe Lys Leu Ala Arg Ala Gly Val Ala Leu Gly Asn
    290                 295                 300

Gln Ala Val Leu Leu Lys Gly Ile Asn Asn Asp Pro His Val Met Lys
```

-continued

```
                305                 310                 315                 320
Lys Leu Asn His Glu Leu Leu Arg Ile Met Val Lys Pro Tyr Tyr Ile
                    325                 330                 335
Phe His Ala Lys Ser Val Gln Gly Thr Thr His Phe Val Thr Thr Val
                340                 345                 350
Gln Asp Gly Leu Glu Ile Met Glu Gln Leu Arg Gly Tyr Thr Ser Gly
            355                 360                 365
Leu Ala Ile Pro Trp Tyr Ile Ile Asn Ala Pro Glu Gly His Gly Lys
        370                 375                 380
Thr Pro Ile Val Pro Gln Tyr Leu Leu Met Val Gly Lys Glu Tyr Val
385                 390                 395                 400
Leu Ile Arg Asn Trp Glu Gly Lys Val Phe Glu Tyr Pro Asn Gly Phe
                405                 410                 415
Pro Asp Asp

<210> SEQ ID NO 5
<211> LENGTH: 1242
<212> TYPE: DNA
<213> ORGANISM: Desulfitobacterium hafniense

<400> SEQUENCE: 5
atggcaatag aatttctacc ccctaaccca agacaggctt cacaagcaag agctttggaa      60
ttaaaacaaa aagttcaatc ctacaacaaa cgcaaagaaa cgattccctg cggccttgcc     120
ttaagcgaag aatttaatga aaaccgagac tttatactgg atcagttaga tgctgacctg     180
gagcattggc aggattggaa gtggcagctt aaaaaccgta ttcaggatgc tgaaaacttg     240
agcaccctgc ttcccctgac ccccaagcaa agacatgaaa tcaacgaggt gggcaaggct     300
taccgttggg ctgtttcacc ctattattta agcctgatcg ataaagatga tcctcaggat     360
cccatccgtc tgcaaagtct cccctctgtg aagagatcc tcgacgattc cggagaagca     420
gatcccatgg agaagagta tacatcccct gcgccttgca tcacacgtcg ttacccggat     480
cgcctcatta ttaatgtaac caatttgtgt gctatgtatt gcaggcactg ccaacgccga     540
cggaatatcg gggaaattga cctccatgaa acccgtgcta actggaggc cgccctggat     600 tatatacgct ccaatccaga gattcgggat gtgctagtca ccggtggcga tgctctcctt     660
ctcagcgatc aaatgctgga ctggttattg ggagaattgc atgaaattaa gcatgtggag     720
atcaaacgta tcggcacccg ggttcccgtc actctgccca tgcgcattac cgatgagctc     780
tgcgctattc ttgaaaaata tccaccccctt tatatcaata ctcaattcaa tcatccccaa     840
gaggtgaccg aggagaccaa gaaagctgct gatcgcttaa tcaaagcggg agtcatctta     900
ggcaaccaag cagttcttct taaaggaatc aatgaccaac cagagattat gaaacgcctt     960
aaccaagaac ttcttaaaat tcgcgttcgc ccctactata ttttccatgc caaaaatgtt    1020
aaaggcacga gccactttat tccccgcatt caggacgggt taaggattat ggaaaacttg    1080
cgcggctaca cctctggttt ggccattccg acctatatta ttaatgcccc gggaggcggt    1140
ggcaaaaccc ccatcttacc acagtacctt atttccctaa cgatgaaga agcagtcatc    1200 agaacctggg aaggtaaggt tgtgcattat cctaatcatt aa                       1242

<210> SEQ ID NO 6
<211> LENGTH: 413
<212> TYPE: PRT
<213> ORGANISM: Desulfitobacterium hafniense

<400> SEQUENCE: 6
```

-continued

```
Met Ala Ile Glu Phe Leu Pro Pro Asn Pro Arg Gln Ala Ser Gln Ala
 1               5                  10                  15

Arg Ala Leu Glu Leu Lys Gln Lys Val Gln Ser Tyr Asn Lys Arg Lys
                20                  25                  30

Glu Thr Ile Pro Cys Gly Leu Ala Leu Ser Glu Glu Phe Asn Glu Asn
            35                  40                  45

Arg Asp Phe Ile Leu Asp Gln Leu Asp Ala Asp Leu Glu His Trp Gln
    50                  55                  60

Asp Trp Lys Trp Gln Leu Lys Asn Arg Ile Gln Asp Ala Glu Asn Leu
65                  70                  75                  80

Ser Thr Leu Leu Pro Leu Thr Pro Lys Gln Arg His Glu Ile Asn Glu
                85                  90                  95

Val Gly Lys Ala Tyr Arg Trp Ala Val Ser Pro Tyr Tyr Leu Ser Leu
                100                 105                 110

Ile Asp Lys Asp Asp Pro Gln Asp Pro Ile Arg Leu Gln Ser Leu Pro
            115                 120                 125

Ser Val Glu Glu Ile Leu Asp Asp Ser Gly Glu Ala Asp Pro Met Gly
    130                 135                 140

Glu Glu Tyr Thr Ser Pro Ala Pro Cys Ile Thr Arg Arg Tyr Pro Asp
145                 150                 155                 160

Arg Leu Ile Ile Asn Val Thr Asn Leu Cys Ala Met Tyr Cys Arg His
                165                 170                 175

Cys Gln Arg Arg Arg Asn Ile Gly Glu Ile Asp Leu His Glu Thr Arg
                180                 185                 190

Ala Asn Leu Glu Ala Ala Leu Asp Tyr Ile Arg Ser Asn Pro Glu Ile
            195                 200                 205

Arg Asp Val Leu Val Thr Gly Gly Asp Ala Leu Leu Leu Ser Asp Gln
    210                 215                 220

Met Leu Asp Trp Leu Leu Gly Glu Leu His Glu Ile Lys His Val Glu
225                 230                 235                 240

Ile Lys Arg Ile Gly Thr Arg Val Pro Val Thr Leu Pro Met Arg Ile
                245                 250                 255

Thr Asp Glu Leu Cys Ala Ile Leu Glu Lys Tyr Pro Pro Leu Tyr Ile
            260                 265                 270

Asn Thr Gln Phe Asn His Pro Gln Glu Val Thr Glu Glu Thr Lys Lys
    275                 280                 285

Ala Ala Asp Arg Leu Ile Lys Ala Gly Val Ile Leu Gly Asn Gln Ala
290                 295                 300

Val Leu Leu Lys Gly Ile Asn Asp Gln Pro Glu Ile Met Lys Arg Leu
305                 310                 315                 320

Asn Gln Glu Leu Leu Lys Ile Arg Val Arg Pro Tyr Tyr Ile Phe His
                325                 330                 335

Ala Lys Asn Val Lys Gly Thr Ser His Phe Ile Pro Arg Ile Gln Asp
            340                 345                 350

Gly Leu Arg Ile Met Glu Asn Leu Arg Gly Tyr Thr Ser Gly Leu Ala
    355                 360                 365

Ile Pro Thr Tyr Ile Ile Asn Ala Pro Gly Gly Gly Lys Thr Pro
370                 375                 380

Ile Leu Pro Gln Tyr Leu Ile Ser Leu Asn Asp Glu Glu Ala Val Ile
385                 390                 395                 400

Arg Thr Trp Glu Gly Lys Val Val His Tyr Pro Asn His
                405                 410
```

<210> SEQ ID NO 7
<211> LENGTH: 1248
<212> TYPE: DNA
<213> ORGANISM: Moorella thermoacetica

<400> SEQUENCE: 7

| | | |
|---|---|---|
| atgggaaggg aagctaaaag ggaaattgct cttgaccggg cagccgaatt gaaagccagg | 60 |
| attgtcgatt acctggaaga aagggagaag atcgccagcg gcctggaggc ggcagccgag | 120 |
| atcgaagcca gcaagcaacg tatcctggct tactttggcg ccggggaagc cgagtggcag | 180 |
| gactggcgct ggcagttgac ccaccgtatc acctcggtgg caaccctggc ggaactgatt | 240 |
| cccctgacag aagctgaaaa ggaagccata ctaaaggtag aacgtaccta tcgctgggcg | 300 |
| gtttctcctt actacctgag cctgatggga ccggaacctg attgccccat ccggcgccag | 360 |
| gctctgccca gtgccgccga actggaggat aaccatggcg tcctggaccc catggatgaa | 420 |
| gagttgacct ccccggcgcc ggctattacc cgccgttatc cggatcgttt gattatcaac | 480 |
| gtaaccaacc agtgtgctat gtactgtcgt cactgccagc ggcgtcgcaa tatcggtgaa | 540 |
| gtcgaccgca gtcgcagccg ccgggaactg gagcaggccc tccagtatat ccgccagaat | 600 |
| gaagagatcc gcgatgtcct gatcactggc ggtgacgccc tgatgctcag cgatgccatg | 660 |
| atcgactggt tgttgacgga actcgataat atccccacg tagaaattaa gcgcctgggc | 720 |
| accagggtgc cggtcactat gccccagcgg attaccccgg agctgtgccg ggttctggcc | 780 |
| aagcacccgc ccatctatct caatacccag ttcaaccacc ccggaggt taccgcggcc | 840 |
| gccaaagaag cctgcgatcg cctggtccag gccggggtgg tcctcggcaa ccaggcggtt | 900 |
| tgttaaagg gcgtcaacaa ccatccctt gtgatgcgta aattaaacca ggaactcttg | 960 |
| aaaataaggg tacggcccta ctatatcttc cacgccaagc cggtgaaggg gaccacccac | 1020 |
| tttattacct ccattgagga gggcgtggag atcatggata agctccgggg ctataccctcc | 1080 |
| ggcctggccg tgcctaccta taatcaat gccccccacg gtctgggcaa gaccccccatc | 1140 |
| ttgccacagt atgtaatcgc ccgtaatgat caccaggtga tcctgaggac ctgggagaag | 1200 |
| cggattattt tttactccaa cctgggacgc cagaaggaac aggcctaa | 1248 |

<210> SEQ ID NO 8
<211> LENGTH: 415
<212> TYPE: PRT
<213> ORGANISM: Moorella thermoacetica

<400> SEQUENCE: 8

Met Gly Arg Glu Ala Lys Arg Glu Ile Ala Leu Asp Arg Ala Glu
1               5                   10                  15

Leu Lys Ala Arg Ile Val Asp Tyr Leu Glu Glu Arg Glu Lys Ile Ala
            20                  25                  30

Ser Gly Leu Glu Ala Ala Ala Glu Ile Glu Ala Ser Lys Gln Arg Ile
        35                  40                  45

Leu Ala Tyr Phe Gly Ala Gly Glu Ala Glu Trp Gln Asp Trp Arg Trp
    50                  55                  60

Gln Leu Thr His Arg Ile Thr Ser Val Ala Thr Leu Ala Glu Leu Ile
65                  70                  75                  80

Pro Leu Thr Glu Ala Glu Lys Glu Ala Ile Leu Lys Val Glu Arg Thr
                85                  90                  95

Tyr Arg Trp Ala Val Ser Pro Tyr Tyr Leu Ser Leu Met Gly Pro Glu
            100                 105                 110

```
Pro Asp Cys Pro Ile Arg Arg Gln Ala Leu Pro Ser Ala Ala Glu Leu
        115                 120                 125

Glu Asp Asn His Gly Val Leu Asp Pro Met Asp Glu Glu Leu Thr Ser
130                 135                 140

Pro Ala Pro Ala Ile Thr Arg Arg Tyr Pro Asp Arg Leu Ile Ile Asn
145                 150                 155                 160

Val Thr Asn Gln Cys Ala Met Tyr Cys Arg His Cys Gln Arg Arg
                165                 170                 175

Asn Ile Gly Glu Val Asp Arg Ser Arg Ser Arg Arg Glu Leu Glu Gln
            180                 185                 190

Ala Leu Gln Tyr Ile Arg Gln Asn Glu Glu Ile Arg Asp Val Leu Ile
        195                 200                 205

Thr Gly Gly Asp Ala Leu Met Leu Ser Asp Ala Met Ile Asp Trp Leu
    210                 215                 220

Leu Thr Glu Leu Asp Asn Ile Pro His Val Glu Ile Lys Arg Leu Gly
225                 230                 235                 240

Thr Arg Val Pro Val Thr Met Pro Gln Arg Ile Thr Pro Glu Leu Cys
                245                 250                 255

Arg Val Leu Ala Lys His Pro Pro Ile Tyr Leu Asn Thr Gln Phe Asn
            260                 265                 270

His Pro Arg Glu Val Thr Ala Ala Lys Glu Ala Cys Asp Arg Leu
        275                 280                 285

Val Gln Ala Gly Val Val Leu Gly Asn Gln Ala Val Leu Leu Lys Gly
    290                 295                 300

Val Asn Asn His Pro Phe Val Met Arg Lys Leu Asn Gln Glu Leu Leu
305                 310                 315                 320

Lys Ile Arg Val Arg Pro Tyr Tyr Ile Phe His Ala Lys Pro Val Lys
                325                 330                 335

Gly Thr Thr His Phe Ile Thr Ser Ile Glu Glu Gly Val Glu Ile Met
            340                 345                 350

Asp Lys Leu Arg Gly Tyr Thr Ser Gly Leu Ala Val Pro Thr Tyr Ile
        355                 360                 365

Ile Asn Ala Pro His Gly Leu Gly Lys Thr Pro Ile Leu Pro Gln Tyr
370                 375                 380

Val Ile Ala Arg Asn Asp His Gln Val Ile Leu Arg Thr Trp Glu Lys
385                 390                 395                 400

Arg Ile Ile Phe Tyr Ser Asn Leu Gly Arg Gln Lys Glu Gln Ala
                405                 410                 415

<210> SEQ ID NO 9
<211> LENGTH: 1269
<212> TYPE: DNA
<213> ORGANISM: Syntrophomonas wolfei

<400> SEQUENCE: 9
ttgttgttaa gagaagattt gataaacgaa gaaattcggg agatgaaacg cgaagtatct      60
ttacgtaggg cggatgagct caaacaggaa atttctgact atcttgatat cgaatctact     120
attgaaacgg gaatgcgatt acatgaacgt aatctgcaca ataaggaaca tatcctgaaa     180
tactttgagg tcagcgagaa tgattgggat aattgggcct ggcaaatgag gaatcgcatc     240
aatgatggaa atgtgctggc ttccattctg ggcttaaatg aattcgaagt gcagacaatt     300
aaaagggttt ccaaaaaagt ccgctgggct atttctccct attatcttag tttaatcgat     360
tttgaaaatt acgcggcgtc acccatttac aagcagtctg tccccagtct gcatgaaata     420
```

-continued

```
atagaatgta agggtgagga tgaccccatg ggagaagaga tgagtagtcc tgctccccgt      480
attacacgtc gttatcccga ccgacttata atcaatgtta ccaatcaatg tgctatgtac      540
tgccgccatt gtcagcgccg tagaaatttc ggtgaaactg ataaccatgc cgcccataaa      600
gacctggaag ctgccctgca gtacattaaa aacaattctg aaatacggga tgttcttatt      660
accggtgggg atgctctaat gcttagcgat cgtacacttg actggttact gggagaactc      720
gatgccattt cacatgttga aattaagcgt attggtacca ggacaccggt aacacttcca      780
caaagaataa ccgccaatct ttgtgcagtg ctaaaaaggc atacacccat atatattaat      840
acccaattta attcaccgct ggaagttact ccggaagcca acaggcctg tgatcggctt       900 attgaagcag gagtagtatt gggtaaccag gctgttctgc taaagggaat caacgataat      960
gtccatgtta tgaaaaaact taaccaggag ttgctgaaaa tccgggttcg ccccctactat    1020 ttattccagg ccaaagaggt aaaaggaact acccattta ttagcccggt caataccggc      1080
ctggatatta tgaagcattt acggggctat acttctggcc tggccatccc cacttatgtt    1140
atcaacgcac caggaggtta cgtaaaaact ccagttaacc cggaatatgt actggatatt    1200
aatgaaaatg aagttataat tagtacctgg cagggtaaaa cttttaacta tccccatcgt    1260
aacaattag                                                             1269
```

```
<210> SEQ ID NO 10
<211> LENGTH: 422
<212> TYPE: PRT
<213> ORGANISM: Syntrophomonas wolfei

<400> SEQUENCE: 10
```

```
Met Leu Leu Arg Glu Asp Leu Ile Asn Glu Glu Ile Arg Glu Met Lys
  1               5                  10                  15

Arg Glu Val Ser Leu Arg Arg Ala Asp Glu Leu Lys Gln Glu Ile Ser
                 20                  25                  30

Asp Tyr Leu Asp Ile Glu Ser Thr Ile Glu Thr Gly Met Arg Leu His
             35                  40                  45

Glu Arg Asn Leu His Asn Lys Glu His Ile Leu Lys Tyr Phe Glu Val
         50                  55                  60

Ser Glu Asn Asp Trp Asp Asn Trp Ala Trp Gln Met Arg Asn Arg Ile
 65                  70                  75                  80

Asn Asp Gly Asn Val Leu Ala Ser Ile Leu Gly Leu Asn Glu Phe Glu
                 85                  90                  95

Val Gln Thr Ile Lys Arg Val Ser Lys Lys Val Arg Trp Ala Ile Ser
                100                 105                 110

Pro Tyr Tyr Leu Ser Leu Ile Asp Phe Glu Asn Tyr Ala Ala Ser Pro
            115                 120                 125

Ile Tyr Lys Gln Ser Val Pro Ser Leu His Glu Ile Ile Glu Cys Lys
        130                 135                 140

Gly Glu Asp Asp Pro Met Gly Glu Glu Met Ser Ser Pro Ala Pro Arg
145                 150                 155                 160

Ile Thr Arg Arg Tyr Pro Asp Arg Leu Ile Ile Asn Val Thr Asn Gln
                165                 170                 175

Cys Ala Met Tyr Cys Arg His Cys Gln Arg Arg Arg Asn Phe Gly Glu
            180                 185                 190

Thr Asp Asn His Ala Ala His Lys Asp Leu Glu Ala Ala Leu Gln Tyr
        195                 200                 205

Ile Lys Asn Asn Ser Glu Ile Arg Asp Val Leu Ile Thr Gly Gly Asp
    210                 215                 220
```

```
Ala Leu Met Leu Ser Asp Arg Thr Leu Asp Trp Leu Leu Gly Glu Leu
225                 230                 235                 240

Asp Ala Ile Ser His Val Glu Ile Lys Arg Ile Gly Thr Arg Thr Pro
            245                 250                 255

Val Thr Leu Pro Gln Arg Ile Thr Ala Asn Leu Cys Ala Val Leu Lys
        260                 265                 270

Arg His Thr Pro Ile Tyr Ile Asn Thr Gln Phe Asn Ser Pro Leu Glu
    275                 280                 285

Val Thr Pro Glu Ala Lys Gln Ala Cys Asp Arg Leu Ile Glu Ala Gly
290                 295                 300

Val Val Leu Gly Asn Gln Ala Val Leu Leu Lys Gly Ile Asn Asp Asn
305                 310                 315                 320

Val His Val Met Lys Lys Leu Asn Gln Glu Leu Leu Lys Ile Arg Val
                325                 330                 335

Arg Pro Tyr Tyr Leu Phe Gln Ala Lys Glu Val Lys Gly Thr Thr His
            340                 345                 350

Phe Ile Ser Pro Val Asn Thr Gly Leu Asp Ile Met Lys His Leu Arg
        355                 360                 365

Gly Tyr Thr Ser Gly Leu Ala Ile Pro Thr Tyr Val Ile Asn Ala Pro
    370                 375                 380

Gly Gly Tyr Gly Lys Thr Pro Val Asn Pro Glu Tyr Val Leu Asp Ile
385                 390                 395                 400

Asn Glu Asn Glu Val Ile Ile Ser Thr Trp Gln Gly Lys Thr Phe Asn
                405                 410                 415

Tyr Pro His Arg Asn Asn
            420

<210> SEQ ID NO 11
<211> LENGTH: 1269
<212> TYPE: DNA
<213> ORGANISM: Alkaliphilus metalliredigenes

<400> SEQUENCE: 11
gtgaatcata ccgatacaac aaacagtcgt caaatttcaa tcgatcgagc taagcatcta    60
aaattaacca tacaggatta cttagagata aaagacctca ttcccaaagg attatctcgt   120
caagtggaaa tcgaagcgaa aaagcaaaaa atcctatccc atttggtgc tactgaagat    180 aattggaatg attggcaatg gcaattaagc aatcgaatat ctgatgttga taccttaaca   240 aaataatta agttagatga taagaaatt gaagatataa aaaaagtagg acaagaattt     300
agatggtcag tatcacctta ttacaccact ctaattgatg acaataataa gtattgtcca   360
attaaactta tggctatacc ccatggctac gaaattgcca ataccaaagg agatacagat   420
ccaatggcag aagagttcac gaatcctgct ggatcaatta cacgccgcta tcccgatcga   480
ttaattatta atgtaaccaa tgaatgtgca atgtactgta cattgtca acgaagaaga    540 aacataggaa ctaatgatct ccatacatcc cgagaggttt acaagaatc gattgattat    600 attcgtgata atcctgaaat ccgggatgta ttaattactg gtggcgacgc attgaccctt   660
tctaatagta tgcttgattg gttattggga gaattacatg caattccatc cgtagactat   720
attagattgg gctctcgtac attggtcact atgccccaaa gaatcacaga taagttgatc   780
aatattctta aaagtaccc acctattttt attaataccc actttaatca ccccatggag    840
attacagaag agtccaaggc agcatgtgat agattatcca atgcgggcat tccattaggt   900
aaccaagcag ttctccttaa tggcattaat aataataagt ttgtcatgag attacttaat   960
```

-continued

```
cacgaactat taaaatgtcg tgttcgtcct tactatatat tccatgcgaa acatgttatt   1020
ggcactagtc attttaacac gtctgttgat gatggcatcg aaatcatgga gtacttaaga   1080
ggctacacat ctggtatggc aattccaacc tatatcatta atgcccctgg cggaaaagga   1140
aaaactccta tacttccaca atatctaatt tctagaggct ctcattctat taaaattaga   1200
acttgggatg gtgaagtgat tgattatcca aatcacccta caattccaat tgaagaaaca   1260
ctaaagtaa                                                          1269
```

<210> SEQ ID NO 12
<211> LENGTH: 422
<212> TYPE: PRT
<213> ORGANISM: Alkaliphilus metalliredigenes

<400> SEQUENCE: 12

```
Met Asn His Thr Asp Thr Thr Asn Ser Arg Gln Ile Ser Ile Asp Arg
  1               5                  10                  15

Ala Lys His Leu Lys Leu Thr Ile Gln Asp Tyr Leu Glu Ile Lys Asp
             20                  25                  30

Leu Ile Pro Lys Gly Leu Ser Arg Gln Val Glu Ile Glu Ala Lys Lys
         35                  40                  45

Gln Lys Ile Leu Ser His Phe Gly Ala Thr Glu Asp Asn Trp Asn Asp
     50                  55                  60

Trp Gln Trp Gln Leu Ser Asn Arg Ile Ser Asp Val Asp Thr Leu Thr
 65                  70                  75                  80

Lys Ile Ile Lys Leu Asp Asp Lys Glu Ile Glu Asp Ile Lys Lys Val
                 85                  90                  95

Gly Gln Glu Phe Arg Trp Ser Val Ser Pro Tyr Tyr Thr Thr Leu Ile
            100                 105                 110

Asp Asp Asn Asn Lys Tyr Cys Pro Ile Lys Leu Met Ala Ile Pro His
        115                 120                 125

Gly Tyr Glu Ile Ala Asn Thr Lys Gly Asp Thr Asp Pro Met Ala Glu
    130                 135                 140

Glu Phe Thr Asn Pro Ala Gly Ser Ile Thr Arg Arg Tyr Pro Asp Arg
145                 150                 155                 160

Leu Ile Ile Asn Val Thr Asn Glu Cys Ala Met Tyr Cys Arg His Cys
                165                 170                 175

Gln Arg Arg Arg Asn Ile Gly Thr Asn Asp Leu His Thr Ser Arg Glu
            180                 185                 190

Val Leu Gln Glu Ser Ile Asp Tyr Ile Arg Asp Asn Pro Glu Ile Arg
        195                 200                 205

Asp Val Leu Ile Thr Gly Gly Asp Ala Leu Thr Leu Ser Asn Ser Met
    210                 215                 220

Leu Asp Trp Leu Leu Gly Glu Leu His Ala Ile Pro Ser Val Asp Tyr
225                 230                 235                 240

Ile Arg Leu Gly Ser Arg Thr Leu Val Thr Met Pro Gln Arg Ile Thr
                245                 250                 255

Asp Lys Leu Ile Asn Ile Leu Lys Lys Tyr Pro Pro Ile Phe Ile Asn
            260                 265                 270

Thr His Phe Asn His Pro Met Glu Ile Thr Glu Glu Ser Lys Ala Ala
        275                 280                 285

Cys Asp Arg Leu Ser Asn Ala Gly Ile Pro Leu Gly Asn Gln Ala Val
    290                 295                 300

Leu Leu Asn Gly Ile Asn Asn Asn Lys Phe Val Met Arg Leu Leu Asn
```

|  | 305 |  |  | 310 |  |  |  | 315 |  |  |  | 320 |  |  |
|---|---|---|---|---|---|---|---|---|---|---|---|---|---|---|
| His | Glu | Leu | Leu | Lys | Cys | Arg | Val | Arg | Pro | Tyr | Tyr | Ile | Phe | His | Ala |
|  |  |  |  | 325 |  |  |  |  | 330 |  |  |  |  | 335 |  |

Lys His Val Ile Gly Thr Ser His Phe Asn Thr Ser Val Asp Asp Gly
        340                 345                 350

Ile Glu Ile Met Glu Tyr Leu Arg Gly Tyr Thr Ser Gly Met Ala Ile
        355                 360                 365

Pro Thr Tyr Ile Ile Asn Ala Pro Gly Gly Lys Gly Lys Thr Pro Ile
        370                 375                 380

Leu Pro Gln Tyr Leu Ile Ser Arg Gly Ser His Ser Ile Lys Ile Arg
385                 390                 395                 400

Thr Trp Asp Gly Glu Val Ile Asp Tyr Pro Asn His Pro Thr Ile Pro
                405                 410                 415

Ile Glu Glu Thr Leu Lys
        420

<210> SEQ ID NO 13
<211> LENGTH: 1224
<212> TYPE: DNA
<213> ORGANISM: Caldicellulosiruptor saccharolyticus

<400> SEQUENCE: 13
atggaaaagt tagatgttat taacaacaga gaaagattcg aaaagttaaa agaagctatt      60
aaagactact tagaggtcaa agacacaatc aaaactggca tagatgatga ggaaaagatt     120
gaatatcaaa aagaaagat  tctttcctac tttggtgcaa gcgaaaagga ctgggaaaat     180
tataagtggc agctgaaaaa tagaattacc tcggccaaaa tattaaaaga acttttaaac     240
cttgatgaaa aagaagcaca gcaaatagaa gaagtagcca aaatttaccg ttttgcaatc     300
tcaccttact atctctcttt gattgaccca agtgatcctc actgtccaat aaagaagcaa     360
tcagtcccaa gctcatttga gcttatagaa aaggtgagc  ttgacccaat ggacgaagag     420
catacatccc ctacaaagat tattacacag cgctatcctg acaggctcat aataaaagtt     480
acaaacatat gtgggatgtt ttgcagattc tgtcaaagaa gaagacttat tggtgagact     540
gacacacacg catcgctgga tgatattacg gatgcaattg aatatgtagc acaaaatcca     600
aatatcagag atgttctcat acaggtggc  gatgccctga tgctctctga tgagattttg     660
gagtggattt taaggtcgct aaggcaaata cctcatgttg agataatcag aattggaaca     720
agagcacctg tgacgttgcc acaaaggatt acaaaagagc ttgttgatat gctaaaaaag     780
tatcaccct  a tttatgtaaa cacccacttt aaccaccca  gtgagataac aaaagaatca     840
aaaagagctt gtgagatgct tgcagatggc ggcattccgc ttggcaacca gatggttttg     900
ttaaatgggg tcaacaacga caaatacgtt gtgagaaggc tcaatcaaca gcttttaaaa     960
atccgagtaa agccatatta tatctttcat ccaaaaaggg taaaaggtac atcgcacttt    1020
tgggtgacaa ttgaagaggg tatggagatt attgaaagcc tcagaggaag aacctcaggc    1080
atggcaattc ccacatacat cataaatgct ccaaaaggca aggaaaaac  accaattatg    1140
ccaaattatc ttctttactt tggtaaaggc aaggtagttt ttagaaactg ggaaggtgag    1200
gtttttgagg ttgagaatgg gtaa                                          1224

<210> SEQ ID NO 14
<211> LENGTH: 407
<212> TYPE: PRT
<213> ORGANISM: Caldicellulosiruptor saccharolyticus

<400> SEQUENCE: 14

```
Met Glu Lys Leu Asp Val Ile Asn Asn Arg Glu Arg Phe Glu Lys Leu
  1               5                  10                  15

Lys Glu Ala Ile Lys Asp Tyr Leu Glu Val Lys Asp Thr Ile Lys Thr
             20                  25                  30

Gly Ile Asp Asp Glu Glu Lys Ile Glu Tyr Gln Lys Arg Lys Ile Leu
         35                  40                  45

Ser Tyr Phe Gly Ala Ser Glu Lys Asp Trp Glu Asn Tyr Lys Trp Gln
     50                  55                  60

Leu Lys Asn Arg Ile Thr Ser Ala Lys Ile Leu Lys Glu Leu Leu Asn
 65                  70                  75                  80

Leu Asp Glu Lys Glu Ala Gln Gln Ile Glu Glu Val Ala Lys Ile Tyr
                 85                  90                  95

Arg Phe Ala Ile Ser Pro Tyr Tyr Leu Ser Leu Ile Asp Pro Ser Asp
                100                 105                 110

Pro His Cys Pro Ile Lys Lys Gln Ser Val Pro Ser Ser Phe Glu Leu
            115                 120                 125

Ile Glu Lys Gly Glu Leu Asp Pro Met Asp Glu Glu His Thr Ser Pro
        130                 135                 140

Thr Lys Ile Ile Thr Gln Arg Tyr Pro Asp Arg Leu Ile Ile Lys Val
145                 150                 155                 160

Thr Asn Ile Cys Gly Met Phe Cys Arg Phe Cys Gln Arg Arg Arg Leu
                165                 170                 175

Ile Gly Glu Thr Asp Thr His Ala Ser Leu Asp Asp Ile Thr Asp Ala
            180                 185                 190

Ile Glu Tyr Val Ala Gln Asn Pro Asn Ile Arg Asp Val Leu Ile Thr
        195                 200                 205

Gly Gly Asp Ala Leu Met Leu Ser Asp Glu Ile Leu Glu Trp Ile Leu
210                 215                 220

Arg Ser Leu Arg Gln Ile Pro His Val Glu Ile Ile Arg Ile Gly Thr
225                 230                 235                 240

Arg Ala Pro Val Thr Leu Pro Gln Arg Ile Thr Lys Glu Leu Val Asp
                245                 250                 255

Met Leu Lys Lys Tyr His Pro Ile Tyr Val Asn Thr His Phe Asn His
            260                 265                 270

Pro Arg Glu Ile Thr Lys Glu Ser Lys Arg Ala Cys Glu Met Leu Ala
        275                 280                 285

Asp Gly Gly Ile Pro Leu Gly Asn Gln Met Val Leu Leu Asn Gly Val
290                 295                 300

Asn Asn Asp Lys Tyr Val Val Arg Arg Leu Asn Gln Gln Leu Leu Lys
305                 310                 315                 320

Ile Arg Val Lys Pro Tyr Tyr Ile Phe His Pro Lys Arg Val Lys Gly
                325                 330                 335

Thr Ser His Phe Trp Val Thr Ile Glu Glu Gly Met Glu Ile Ile Glu
            340                 345                 350

Ser Leu Arg Gly Arg Thr Ser Gly Met Ala Ile Pro Thr Tyr Ile Ile
        355                 360                 365

Asn Ala Pro Lys Gly Lys Gly Lys Thr Pro Ile Met Pro Asn Tyr Leu
370                 375                 380

Leu Tyr Phe Gly Lys Gly Lys Val Val Phe Arg Asn Trp Glu Gly Glu
385                 390                 395                 400

Val Phe Glu Val Glu Asn Gly
                405
```

<210> SEQ ID NO 15
<211> LENGTH: 1269
<212> TYPE: DNA
<213> ORGANISM: Desulfotomaculum reducens

<400> SEQUENCE: 15

```
atgtctgttc atttaaagca agaagagttc cggctaagac aagaaaaacg aaaaattgct      60
ctaaaaaggg caaggagtt aaaagctcgt atcactgatt atcttgagaa caaggatcaa     120
attaaaaatg gttttgaggt gcaagaacag tacaatcggg caaaacaaac tttactaaat     180
tttttaatg cagataatga gcagtgggaa attggcact ggcaaatggc aaatcgtatt      240
aaagatgtta agtaataag ccagttaata gatctttccc cggctgaaaa agaggccatt      300
gaaaaagtgg ggcgccagta ccgttgggcg gtatcaccct attatatggc tctggcaatg     360
gtaagtggtt ccggtggccc tgtttggtta caggctatac cctgtataga agaagtaaag     420
gatcgttacg gtgtagaaga tcccatggga gaagaataca cttcacctgt ggaaggggta     480
acaagacgct acccagaccg tttgattatt aatgtaacaa atcaatgtgc tatgtattgt     540
cgccactgcc aacgacgtag aaatatcggg gaaattgatg ttcacaaatc acgtaaggtt     600
ttagaaggtg ccctgcagta tattagggaa ataaggaga taaggggatgt attaataact     660
ggtggggatg ctttattgtt atcagaccga caaattgaat ggctgctgac tgaattagat     720
aatattcctc atgtgaaat taagagattg ggaacacgta ctccggttac tatgccccaa     780
agaattacac cggagttatg taagatttta gagaaccatc caccgattta tatcaacacc     840
cagtttaatc atcctttgga agttacacca gaagcaaaaa aggcctgtga tatgttggta     900
aaagcaggtg ttgttctagg taatcaagct gtactactaa aaaatataaa taaccaaccg     960
gatgttatga gaggttaaa ccaaagtctc ctaaccattc gagttcgccc ttactatata    1020
ttccatgcta aagccgtaaa aggaaccaga catttatca ctggagtaga tgacggcatt    1080
gctattatgg aacaattaag aggctatacc tcaggacttg ctgttcctac gtatatcatt    1140
aatgcccca atggttatgg taaaactcct gtacttcccc agtatattat tgagaataaa    1200
aatgatcaag ttaccttag aacctgggaa aagaggatta ttccctataa tattagcgga    1260
aaacattag                                                           1269
```

<210> SEQ ID NO 16
<211> LENGTH: 422
<212> TYPE: PRT
<213> ORGANISM: Desulfotomaculum reducens

<400> SEQUENCE: 16

Met Ser Val His Leu Lys Gln Glu Glu Phe Arg Leu Arg Gln Glu Lys
 1               5                  10                  15

Arg Lys Ile Ala Leu Lys Arg Ala Lys Glu Leu Lys Ala Arg Ile Thr
            20                  25                  30

Asp Tyr Leu Glu Asn Lys Asp Gln Ile Lys Asn Gly Phe Glu Val Gln
        35                  40                  45

Glu Gln Tyr Asn Arg Ala Lys Gln Thr Leu Leu Asn Phe Phe Asn Ala
    50                  55                  60

Asp Asn Glu Gln Trp Glu Asn Trp His Trp Gln Met Ala Asn Arg Ile
65                  70                  75                  80

Lys Asp Val Lys Val Ile Ser Gln Leu Ile Asp Leu Ser Pro Ala Glu
                85                  90                  95

```
Lys Glu Ala Ile Glu Lys Val Gly Arg Gln Tyr Arg Trp Ala Val Ser
                100                 105                 110

Pro Tyr Tyr Met Ala Leu Ala Met Val Ser Gly Ser Gly Gly Pro Val
            115                 120                 125

Trp Leu Gln Ala Ile Pro Cys Ile Glu Glu Val Lys Asp Arg Tyr Gly
        130                 135                 140

Val Glu Asp Pro Met Gly Glu Glu Tyr Thr Ser Pro Val Glu Gly Val
145                 150                 155                 160

Thr Arg Arg Tyr Pro Asp Arg Leu Ile Ile Asn Val Thr Asn Gln Cys
                165                 170                 175

Ala Met Tyr Cys Arg His Cys Gln Arg Arg Asn Ile Gly Glu Ile
            180                 185                 190

Asp Val His Lys Ser Arg Lys Val Leu Glu Gly Ala Leu Gln Tyr Ile
        195                 200                 205

Arg Glu Asn Lys Glu Ile Arg Asp Val Leu Ile Thr Gly Gly Asp Ala
    210                 215                 220

Leu Leu Leu Ser Asp Arg Gln Ile Glu Trp Leu Leu Thr Glu Leu Asp
225                 230                 235                 240

Asn Ile Pro His Val Glu Ile Lys Arg Leu Gly Thr Arg Thr Pro Val
                245                 250                 255

Thr Met Pro Gln Arg Ile Thr Pro Glu Leu Cys Lys Ile Leu Glu Asn
            260                 265                 270

His Pro Pro Ile Tyr Ile Asn Thr Gln Phe Asn His Pro Leu Glu Val
        275                 280                 285

Thr Pro Glu Ala Lys Lys Ala Cys Asp Met Leu Val Lys Ala Gly Val
    290                 295                 300

Val Leu Gly Asn Gln Ala Val Leu Leu Lys Asn Ile Asn Asn Gln Pro
305                 310                 315                 320

Asp Val Met Lys Arg Leu Asn Gln Ser Leu Leu Thr Ile Arg Val Arg
                325                 330                 335

Pro Tyr Tyr Ile Phe His Ala Lys Ala Val Lys Gly Thr Arg His Phe
            340                 345                 350

Ile Thr Gly Val Asp Asp Gly Ile Ala Ile Met Glu Gln Leu Arg Gly
        355                 360                 365

Tyr Thr Ser Gly Leu Ala Val Pro Thr Tyr Ile Ile Asn Ala Pro Asn
    370                 375                 380

Gly Tyr Gly Lys Thr Pro Val Leu Pro Gln Tyr Ile Ile Glu Asn Lys
385                 390                 395                 400

Asn Asp Gln Val Thr Leu Arg Thr Trp Glu Lys Arg Ile Ile Pro Tyr
                405                 410                 415

Asn Ile Ser Gly Lys His
            420
```

<210> SEQ ID NO 17
<211> LENGTH: 1236
<212> TYPE: DNA
<213> ORGANISM: Carboxydothermus hydrogenoformans

<400> SEQUENCE: 17

```
atgaatagag caagaatttc gcagaaagat gaaggattga acggcaaag agagcttacc      60
cggattggtc gtagtaggtt aagggaaaga aaaaaggttt tatcgggatt tgaagcctgg    120
gaaaaaattt aaaacaaaaa agagaagatt ttaaaggtat taggtggaac ggaagaagac    180
tggcaggatt ggcgctggca gttgaaaaat cggataacaa cgccggaagt tttacgaaaa    240
```

-continued

```
attttgcctt taagcgacca ggtcctctgg gaacttgagg aggtcagtaa ggtttatcgc    300
tttgccattt cgccttatta tttgagcttg attgatcccg atgatcccga ttgcggtatt    360
aagaaacagt cgattccttc cattttggag gttttagatg ataccggtga acttgacccg    420
atgaatgaag cggggacttc gccggtggcg gcggttaccc ggcgttatcc ggaccgctta    480
ataattaatg ttaccaatat gtgcgggatg tattgccgtc actgtcagcg gcgaagaaat    540
atcggtgagg ttgaccggaa aactcccagg gagcagataa aagaagccct tctttacatc    600
cgggagcata agaaatccg gatgttttta ttaccggtg gggatgcact tctcttatcc    660
gatttggagc tggactggat attaaaagaa ctttccgaaa tacccatgt agaaattaaa    720
aggattggta cccgggtacc ggtgaccttg ccgcaaaggg ttaccgataa tctggttaaa    780
atattaaaaa ataccccgcc gatatatatc aatcccagt ttaaccatcc ccgggaggta    840
actcctgagg ccaaaaaagc ggtggataaa ttaattgaag cgggggtggt attaggtaat    900
caggcggtgc ttttaaaagg ggtaaatgac aatcccgtaa ttatggagaa attgaaccat    960
gagcttttaa aaattcgggt acggccgtac tatatcttcc aggcgaagag ggtacgggga   1020
acgatgcatt tgttcccaa gattgaagac ggattaagga taatgaaag cttgcggggc   1080
tatacctcgg gactggcagt gccgtattat atcgtcaacg cgcctggagg ctttgggaaa   1140
attccgcttt acccagta tttaattgaa ctctcggaag aagaagcagt tttacgcaac   1200
tgggaaggcc ggataattag atatccgaat aattaa                            1236
```

<210> SEQ ID NO 18
<211> LENGTH: 411
<212> TYPE: PRT
<213> ORGANISM: Carboxydothermus hydrogenoformans

<400> SEQUENCE: 18

```
Met Asn Arg Ala Arg Ile Ser Gln Lys Asp Glu Gly Leu Lys Arg Gln
  1               5                  10                  15

Arg Glu Leu Thr Arg Ile Gly Arg Ser Arg Leu Arg Glu Arg Lys Lys
             20                  25                  30

Val Leu Ser Gly Phe Glu Ala Trp Glu Lys Ile Leu Lys Gln Lys Glu
         35                  40                  45

Lys Ile Leu Lys Val Leu Gly Gly Thr Glu Glu Asp Trp Gln Asp Trp
     50                  55                  60

Arg Trp Gln Leu Lys Asn Arg Ile Thr Thr Pro Glu Val Leu Arg Lys
 65                  70                  75                  80

Ile Leu Pro Leu Ser Asp Gln Val Leu Trp Glu Leu Glu Glu Val Ser
                 85                  90                  95

Lys Val Tyr Arg Phe Ala Ile Ser Pro Tyr Tyr Leu Ser Leu Ile Asp
            100                 105                 110

Pro Asp Pro Asp Cys Gly Ile Lys Lys Gln Ser Ile Pro Ser Ile
            115                 120                 125

Leu Glu Val Leu Asp Asp Thr Gly Glu Leu Asp Pro Met Asn Glu Ala
        130                 135                 140

Gly Thr Ser Pro Val Ala Ala Val Thr Arg Arg Tyr Pro Asp Arg Leu
145                 150                 155                 160

Ile Ile Asn Val Thr Asn Met Cys Gly Met Tyr Cys Arg His Cys Gln
                165                 170                 175

Arg Arg Arg Asn Ile Gly Glu Val Asp Arg Lys Thr Pro Arg Glu Gln
            180                 185                 190

Ile Lys Glu Ala Leu Leu Tyr Ile Arg Glu His Lys Glu Ile Arg Asp
```

-continued

```
            195                 200                 205
Val Leu Ile Thr Gly Gly Asp Ala Leu Leu Ser Asp Leu Glu Leu
    210                 215                 220

Asp Trp Ile Leu Lys Glu Leu Ser Glu Ile Pro His Val Glu Ile Lys
225                 230                 235                 240

Arg Ile Gly Thr Arg Val Pro Val Thr Leu Pro Gln Arg Val Thr Asp
                245                 250                 255

Asn Leu Val Lys Ile Leu Lys Lys Tyr Pro Pro Ile Tyr Ile Asn Thr
            260                 265                 270

Gln Phe Asn His Pro Arg Glu Val Thr Pro Glu Ala Lys Lys Ala Val
        275                 280                 285

Asp Lys Leu Ile Glu Ala Gly Val Val Leu Gly Asn Gln Ala Val Leu
    290                 295                 300

Leu Lys Gly Val Asn Asp Asn Pro Val Ile Met Glu Lys Leu Asn His
305                 310                 315                 320

Glu Leu Leu Lys Ile Arg Val Arg Pro Tyr Tyr Ile Phe Gln Ala Lys
                325                 330                 335

Arg Val Arg Gly Thr Met His Phe Val Pro Lys Ile Glu Asp Gly Leu
            340                 345                 350

Arg Ile Met Glu Ser Leu Arg Gly Tyr Thr Ser Gly Leu Ala Val Pro
        355                 360                 365

Tyr Tyr Ile Val Asn Ala Pro Gly Gly Phe Gly Lys Ile Pro Leu Leu
    370                 375                 380

Pro Gln Tyr Leu Ile Glu Leu Ser Glu Glu Ala Val Leu Arg Asn
385                 390                 395                 400

Trp Glu Gly Arg Ile Ile Arg Tyr Pro Asn Asn
                405                 410

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: variable naturally occurring amino acid
<220> FEATURE:
<221> NAME/KEY: MOD_RES
<222> LOCATION: (7)
<223> OTHER INFORMATION: variable naturally occurring amino acid
<220> FEATURE:
<221> NAME/KEY: MOD_RES
<222> LOCATION: (9)
<223> OTHER INFORMATION: variable naturally occurring amino acid

<400> SEQUENCE: 19

Cys Xaa Xaa Xaa Cys Arg Xaa Cys Xaa Arg
  1               5                  10

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ser or Thr
```

```
<220> FEATURE:
<221> NAME/KEY: MOD_RES
<222> LOCATION: (4)
<223> OTHER INFORMATION: Asp or Glu

<400> SEQUENCE: 20

Xaa Gly Gly Xaa
 1

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: variable naturally occurring amino acid
<220> FEATURE:
<221> NAME/KEY: MOD_RES
<222> LOCATION: (6)..(16)
<223> OTHER INFORMATION: variable naturally occurring amino acid

<400> SEQUENCE: 21

Gly Xaa Xaa Xaa Pro Xaa Xaa Xaa Xaa Xaa Xaa Xaa Xaa Xaa Xaa
 1               5                  10                  15
Lys

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: variable naturally occurring amino acid
<220> FEATURE:
<221> NAME/KEY: MOD_RES
<222> LOCATION: (4)..(7)
<223> OTHER INFORMATION: variable naturally occurring amino acid
<220> FEATURE:
<221> NAME/KEY: MOD_RES
<222> LOCATION: (8)..(10)
<223> OTHER INFORMATION: variable naturally occurring amino acid

<400> SEQUENCE: 22

Pro Xaa Tyr Xaa Xaa Xaa Xaa Lys Xaa Xaa Xaa Gly
 1               5                  10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: variable naturally occurring amino acid
<220> FEATURE:
<221> NAME/KEY: MOD_RES
<222> LOCATION: (7)..(12)
<223> OTHER INFORMATION: variable naturally occurring amino acid

<400> SEQUENCE: 23
```

Pro Xaa Xaa Xaa Xaa Asn Xaa Xaa Xaa Xaa Xaa Xaa Lys
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: variable naturally occurring amino acid
<220> FEATURE:
<221> NAME/KEY: MOD_RES
<222> LOCATION: (4)..(7)
<223> OTHER INFORMATION: variable naturally occurring amino acid
<220> FEATURE:
<221> NAME/KEY: MOD_RES
<222> LOCATION: (9)..(11)
<223> OTHER INFORMATION: variable naturally occurring amino acid

<400> SEQUENCE: 24

Pro Xaa Tyr Xaa Xaa Xaa Xaa Asp Xaa Xaa Xaa Gly
 1               5                  10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: variable naturally occurring amino acid
<220> FEATURE:
<221> NAME/KEY: MOD_RES
<222> LOCATION: (7)..(12)
<223> OTHER INFORMATION: variable naturally occurring amino acid

<400> SEQUENCE: 25

Pro Xaa Xaa Xaa Xaa Asp Xaa Xaa Xaa Xaa Xaa Xaa Lys
 1               5                  10

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acacatatga atgaacaaac tagaatatcc ttag                                  34

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgactcgagt taatcctgtg cttgttcttt tataag                                36

<210> SEQ ID NO 28

<211> LENGTH: 1260
<212> TYPE: DNA
<213> ORGANISM: Thermoanaerobacter tengcongensis

<400> SEQUENCE: 28

| | | | | | |
|---|---|---|---|---|---|
| atgagctcca | ccggtagcct | gactgtggaa | gaaaaacgta | aaattgccct | gcagcgcgca | 60 |
| gaggagctga | aaagaaaat | cgaaccatac | ctgcgtgcca | gcgagaaaat | cgaaacagga | 120 |
| tttaaactga | gcgaaaagtt | tcgtgaaaac | aagaaaaga | tcaagaacct | gtttggcgca | 180 |
| actgaagaag | aatggaacga | ttggcgctgg | cagatccgca | accgcatttc | agatgtggag | 240 |
| accctgaaga | aaattgttaa | cctgagcgaa | gaagaaattg | aaaacattaa | gcgcgtcagt | 300 |
| actcgctatc | gttgggcaat | tcgccgtat | tatgcatcgc | tgatggaccc | ggataaccct | 360 |
| ttttgcccga | ttcgcatgcg | cgcaatcccg | tctatcaaag | aactgacaga | taaatatggc | 420 |
| gtgccagatc | cgatggcgga | ggaatatacg | tccccggcgc | cgctgattac | tcgccgttat | 480 |
| ccggatcgtc | tgattatcaa | cgtgaccaat | caatgtggca | tgttttgccg | tcactgtcag | 540 |
| cgtcgccgca | atatcggcga | agtggactac | ccggcgaaac | atgaagatat | tgaagcggcg | 600 |
| ctgaatatat | ccgtaataa | tccagagatc | cgtgatgttc | tgatcacggg | cggcgatcca | 660 |
| ctgaccctgg | aagacgaaaa | gattgactgg | attctgagcg | aactggataa | aattccgcac | 720 |
| gtggaaatta | gcgcatcgg | taccgcggct | ccagtgacgt | tcccgcaacg | tattaccgac | 780 |
| gaactgtgta | aaattctgac | gaaacatctg | ccgctgtata | tcaacacaca | atttaaccat | 840 |
| ccgaaagagg | ttaccgaaga | ggcgaaagaa | gcctgtttta | aactggcgcg | tgcgggtgtg | 900 |
| gctctgggca | tcaggcggt | actgctgaaa | ggcatcaata | cgatccaca | tgtcatgaag | 960 |
| aaactgaatc | atgaactgct | gcgcatcatg | gtcaaacctt | attatatttt | ccacgcgaaa | 1020 |
| tctgtgcaag | gtactacaca | ttttgtgacc | accgttcagg | atggcctgga | aattatggag | 1080 |
| cagctgcgcg | ttatactag | tggtctggcg | atcccgtggt | atatcattaa | cgcaccggaa | 1140 |
| ggtcatggta | aaactccgat | cgttccgcag | tacctgctga | tggtaggaaa | ggaatacgtt | 1200 |
| ctgatccgca | attgggaagg | taaagtgttt | gaatatccga | acggtttccc | ggatgattaa | 1260 |

<210> SEQ ID NO 29
<211> LENGTH: 1242
<212> TYPE: DNA
<213> ORGANISM: Desulfitobacterium hafniense

<400> SEQUENCE: 29

| | | | | | |
|---|---|---|---|---|---|
| atggcgattg | aatttctgcc | gccgaatccg | cgtcaggcga | gccaggcgcg | cgcgctggaa | 60 |
| ctgaaacaga | aagtgcagag | ctataataaa | cgtaaagaaa | ccattccgtg | cggcctggcg | 120 |
| ctgagcgaag | aatttaacga | aaaccgtgat | tttattctgg | atcagctgga | tgcggatctg | 180 |
| gaacattggc | aggattggaa | atggcagctg | aaaaaccgca | ttcaggatgc | ggaaaatctg | 240 |
| agcaccctgc | tgccgctgac | cccgaaacag | cgccatgaaa | ttaatgaagt | gggcaaagcg | 300 |
| tatcgttggg | cggtgagccc | gtattatctg | agcctgattg | ataaagatga | tccgcaggat | 360 |
| ccgattcgcc | tgcagagcct | gccgagcgtg | aagaaattc | tggatgatag | cggtgaagcg | 420 |
| gatccgatgg | gcgaagaata | taccagcccg | gcgccgtgca | ttacccgccg | ctatccggat | 480 |
| cgcctgatta | ttaatgttac | caacctgtgc | gcgatgtatt | gccgtcattg | ccagcgccgc | 540 |
| cgtaatattg | gcgaaattga | tctgcatgaa | accgtgcga | acctggaagc | ggcgctggat | 600 |
| tatattcgta | gcaaccccgga | aattcgcgat | gtgctggtga | ccgtggcga | tgcgctgctg | 660 |
| ctgagcgatc | agatgctgga | ttggctgctg | ggcgaactgc | atgaaattaa | acatgtggaa | 720 |

```
attaaacgca ttggcacccg tgtgccggtg accctgccga tgcgcattac cgatgaactg      780
tgtgcgattc tggaaaaata tccgccgctg tatattaaca cccagtttaa ccatccgcag      840
gaagtgaccg aagaaaccaa aaaagcggcg gatcgcctga ttaaagcggg cgttattctg      900
ggcaatcagg cggttctgct gaaaggcatt aacgatcagc ggaaattat gaaacgtctg       960 aaccaggaac tgctgaaaat tcgtgtgcgc ccgtattata ttttcatgc gaaaaacgtg      1020 aaaggcacca gccattttat tccgcgtatt caggatggcc tgcgcattat ggaaaacctg     1080
cgtggttata ccagcggtct ggcgattccg acctatatta ttaacgcgcc gggtggtggc     1140
ggcaaaaccc cgattctgcc gcagtatctg attagcctga cgatgaaga agcggtgatt      1200 cgtacctggg aaggcaaagt ggtgcattat ccgaatcatt aa                        1242

<210> SEQ ID NO 30
<211> LENGTH: 1248
<212> TYPE: DNA
<213> ORGANISM: Moorella thermoacetica

<400> SEQUENCE: 30
atgggtcgtg aagcgaaacg cgaaattgcg ctggatcgtg cggcggaact gaaagcgcgt      60
attgtggatt atctggaaga acgtgaaaaa attgcgagcg gcctggaagc ggccgcggaa     120
atcgaagcca gcaaacagcg catcctggcc tattttggtg cgggcgaagc cgaatggcag     180
gattggcgtt ggcagctgac ccatcgcatt accagcgtgg cgaccctggc ggaactgatt     240
ccgctgaccg aagccgaaaa agaagccatt ctgaaagttg aacgtaccta tcgctgggcg     300
gtgagcccgt attatctgag cctgatgggc ccggaaccgg attgtccgat ccgtcgtcag     360
gcgctgccga gcgccgcgga actggaagat aaccatggcc tgctggatcc gatggatgaa     420
gaactgacca gcccggcgcc ggccattacc cgtcgttatc cggatcgcct gattattaac     480
gtgaccaacc agtgtgcgat gtattgccgc cattgccagc gtcgccgtaa tatcggtgaa     540
gtggatcgta ccgtagccg tcgtgaactg aacaggccc tgcagtatat tcgtcagaat       600
gaagaaattc gtgatgttct gattaccggt ggtgatgcgc tgatgctgag cgatgcgatg     660
attgattggc tgctgaccga actggataac attccgcatg ttgaaatcaa cgcctgggt     720 acccgtgtgc cggtgaccat gccgcagcgt atcaccccgg aactgtgccg tgttctggcc     780
aaacatccgc cgatctatct gaatacccag tttaatcatc cgcgcgaagt taccgcggcg     840
gcgaaagaag cgtgtgatcg cctggtgcag gcgggcgtgg ttctgggtaa ccaggcggtt     900
ctgctgaaag cgtgaataa ccatccgttt gtgatgcgta aactgaatca ggaactgctg      960
aaaatccgtg ttcgcccgta ttatatcttt catgcgaaac cggtgaaagg caccacccat    1020
ttcattacca gcattgaaga aggtgtggaa attatggata aactgcgtgg ctataccagc    1080
ggtctggcgg tgccgaccta tcattaat gcgccgcatg gtctgggcaa aaccccgatc      1140
ctgccgcagt atgttatcgc gcgtaacgat caccaggtga ttctgcgtac ctgggaaaaa    1200
cgcattatct tctatagcaa cctgggccgc cagaaagaac aggcgtaa                 1248

<210> SEQ ID NO 31
<211> LENGTH: 1269
<212> TYPE: DNA
<213> ORGANISM: Syntrophomonas wolfei

<400> SEQUENCE: 31
atgctgctgc gcgaagatct gattaacgaa gaaattcgcg aaatgaaacg cgaagtgagc      60
```

```
ctgcgtcgtg cggatgaact gaaacaggaa attagcgatt atctggatat tgaaagcacc      120
attgaaaccg gtatgcgtct gcatgaacgc aacctgcata acaaagaaca tattctgaaa      180
tattttgaag tgagcgaaaa cgattgggat aactgggcgt ggcagatgcg taaccgtatt      240
aatgatggta acgtgctggc gagcattctg ggcctgaatg aatttgaagt tcagaccatt      300
aaacgtgtga gcaaaaaagt gcgttgggcg attagcccgt attatctgag cctgattgat      360
tttgaaaatt atgcggcgag cccgatttat aaacagagcg tgccgagcct gcatgaaatt      420
attgaatgca aaggtgaaga tgatccgatg ggtgaagaaa tgagcagccc ggcgccgcgt      480
attaccctc gttatccgga tcgtctgatt attaatgtta ccaatcagtg cgcgatgtat      540
tgccgccatt gtcagcgccg ccgtaatttt ggtgaaaccg ataaccatgc ggcgcataaa      600
gatctggaag cggcgctgca gtatattaaa aataatagcg aaattcgtga tgtgctgatt      660
accggcggtg atgcgctgat gctgagcgat cgcaccctgg attggctgct gggtgaactg      720
gatgcgatta gccatgtgga aattaaacgc attggcaccc gtaccccggt gaccctgccg      780
cagcgtatta ccgcgaacct gtgcgcggtg ctgaaacgcc ataccccgat ttatattaat      840
acccagttta acagcccgct ggaagtgacc ccggaagcga acaggcgtg cgatcgcctg      900
attgaagcgg gcgtggttct gggtaatcag gcggtgctgc tgaaaggcat taacgataac      960
gtgcatgtga tgaaaaaact gaatcaggaa ctgctgaaaa ttcgtgtgcg tccgtattat     1020
ctgtttcagg cgaaagaagt gaaaggcacc acccatttta ttagcccggt taacaccggt     1080
ctggatatta tgaaacatct gcgtggttat accagcggcc tggcgattcc gacctatgtt     1140
attaatgcgc cgggtggtta tggtaaaacc ccggtgaatc cggaatatgt gctggatatt     1200
aatgaaaatg aagtgattat tagcacctgg cagggtaaaa cctttaacta tccgcatcgt     1260
aacaactaa                                                             1269
```

GLUTAMATE 2,3-AMINOMUTASES AND METHODS OF USE THEREOF

CROSS REFERENCES TO RELATED APPLICATIONS

This application claims priority to U.S. Provisional Application Ser. No. 60/725,350, filed Oct. 11, 2005, the entire contents of which is incorporated herein by reference and for all purposes.

GOVERNMENT RIGHTS

Part of the work performed during development of this invention utilized U.S. Government Funds, specifically the National Institute of Diabetes and Digestive and Kidney Diseases, Grant No. DK 28607. Therefore, the U.S. Government has certain rights in this invention.

FIELD OF THE INVENTION

The present invention relates to novel 2,3-aminomutases, such as glutamate 2,3-aminomutases, and include nucleic acids encoding for polypeptides having glutamate 2,3-aminomutase activity and methods of making the same. This invention further relates to methods of using glutamate 2,3-aminomutases to produce β-glutamate.

BACKGROUND/RELATED ART

Although less abundant than the corresponding α-amino acids, β-amino acids occur in nature in both free forms and in peptides. Cardillo and Tomasini, *Chem. Soc. Rev.* 25:77 (1996); Sewald, *Amino Acids* 11:397 (1996). Since β-amino acids are stronger bases and weaker acids than α-amino acid counterparts, peptides that contain a β-amino acid in place of an α-amino acid, have a different skeleton atom pattern, resulting in new properties. For example, various peptides are protease inhibitors because the presence of the β-amino-α-hydroxy acid motif acts as a transition state mimic of peptide hydrolysis.

β-Amino acids are of particular interest in the preparation of medicaments, such as β-lactams. Well-known β-lactam antimicrobial agents include penicillins, cephalosporins, carbapenems, and monobactams. Other examples of medically useful molecules that contain β-amino-α-hydroxy acids include the anti-tumor agent taxol, the anti-bacterial agent, dideoxykanamicin A, bestatin, an immunological response modifier, the kynostatins, which are highly potent human immunodeficiency virus-1 protease inhibitors, and microginin, a tetrapeptide which has anti-hypertensive properties. Accordingly, enantiomerically pure β-amino-α-hydroxy acids are of considerable importance as crucial components of pharmacologically active compounds. Additionally, enantiomerically pure β-amino acids are useful as precursors for preparing various industrial chemicals. Thus, it is desirable to develop new methods for the synthesis of β-amino acids.

Previously, lysine 2,3-aminomutase has been reported to catalyze the conversion of not only lysine but other α-amino acids to the corresponding β-amino acid (see Frey and Ruzicka, U.S. Patent Publication Nos. 2003/0113882 and 2002/0173637, the entire disclosures of which are incorporated herein by reference). By contrast, it is believed that an enzyme which specifically possesses glutamate 2,3-aminomutase activity has not previously been reported.

SUMMARY OF THE INVENTION

It has been discovered for the first time that a gene exists that expresses glutamate 2,3-aminomutase activity, and that the gene product produces β-glutamate from L-glutamate in a reaction requiring S-(5'-adenosyl)-L-methionine, pyridoxal 5'-phosphate and an iron-sulfur cluster. The chemical equation for the transformation of L-glutamate into β-glutamate is:

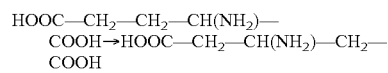

Thus, the present invention provides nucleic acids, including isolated DNA molecules, which encode glutamate 2,3-aminomutase enzymes, polypeptides produced from such nucleic acids and methods of making the nucleic acids and polypeptides. There are further provided methods of producing β-glutamate from glutamate.

Thus, in accordance with one aspect, the invention provides an isolated DNA molecule encoding a polypeptide having glutamate 2,3-aminomutase activity, wherein the DNA molecule comprises a sequence selected from the group consisting of a) a DNA sequence encoding a polypeptide having at least 50% or 60% sequence identity to the amino acid sequence of SEQ ID NOs: 2, 4, 6, 8, 10, 12, 14, 16, or 18 as defined herein; b) a DNA sequence comprising SEQ. ID NO: 1, 3, 5, 7, 9, 11, 13, 15, or 17 as defined herein; and c) a DNA sequence which is degenerate to the sequence of (a) or (b) due to the genetic code. In some embodiments, the DNA sequence encoding a polypeptide has at least 70%, at least 80%, at least 90% or at least 95% sequence identity to the amino acid sequence of SEQ ID NOs: 2, 4, 6, 8, 10, 12, 14, 16, or 18 as defined herein. In other embodiments, there are provided expression vectors comprising the DNA molecule encoding a polypeptide having glutamate 2,3-aminomutase activity. The DNA molecule may be operably linked to one or more control sequences which direct the production of the polypeptide in a host cell.

In another aspect, the invention provides recombinant host cells comprising a DNA molecule as described herein. The recombinant host cell may include the expression vector as described herein. In some embodiments, the recombinant host cells of the invention are prokaryotic cells such as bacterial cells (e.g., *E. coli*).

In still another aspect, the invention provides methods of producing a polypeptide having glutamate 2,3-aminomutase activity comprising culturing a recombinant host cell as described herein. Such methods may further include isolating the polypeptide produced from the recombinant host cell.

In some aspects, the invention provides isolated, recombinant, or isolated and recombinant polypeptides having glutamate 2,3-aminomutase activity and comprising an amino acid sequence selected from the group consisting of (a) SEQ ID NO: 2; (b) SEQ ID NO: 4; (c) SEQ ID NO: 6; (d) SEQ ID NO: 8; (e) SEQ ID NO: 10; (f) SEQ ID NO: 12; (g) SEQ ID NO: 14; (h) SEQ ID NO: 16; (i) SEQ ID NO: 18; (j) a variant having at least 50% or 60% sequence identity to any one of SEQ ID NOs: 2, 4, 6, 8, 10, 12, 14, 16, or 18 as described herein; and (g) a functional fragment having at least 50% or at least 60% sequence identity to any one of SEQ ID NOs: 2, 4, 6, 8, 10, 12, 14, 16, or 18 as described herein. In other embodiments, there are provided isolated, recombinant, or isolated and recombinant polypeptides having glutamate 2,3-aminomutase activity and comprising an iron-sulfur cluster, S-(5'-adenosyl)-L-methionine, and pyridoxal 5'-phosphate. Such polypeptides may have a molecular weight of from about 35 kDa to about 65 kDa, and in some embodiments, from about 40 kDa to about 60 kDa, or about 45 kDa to about 55 kDa.

In another aspect, the invention provides methods of producing β-glutamic acid. The methods include (a) catalyzing the conversion of α-glutamic acid to β-glutamic acid by utilizing a glutamate 2,3-aminomutase as described herein as the catalyst, wherein the glutamate 2,3-aminomutase is isolated, recombinant, or isolated and recombinant; and (b) isolating the β-glutamic acid. Typically, the α-glutamic acid is L-glutamic acid. The method may further include separating the β-glutamic acid from α-glutamic acid by any suitable technique such as by using high performance chromatography. In some embodiments, the method is a continuous process. In others, the glutamate 2,3-aminomutase comprises the following amino acid sequences: CXXXCRXCXR (SEQ ID NO: 19); S(T)GGD(E) (SEQ ID NO: 20), GXXX-PXXXXXXXXXXXK (SEQ ID NO: 21), PXYXXXXKXXXG (SEQ ID NO: 22), and PXXXX-NXXXXXXK (SEQ ID NO: 23).

In some embodiments of methods of producing β-glutamic acid, step (a) further comprises culturing a host cell comprising an expression vector that encodes glutamate 2,3-aminomutase in the presence of α-glutamic acid, wherein the cultured host cell expresses glutamate 2,3-aminomutase; and/or wherein (b) further comprises isolating the β-glutamic acid from the cultured host cells. Thus, the expression vector can include a DNA molecule encoding a polypeptide having glutamate 2,3-aminomutase activity, wherein the DNA molecule comprises a sequence selected from the group consisting of (i) a DNA sequence encoding a polypeptide having at least 50% or at least 60% sequence identity to the amino acid sequence of SEQ ID NOs: 2, 4, 6, 8, 10, 12, 14, 16, or 18 as defined herein; (ii) a DNA sequence comprising SEQ. ID NO: 1, 3, 5, 7, 9, 11, 13, 15, or 17 as defined herein; and (iii) a DNA molecule which is degenerate to the sequence of (i) or (ii). In some embodiments, the DNA sequence encodes a polypeptide having at least 70%, at least 80%, at least 90%, or at least 95% sequence identity to the amino acid sequence of SEQ ID NOs 2, 4, 6, 8, 10, 12, 14, 16, or 18 as defined herein.

In other methods of producing β-glutamic acid, step (a) further comprises incubating glutamic acid in a solution containing purified glutamate 2,3-aminomutase and added cofactors required for glutamate 2,3-aminomutase activity; and/or wherein (b) further comprises isolating β-glutamic acid from the incubation solution. Suitable added cofactors include: (i) at least one of ferrous sulfate or ferric ammonium sulfate; (ii) pyridoxal phosphate; (iii) at least one of cysteine, dehydrolipoic acid, glutathione or dithiothreitol; (iv) S-adenosylmethionine; and (v) sodium dithionite.

In still other methods of producing β-glutamic acid, step (a) further comprises: (i) immobilizing glutamate 2,3-aminomutase on a suitable support; and (ii) activating the glutamate 2,3-aminomutase with cofactors required for glutamate 2,3-aminomutase activity; and (iii) contacting glutamic acid with the immobilized glutamate 2,3-aminomutase to produce the corresponding β-glutamic acid.

DETAILED DESCRIPTION OF THE INVENTION

1. Definitions and Abbreviations

Figure 1:
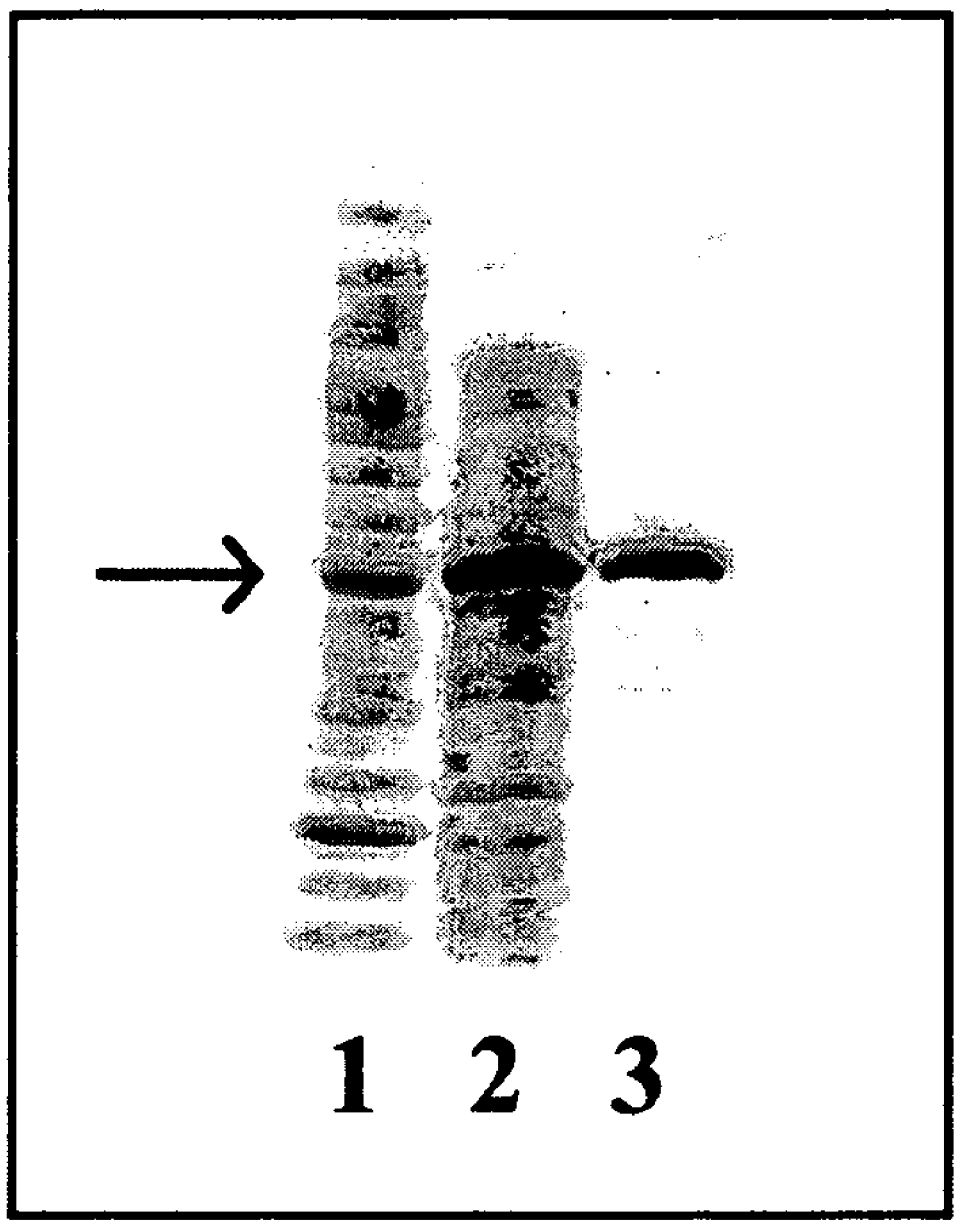
FIG. 1 SDS Polyacrylamide Gel Electrophoresis of Recombinant Produced *C. difficile* Glutamate 2,3-aminomutase in *E. coli* Cell Extract and Purified Form. Lane 1—Protein standards (Benchmark Protein Ladder, Invitrogen) 1 μg each protein, Lane 2—*E. coli* cell extract 30 μg, Lane 3—Purified recombinant *C. difficile* glutamate 2,3-aminomutase 4 μg. Arrow indicates marker for 50,000 MW protein standard.

In the description that follows, a number of terms are utilized extensively. Definitions are herein provided to facilitate understanding of the invention.

Cloning vector. A DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

Complementary DNA (cDNA). Complementary DNA is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule derived from a single mRNA molecule.

Enhancer. A promoter element. An enhancer can increase the efficiency with which a particular gene is transcribed into mRNA irrespective of the distance or orientation of the enhancer relative to the start site of transcription.

Expression. Expression is the process by which a polypeptide is produced from a structural gene. The process involves transcription of the gene into mRNA and the translation of such mRNA into polypeptide(s).

Expression vector. A DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

Lysine 2,3-aminomutase. An enzyme that catalyzes the interconversion of lysine and β-lysine, typically L-lysine to L-β-lysine.

Glutamate 2,3-aminomutase. An enzyme that catalyzes the interconversion of glutamic acid and β-glutamic acid, typically L-glutamic acid to β-glutamic acid.

Promoter. A DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter.

Recombinant host. A recombinant host may be any prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, N.Y. (1989) ["Sambrook"].

Structural gene. A DNA sequence that is transcribed into messenger RNA (mRNA) which is then translated into a sequence of amino acids characteristic of a specific polypeptide (protein).

As used herein, a substantially pure protein means that the desired purified protein is essentially free from contaminating cellular components, as evidenced by a single band following polyacrylamide-sodium dodecyl sulfate gel electrophoresis (SDS-PAGE). The term "substantially pure" is further meant to describe a molecule which is homogeneous by one or more purity or homogeneity characteristics used by those of skill in the art at the present time. For example, a substantially pure glutamate 2,3-aminomutase will show constant and reproducible characteristics within standard experimental deviations for parameters such as the following: molecular weight, chromatographic migration, amino acid composition, amino acid sequence, blocked or unblocked N-terminus, HPLC elution profile, biological activity such as $V_{max}$, and other such parameters. In some embodiments, a substantially pure protein of the invention will be at least 90% pure as judged by SDS-PAGE and/or other parameters. The term, however, is not meant to exclude artificial or synthetic mixtures of glutamate 2,3-aminomutase with other compounds. In addition, the term is not meant to exclude glutamate 2,3-aminomutase fusion proteins isolated from a recombinant host.

Abbreviations: EPPS, N-[2-hydroxyethyl-piperazine-N'-(3-propanesulfonic acid)]; dNTP, a 2'-deoxyribonucleotide-5'-triphosphate; DTT, dithiothreitol; EDTA, ethylenediamine tetraacetic acid; EPR, electron paramagnetic resonance; HPLC, high performance liquid chromatography; IPTG, isopropyl-β-D-thiogalactopyranoside; PCR, polymerase chain reaction; PITC, phenylisothiocyanate; PMSF, phenylmethanesulfonyl fluoride; Tris, tris(hydroxymethyl)aminomethane.

2. Isolation of a DNA Molecule that Encodes the *Clostridium* Glutamate 2,3-Aminomutase Although the existence of the clostridial lysine 2,3-aminomutase has been known for over 35 years, there is no report in the scientific literature on the isolation of the gene encoding glutamate 2,3-aminomutase. Now, for the first time and as described herein, DNA molecules encoding the clostridial glutamate 2,3-aminomutase gene have been isolated from the chromosomal DNA of *Clostridium difficile*. The nucleotide and predicted amino acid sequences of clostridial glutamate 2,3-aminomutase (SEQ ID NOs: 1 and 2) isolated from the genomic database are:

```
SEQ ID NO:1
ATGAATGAACAAACTAGAATATCCTTAGAGAGAGCTGCTGAATTAAAATCAAAAATTGAT      60

GATTATATTCAGGCTAGAAAAACGATTAACAGAGGTCTTGAAAAAGAAGAAGAGATAAAT     120

AAACGAAAACAGAAAATATTAAGTATCTTAAATGGAACTGAAGAGGATTGGAATAACTAC     180

AAATGGCAATTATCAAATAGAATAACAGATGTAGATACTTTATCAAAAATTATAACTCTA     240

ACTAAAAAAGAAAAAGAATATATAAAAGAGGTTGGTACTCAATTTAGATGGGCAATATCT     300

CCATATTATTTGAGTCTTATAGACCCAGAAGATATATGTGACCCAATAAAATTACTGTCT     360

ATACCAACACATATAGAGTTGGAAGATGAACAAGAAGATTTGGACCCAATGGGAGAAGAG     420

TATACAAACCCAGCAGGATGTATAACTAGAAGATACCCGGATAGATTAATAATAAATGTA     480

ACAAATGAGTGTGCTATGTATTGTAGACACTGTCAGAGAAGAAGAAATATTGGACAACAA     540

GATTCTCATAAGTCAAAAGCTATTATCCAAGAATCTATAGACTATATCAGAGAAAATGAA     600
```

```
                                               -continued
GAAATAAGAGATGTACTAGTAACTGGTGGAGATGCTCTTACATTAAAAGATGATTATTTA    660

GAGTGGATTCTTAGCCAACTTAAAGAGATACCACATGTTGATTATGTTAGATTAGGTACT    720

AGGACTCTTGTTACAATGCCACAAAGAATTACAGATGAATTTTGCAATATGCTAAAAAAA    780

TATCACCCTATATATATAAATACTCATTTTAATCATCCAATGGAAATAACTAAGGAATCT    840

AAAGAAGCTTGTGAAAAGTTAGCAAATGCAGGAGTTCCATTAGGAAATCAGGCAGTATTA    900

TTAAATGGAATAAATAATGATAAATTTGTAATGAGATGTTTAAATCAAGAATTACTGAAA    960

ATAAGAGTAAAACCTTATTATATATTCCAAAGTAAACATGTAAAGGGAACAAAACATTTC   1020

AATACATCAGTAGATGATGGTCTTGAAATCATGGAGTATTTAAGAGGATATACATCAGGA   1080

ATGGCTATACCAACATATATAGTAAATGCTCCAAAAGGAGGAGGAAAGACTCCTTTGCTT   1140

CCTCAATACCTTGTATCAAAAGGAACAGATTACGTTATGCTTAGAACATGGGAAGGAAAA   1200

GTTATAAAAATGGAAGATGAACCTGCTGTAGATATAAAGAAACTTATAAAAGAACAAGCA   1260

CAGGATTAA                                                     1269
```

```
SEQ ID NO:2
MNEQTRISLE  RAAELKSKID  DYIQARKTIN  RGLEKEEEIN    50
KRKQKILSIL

NGTEEDWNNY  KWQLSNRITD  VDTLSKIITL  TKKEKEYIKE   100
VGTQFRWAIS

PYYLSLIDPE  DICDPIKLLS  IPTHIELEDE  QEDLDPMGEE   150
YTNPAGCITR

RYPDRLIINV  TNECAMYCRH  CQRRRNIGQQ  DSHKSKAIIQ   200
ESIDYIRENE

EIRDVLVTGG  DALTLKDDYL  EWILSQLKEI  PHVDYVRLGT   250
RTLVTMPQRI

TDEFCNMLKK  YHPIYINTHF  NHPMEITKES  KEACEKLANA   300
GVPLGNQAVL

LNGINNDKFV  MRCLNQELLK  IRVKPYYIFQ  SKHVKGTKHF   350
NTSVDDGLEI

MEYLRGYTSG  MAIPTYIVNA  PKGGGKTPLL  PQYLVSKGTD   400
YVMLRTWEGK

VIKMEDEPAV  DIKKLIKEQA  QD                      422
```

DNA molecules encoding the clostridial glutamate 2,3-aminomutase gene can be obtained by screening cDNA or genomic libraries with polynucleotide probes having nucleotide sequences based upon SEQ ID NO:1. For example, a suitable library can be prepared by obtaining genomic DNA from *Clostridium difficile* and constructing a library according to standard methods. See, for example, Ausubel et al. (eds.), SHORT PROTOCOLS IN MOLECULAR BIOLOGY, 5th Edition, pages 2-1 to 2-13 and 5-1 to 5-6 (John Wiley & Sons, Inc. 2002).

Alternatively, the clostridial glutamate 2,3-aminomutase gene can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., *Gene* 60:115 (1987); and Ausubel et al. (eds.), SHORT PROTOCOLS IN MOLECULAR BIOLOGY, 5th Edition, John Wiley & Sons, Inc. (2002). Established techniques using the polyrnerase chain reaction provide the ability to synthesize DNA molecules at least 2 kilobases in length. Adang et al., *Plant Molec. Biol.* 21:1131 (1993); Bambot et al., *PCR Methods and Applications* 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993); Holowachuk et al., *PCR Methods Appl.* 4:299 (1995).

Included in the invention are also DNA molecules in which the nucleotide sequences are degenerate, because of the genetic code, to the nucleotide sequences shown as SEQ ID NOs: 1, 3, 5, 7, 9, 11, 13, 15, and 17. A sequential grouping of three nucleotides, a "codon", codes for one amino acid. Since there are 64 possible codons, but only 20 natural amino acids, most amino acids are coded for by more than one codon. This natural "degeneracy", or "redundancy", of the genetic code is well known in the art. It will thus be appreciated that the DNA sequences described herein and shown in the Sequence Listing are only examples within a large but definite group of DNA sequences which will encode the polypeptides described herein. Exemplary degenerate DNA sequences include but are not limited to SEQ ID NOs: 28, 29, 30, and 31, which are presented in Example 3 and are degenerate to SEQ ID NOs: 3, 5, 7, and 9, respectively.

Variants of glutamate 2,3-aminomutase can be produced that contain one or more conservative or non-conservative amino acid changes, compared with the native enzyme, so long as glutamate 2,3-aminomutase activity is retained. Typically variants have at least 50%, at least 60%, at least 70%, at least 80%, or at least 90% amino acid sequence identity compared to the original sequences such as any one of SEQ ID NOs: 2, 4, 6, 8, 10, 12, 14, 16, or 18. In some embodiments, high sequence identity variants are provided in which the amino acid sequence identity of the variant to the glutamate 2,3-aminomutase is at least 95%, at least 96%, at least 97%, at least 98% or even at least 99%. In other embodiments, glutamate 2,3-aminomutase variants include 1, 2, 3, 4, 5, 6, 7, 8, 9, 10, or more conservative or nonconservative amino acid substitutions such as 15, 20, 25, 30, or even 40 amino acid substitutions so long as glutamate 2,3-aminomutase activity is retained. The ability of variants of glutamate 2,3-aminomutase to convert L-glutamate to β-glutamate can be determined using a standard enzyme activity assay, such as the assay described herein.

Conservative variants can be obtained that contain one or more amino acid substitutions of, e.g., SEQ ID NO:2, in which an alkyl amino acid is substituted for an alkyl amino acid in the glutamate 2,3-aminomutase amino acid sequence, an aromatic amino acid is substituted for an aromatic amino acid in glutamate 2,3-aminomutase amino acid sequence, a sulfur-containing amino acid is substituted for a sulfur-containing amino acid in the glutamate 2,3-aminomutase amino acid sequence, a hydroxy-containing amino acid is substituted for a hydroxy-containing amino acid in the glutamate 2,3-aminomutase amino acid sequence, an acidic amino acid is substituted for an acidic amino acid in the glutamate 2,3-aminomutase amino acid sequence, a basic amino acid is substituted for a basic amino acid in the glutamate 2,3-aminomutase amino acid sequence, or a dibasic monocarboxylic amino acid is substituted for a dibasic monocarboxylic amino acid in the glutamate 2,3-aminomutase amino acid sequence.

Among the common amino acids, for example, a "conservative amino acid substitution" is illustrated by a substitution among amino acids within each of the following groups: (1) glycine, alanine, (2) valine, leucine, and isoleucine, (3) phenylalanine, tyrosine, and tryptophan, (4) cysteine and methionine, (5) serine and threonine, (6) aspartate and glutamate, (7) glutamine and asparagine, and (8) lysine, arginine and histidine.

Conservative amino acid changes in, e.g., the clostridial glutamate 2,3-aminomutase, can be introduced by substituting appropriate nucleotides for the nucleotides recited in SEQ ID NO:1. Such "conservative amino acid" variants can be obtained, for example, by oligonucleotide-directed mutagenesis, linker-scanning mutagenesis, mutagenesis using the polymerase chain reaction, and the like. Ausubel et al., supra; Ausubel et al. (eds.), SHORT PROTOCOLS IN MOLECULAR BIOLOGY, 5th Edition, John Wiley & Sons, Inc. (2002). Also see generally, McPherson (ed.), DIRECTED MUTAGENESIS: A PRACTICAL APPROACH, IRL Press (1991). Similarly, conservative amino acid changes may be made in the glutamate 2,3-aminomutase from other species by substituting appropriate nucleotides in the sequences recited in SEQ ID NOs:3, 5, 7, 9, 11, 13, 15, and 17.

Glutamate 2, 3-aminomutase variants that contain one or more non-conservative amino acid substitutions, such as those based on glutamate 2,3-aminomutase having any one of SEQ ID NOs: 2, 4, 6, 8, 10, 12, 14, 16, or 18, and that retain the ability to produce β-glutamic acid from α-glutamic acid can also be produced and used as disclosed herein. Non-conservative amino acid substitutions are known in the art and include, without limitation, leucine for aspartate or valine for threonine. Non-conservative variants can also include amino acid insertions as compared to the native sequence such as, without limitation, insertion of methionine. As will be appreciated by the skilled artisan, the same methods used for generating conservative variants may be adapted and used to produce nonconservative variants.

In addition, routine deletion analyses of DNA molecules can be performed to obtain "functional fragments" of the clostridial glutamate 2,3-aminomutase or other glutamate 2,3-aminomutases. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for glutamate 2,3-aminomutase enzyme activity. One alternative to exonuclease digestion is to use oligonucleotide-directed mutagenesis to introduce deletions or stop codons to specify production of a desired fragment. Alternatively, particular fragments of the clostridial glutamate 2,3-aminomutase gene can be synthesized using the polymerase chain reaction. Standard techniques for functional analysis of proteins are described by, for example, Treuter et al., Molec. Gen. Genet. 240:113 (1993); Content et al., "Expression and preliminary deletion analysis of the 42 kDa 2-5A synthetase induced by human interferon," in BIOLOGICAL INTERFERON SYSTEMS, PROCEEDINGS OF ISIR-TNO MEETING ON INTERFERON SYSTEMS, Cantell (ed.), pages 65-72 (Nijhoff 1987); Herschman, "The EGF Receptor," in CONTROL OF ANIMAL CELL PROLIFERATION, Vol. 1, Boynton et al., (eds.) pages 169-199 (Academic Press 1985); Coumailleau et al., J. Biol. Chem. 270:29270 (1995); Fukunaga et al., J Biol. Chem. 270:25291 (1995); Yamaguchi et al., Biochem. Pharmacol. 50:1295 (1995); and Meisel et al., Plant Molec. Biol. 30:1 (1996). Similar deletions may be carried out on SEQ ID NOs: 3, 5, 7, 9, 11, 13, 15, and 17. In some embodiments the functional fragment retains at least 50% or at least 60% of the amino acids of the native sequence. In others the functional fragment retains at least 70%, at least 80%, at least 90%, at least 95%, at least 98% or at least 99% of the amino acids of the native sequence.

The present invention also contemplates functional fragments of glutamate 2,3-aminomutases having the sequences disclosed herein that have conservative and non-conservative amino acid changes.

3. Expression of Cloned Glutamate 2,3-Aminomutase

To express the polypeptide encoded by a glutamate 2,3-aminomutase gene, the DNA sequence encoding the enzyme must be operably linked to regulatory sequences that control transcriptional expression in an expression vector and then, introduced into either a prokaryotic or eukaryotic host cell. In addition to transcriptional regulatory sequences, such as promoters and enhancers, expression vectors can include translational regulatory sequences and a marker gene which is suitable for selection of cells that carry the expression vector.

Suitable promoters for expression in a prokaryotic host can be repressible, constitutive, or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacλpr, phoA, gal, trc and lacZ promoters of E. coli, the α-amylase and the $\sigma^{28}$-specific promoters of B. subtilis, the promoters of the bacteriophages of Bacillus, Streptomyces promoters, the int promoter of bacteriophage lambda, the bla promoter of the β-lactamase gene of pBR322, and the CAT promoter of the chloramphenicol acetyl transferase gene. Prokaryotic promoters are reviewed by Glick, J. Ind. Microbiol. 1:277 (1987); Watson et al., MOLECULAR BIOLOGY OF THE GENE, 4th Ed., Benjamin Cummins (1987); Ausubel et al., supra, and Sambrook et al., supra.

Preferred prokaryotic hosts include E. coli, Clostridium, and Haemophilus. Suitable strains of E. coli include DH1, DH4α, DH5, DH5α, DH5αF', DH5αMCR, DH10B, DH10B/p3, DH11S, C600, HB101, JM101, JM105, JM109, JM110, K38, RR1, Y1088, Y1089, CSH18, ER1451, BL21 (DE3), BL21(DE3)plysS, BLR(DE3), BLR(DE3)plysS, and ER1647 (see, for example, Brown (Ed.), MOLECULAR BIOLOGY LABFAX, Academic Press (1991)). Suitable Clostridia include Clostridium subterminale SB4 (ATCC No. 29748) and Clostridium acetobutylicum (ATCC No. 824), while a suitable Haemophilus host is Haemophilus influenza (ATCC No. 33391).

An alternative host is Bacillus subtilis, including such strains as BR151, YB886, MI119, MI120, and B170. See, for example, Hardy, "*Bacillus* Cloning Methods," in DNA CLONING: A PRACTICAL APPROACH, Glover (Ed.), IRL Press (1985).

Methods for expressing proteins in prokaryotic hosts are well-known to those of skill in the art. See, for example, Williams et al., "Expression of foreign proteins in *E. coli* using plasmid vectors and purification of specific polyclonal antibodies," in DNA CLONING 2: EXPRESSION SYSTEMS, 2nd Edition, Glover et al. (eds.), pages 15-58 (Oxford University Press 1995). Also see, Ward et al., "Genetic Manipulation and Expression of Antibodies," in MONOCLONAL ANTIBODIES: PRINCIPLES AND APPLICATIONS, pages 137-185 (Wiley-Liss, Inc. 1995); and Georgiou, "Expression of Proteins in Bacteria," in PROTEIN ENGINEERING: PRINCIPLES AND PRACTICE, Cleland et al. (eds.), pages 101-127 (John Wiley & Sons, Inc. 1996).

An expression vector can be introduced into bacterial host cells using a variety of techniques including calcium chloride transformation, electroporation, and the like. See, for example, Ausubel et al. (eds.), SHORT PROTOCOLS IN MOLECULAR BIOLOGY, 3rd Edition, pages 1-1 to 1-24 (John Wiley & Sons, Inc. 1995).

To maximize recovery of functional glutamate 2,3-aminomutase from recombinant hosts, transformed cells should be cultured under anaerobic conditions or under air without oxygen enrichment. Methods for culturing recombinant clostridia are well-known to those of skill in the art. See, for example, Mermelstein et al., *Ann. N.Y. Acad. Sci.* 721:54 (1994); Walter et al., *Ann. N.Y. Acad. Sci.* 721:69. (1994). Additionally, anaerobic culturing of bacteria is well known in the art. See, for example, Smith and Neidhardt, *J. Bacteriol.* 154:336 (1983).

4. Isolation of Cloned Glutamate 2,3-Aminomutase and Production of Anti-Glutamate 2,3-Aminomutase Antibodies A. Isolation of Recombinant Glutamate 2,3-Aminomutase General methods for recovering protein produced by a bacterial system are provided by, for example, Grisshammer et al., "Purification of over-produced proteins from *E. coli* cells," in DNA CLONING 2: EXPRESSION SYSTEMS, 2nd Edition, Glover et al. (eds.), pages 59-92 (Oxford University Press 1995); Georgiou, "Expression of Proteins in Bacteria," in PROTEIN ENGINEERING: PRINCIPLES AND PRACTICE, Cleland et al. (eds.), pages 101-127 (Wiley-Liss, Inc. 1996).

Recombinant glutamate 2,3-aminomutases can be purified from bacteria using standard methods similar to those that have been used to purify *Clostridium subterminale* SB4 lysine 2,3-aminomutase. In general, several precautions can be taken to ensure high enzyme activity of the purified protein. As discussed above, for example, enzyme activity will generally be maximal when host cells are cultured under anaerobic conditions or conditions which restrict the presence of oxygen, Frey and Reed, *Adv. Enzymol.* 66:1 (1993), although rigid anaerobic conditions are not required in culturing host cells and culture conditions in air have been successful. Oxygen should also be excluded during all purification steps. Purification under anaerobic conditions protects metal cofactors from being irreversibly degraded and allows maximal activity to be attained upon activation with S-adenosylmethionine. However, variants of glutamate 2,3-aminomutase may be stable in air and even function under aerobic conditions.

Lysine 2,3-aminomutase activity can be determined as detailed in the examples.

B. Preparation of Anti-Glutamate 2,3-Aminomutase Antibodies and Fragments Thereof Antibodies to glutamate 2,3-aminomutase can be obtained, for example, using the product of an expression vector as an antigen. Polyclonal antibodies to recombinant enzyme can be prepared using methods well-known to those of skill in the art. See, for example, Green et al., "Production of Polyclonal Antisera," in IMMUNOCHEMICAL PROTOCOLS (Manson, ed.), pages 1-5 (Humana Press 1992). Also see, Williams et al., "Expression of foreign proteins in *E. coli* using plasmid vectors and purification of specific polyclonal antibodies," in DNA CLONING 2: EXPRESSION SYSTEMS, 2nd Edition, Glover et al. (eds.), pages 15-58 (Oxford University Press 1995).

Alternatively, an anti-glutamate 2,3-aminomutase antibody can be derived from a rodent monoclonal antibody (MAb). Rodent monoclonal antibodies to specific antigens may be obtained by methods known to those skilled in the art. See, for example, Kohler et al., *Nature* 256:495 (1975), and Coligan et al (eds.), CURRENT PROTOCOLS IN IMMUNOLOGY, VOL. 1, pages 2.5.1-2.6.7 (John Wiley & Sons 1991) ["Coligan"]. Also see, Picksley et al., "Production of monoclonal antibodies against proteins expressed in *E. coli*," in DNA CLONING 2: EXPRESSION SYSTEMS, 2nd Edition, Glover et al. (eds.), pages 93-122 (Oxford University Press 1995).

Briefly, monoclonal antibodies (MAbs) can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

For particular uses, it may be desirable to prepare fragments of anti-glutamate 2,3-aminomutase antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein. Also, see Nisonoff et al., *Arch Biochem. Biophys.* 89:230 (1960); Porter, *Biochem. J.* 73:119 (1959), Edelman et al., in METHODS IN ENZYMOLOGY VOL. 1, page 422 (Academic Press 1967), and Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, for example, Sandhu, *Crit. Rev. Biotech.* 12:437 (1992).

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2:97 (1991). Also see Bird et al., *Science* 242:423 (1988), Ladner et al., U.S. Pat. No. 4,946,778, Pack et al., *Bio/Technology* 11:1271 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

5. Isolation of Additional Glutamate 2,3-Aminomutase Genes

The nucleotide sequences of the clostridial glutamate 2,3-aminomutase gene and antibodies to the enzyme provide a means to isolate additional glutamate 2,3-aminomutase genes. Such genes can encode enzymes from various organisms, including but not limited to *Thermoanaerobacter tengcongensis, Desulfitobacterium hafniense* DCB-2, *Moorella thermoacetica, Syntrophomonas wolfei* (str. *Goettingen*), *Alkaliphilus metalliredigenes* QYMF, *Caldicellulosiruptor saccharolyticus* DSM 8903, *Desulfotomaculum reducens* MI-1, and *Carboxydothermus hydrogenoformans* Z-2901.

For example, the amino acid sequence of the clostridial glutamate 2,3-aminomutase was used to identify related enzymes in various bacteria. Sequence analyses revealed a sequence identity of about 50-60% between the amino acid sequence of the clostridial enzyme and the gene products of SEQ ID NOs: 3, 5, 7, 9, 11, 13, 15, and 17.

The nucleotide and amino acid sequences (SEQ ID NOs:3 and 4) of the *Thermoanaerobacter tengcongensis* polypeptide are:

```
   1 atgagcagca cgggttcact cacagtggag gaaaaaagga aaatagcact ccaaagagcg 61 gaagagttaa aaaagaagat agagccatac ttgagagcat ctgaaaaaat agagacgggc 121 tttaagttat cagaaaaatt tagagaaaac aaggagaaaa ttaaaaactt atttggagca 181 acagaagagg aatggaatga ttggcgatgg cagataagaa atcgtataag tgatgttgaa 241 actctcaaaa agattgtaaa cctttctgag gaggaaattg aaaacataaa gagggtaagt 301 actcgctaca gatgggcaat ttcaccatac tatgcttctt taatggatcc ggataatcct 361 ttctgtccta ttcgaatgag agctatccca agtattaagg aacttacaga taaatatgga 421 gttccagacc cgatggcaga agaatatact tctcccgctc ctttaataac acgtcgttat 481 cctgatcgac tgattataaa cgtaacaaat caatgtggca tgttctgtag acattgtcag 541 aggagacgca acataggaga agtggattat cctgcaaaac acgaagacat agaagcggca 601 ttagaatata ttcgaaataa tccagaaatt agagatgtgc tgataacagg gggagaccct 661 ctcactcttg aggatgaaaa aatcgactgg attttgtcag aattagataa aattccacat 721 gtagaaataa aacgaatagg gacggctgcc ccagtgactt ttccacagag aattaccgat 781 gaattatgca agattttaac aaaacatctg cctctgtaca ttaataccca gtttaatcat 841 ccaaaagaag ttactgaaga agcaaaagag gcttgcttta aattagcaag agctggggtg 901 gcattaggaa atcaagcagt gcttttaaaa gggataaata atgaccctca tgttatgaaa 961 aagttaaacc acgaattact tagaattatg gttaaacctt actacatttt ccatgcgaaa 1021 tctgttcaag ggactaccca ttttgttact acagttcaag atggattaga gattatggaa 1081 caacttcgcg gttatacttc agggcttgcc attccgtggt atataatcaa tgcacctgaa
```

-continued

```
1141 gggcatggga agactcctat tgtgcctcag tatctcctta tggttgggaa agaatatgtt
1201 cttataagaa attgggaagg aaaagttttt gaatatccga atggcttccc tgacgattaa 1 msstgsltve ekrkialqra eelkkkiepy lrasekietg fklsekfren kekiknlfga
  61 teeewndwrw qirnrisdve tlkkivnlse eeienikrvs tryrwaispy yaslmdpdnp
 121 fcpirmraip sikeltdkyg vpdpmaeeyt spaplitrry pdrliinvtn qcgmfcrhcq
 181 rrrnigevdy pakhedieaa leyirnnpei rdvlitggdp ltledekidw ilseldkiph
 241 veikrigtaa pvtfpqritd elckiltkhl plyintqfnh pkevteeake acfklaragv
 301 algnqavllk ginndphvmk klnhellrim vkpyyifhak svqgtthfvt tvqdgleime
 361 qlrgytsgla ipwyiinape ghgktpivpq yllmvgkeyv lirnwegkvf eypngfpdd
```

The nucleotide and amino acid sequences (SEQ ID NOs:5 and 6) of the *Desulfitobacterium hafniense* DCB-2 polypeptide are:

```
   1 atggcaatag aatttctacc ccctaaccca agacaggctt cacaagcaag agctttggaa
  61 ttaaaacaaa aagttcaatc ctacaacaaa cgcaaagaaa cgattccctg cggccttgcc
 121 ttaagcgaag aatttaatga aaaccgagac tttatactgg atcagttaga tgctgacctg
 181 gagcattggc aggattggaa gtggcagctt aaaaaccgta ttcaggatgc tgaaaacttg
 241 agcaccctgc ttcccctgac ccccaagcaa agacatgaaa tcaacgaggt gggcaaggct
 301 taccgttggg ctgtttcacc ctattattta agcctgatcg ataaagatga tcctcaggat
 361 cccatccgtc tgcaaagtct cccctctgtg aagagatcc tcgacgattc cggagaagca
 421 gatcccatgg gagaagagta tacatcccct gcgccttgca tcacacgtcg ttacccggat
 481 cgcctcatta ttaatgtaac caatttgtgt gctatgtatt gcaggcactg ccaacgccga
 541 cggaatatcg gggaaattga cctccatgaa acccgtgcta acctggaggc cgccctggat
 601 tatatacgct ccaatccaga gattcgggat gtgctagtca ccggtggcga tgctctcctt
 661 ctcagcgatc aaatgctgga ctggttattg ggagaattgc atgaaattaa gcatgtggag
 721 atcaaacgta tcggcacccg ggttcccgtc actctgccca tgcgcattac cgatgagctc
 781 tgcgctattc ttgaaaaata tccaccccct tatatcaata ctcaattcaa tcatccccaa
 841 gaggtgaccg aggagaccaa gaaagctgct gatcgcttaa tcaaagcggg agtcatctta
 901 ggcaaccaag cagttcttct taaggaatc aatgaccaac agagattat gaaacgcctt
 961 aaccaagaac ttcttaaaat tcgcgttcgc ccctactata ttttccatgc caaaatgtt
1021 aaaggcacga gccactttat tccccgcatt caggacgggt taaggattat ggaaaacttg
1081 cgcggctaca cctctggttt ggccattccg acctatatta ttaatgcccc gggaggcggt
1141 ggcaaaaccc ccatcttacc acagtacctt atttccctaa cgatgaaga agcagtcatc
1201 agaacctggg aaggtaaggt tgtgcattat cctaatcatt aa 1 maieflppnp rqasqarale lkqkvqsynk rketipcgla lseefnenrd fildqldadl
  61 ehwqdwkwql knriqdaenl stllpltpkq rheinevgka yrwavspyyl slidkddpqd
 121 pirlqslpsv eeilddsgea dpmgeeytsp apcitrrypd rliinvtnlc amycrhcqrr
 181 rnigeidlhe tranleaald yirsnpeird vlvtggdall lsdqmldwll gelheikhve
 241 ikrigtrvpv tlpmritdel cailekyppl yintqfnhpq evteetkkaa drlikagvil
```

-continued

```
301 gnqavllkgi ndqpeimkrl nqellkirvr pyyifhaknv kgtshfipri qdglrimenl 361 rgytsglaip tyiinapggg gktpilpqyl islndeeavi rtwegkvvhy pnh
```

The nucleotide and amino acid sequences (SEQ ID NOs:7 and 8) of the *Moorella thermoacetica* polypeptide (ATCC 39073) are:

```
   1 atgggaaggg aagctaaaag ggaaattgct cttgaccggg cagccgaatt gaaagccagg 61 attgtcgatt acctggaaga aagggagaag atcgccagcg gcctggaggc ggcagccgag 121 atcgaagcca gcaagcaacg tatcctggct tactttggcg ccggggaagc cgagtggcag 181 gactggcgct ggcagttgac ccaccgtatc acctcggtgg caaccctggc ggaactgatt 241 cccctgacag aagctgaaaa ggaagccata ctaaaggtag aacgtaccta tcgctgggcg 301 gtttctcctt actacctgag cctgatggga ccggaacctg attgccccat ccggcgccag 361 gctctgccca gtgccgccga actggaggat aaccatggcg tcctggaccc catggatgaa 421 gagttgacct ccccggcgcc ggctattacc cgccgttatc cggatcgttt gattatcaac 481 gtaaccaacc agtgtgctat gtactgtcgt cactgccagc ggcgtcgcaa tatcggtgaa 541 gtcgaccgca gtcgcagccg ccgggaactg gagcaggccc tccagtatat ccgccagaat 601 gaagagatcc gcgatgtcct gatcactggc ggtgacgccc tgatgctcag cgatgccatg 661 atcgactggt tgttgacgga actcgataat atcccccacg tagaaattaa gcgcctgggc 721 accaggtgc cggtcactat gccccagcgg attaccccgg agctgtgccg ggttctggcc 781 aagcacccgc ccatctatct caatacccag ttcaaccacc cccgggaggt taccgcggcc 841 gccaagaag cctgcgatcg cctggtccag gccggggtgg tcctcggcaa ccaggcggtt 901 ttgttaaagg gcgtcaacaa ccatcccttt gtgatgcgta aattaaacca ggaactcttg 961 aaaataaggg tacggcccta ctatatcttc cacgccaagc cggtgaaggg gaccacccac 1021 tttattacct ccattgagga gggcgtggag atcatggata gctccgggg ctataccctcc 1081 ggcctggccg tgcctaccta tataatcaat gccccccacg gtctgggcaa gacccccatc 1141 ttgccacagt atgtaatcgc ccgtaatgat caccaggtga tcctgaggac ctgggagaag 1201 cggattattt tttactccaa cctgggacgc cagaaggaac aggcctaa 1 mgreakreia ldraaelkar ivdyleerek iasgleaaae ieaskqrila yfgageaewq 61 dwrwqlthri tsvatlaeli plteaekeai lkvertyrwa vspyylslmg pepdcpirrq 121 alpsaaeled nhgvldpmde eltspapait rrypdrliin vtnqcamycr hcqrrrnige 181 vdrsrsrrel eqalqyirqn eeirdvlitg gdalmlsdam idwllteldn iphveikrlg 241 trvpvtmpqr itpelcrvla khppiylntq fnhprevtaa akeacdrlvq agvvlgnqav 301 llkgvnnhpf vmrklnqell kirvrpyyif hakpvkgtth fitsieegve imdklrgyts 361 glavptyiin aphglgktpi lpqyviarnd hqvilrtwek riifysnlgr qkeqa
```

The nucleotide and amino acid sequences (SEQ ID NOs:9 and 10) of the *Syntrophomonas wolfei* (str. *Goettingen*) polypeptide are:

```
   1 ttgttgttaa gagaagattt gataaacgaa gaaattcggg agatgaaacg cgaagtatct
  61 ttacgtaggg cggatgagct caaacaggaa atttctgact atcttgatat cgaatctact
 121 attgaaacgg gaatgcgatt acatgaacgt aatctgcaca ataaggaaca tatcctgaaa
 181 tactttgagg tcagcgagaa tgattgggat aattgggcct ggcaaatgag gaatcgcatc
 241 aatgatggaa atgtgctggc ttccattctg ggcttaaatg aattcgaagt gcagacaatt
 301 aaaagggttt ccaaaaaagt ccgctgggct atttctccct attatcttag tttaatcgat
 361 tttgaaaatt acgcggcgtc acccatttac aagcagtctg tccccagtct gcatgaaata
 421 atagaatgta agggtgagga tgaccccatg ggagaagaga tgagtagtcc tgctccccgt
 481 attacacgtc gttatcccga ccgacttata atcaatgtta ccaatcaatg tgctatgtac
 541 tgccgccatt gtcagcgccg tagaaatttc ggtgaaactg ataaccatgc cgcccataaa
 601 gacctggaag ctgccctgca gtacattaaa aacaattctg aaatacggga tgttcttatt
 661 accggtgggg atgctctaat gcttagcgat cgtacacttg actggttact gggagaactc
 721 gatgccattt cacatgttga aattaagcgt attggtacca ggacaccggt aacacttcca
 781 caaagaataa ccgccaatct ttgtgcagtg ctaaaaaggc atacacccat atatattaat
 841 acccaattta attcaccgct ggaagttact ccggaagcca acaggcctg tgatcggctt
 901 attgaagcag gagtagtatt gggtaaccag gctgttctgc taagggaat caacgataat
 961 gtccatgtta tgaaaaaact taaccaggag ttgctgaaaa tccgggttcg cccctactat
1021 ttattccagg ccaaagaggt aaaaggaact acccattta ttagcccggt caataccggc
1081 ctggatatta tgaagcattt acggggctat acttctggcc tggccatccc cacttatgtt
1141 atcaacgcac caggaggtta cggtaaaact ccagttaacc cggaatatgt actggatatt
1201 aatgaaaatg aagttataat tagtacctgg cagggtaaaa cttttaacta tcccccatcgt
1261 aacaattag 1 mllredline eiremkrevs lrradelkqe isdyldiest ietgmrlher nlhnkehilk
  61 yfevsendwd nwawqmrnri ndgnvlasil glnefevqti krvskkvrwa ispyylslid
 121 fenyaaspiy kqsvpslhei ieckgeddpm geemsspapr itrrypdrli invtnqcamy
 181 crhcqrrrnf getdnhaahk dleaalqyik nnseirdvli tggdalmlsd rtldwllgel
 241 daishveikr igtrtpvtlp qritanlcav lkrhtpiyin tqfnsplevt peakqacdrl
 301 ieagvvlgnq avllkgindn vhvmkklnqe llkirvrpyy lfqakevkgt thfispvntg
 361 ldimkhlrgy tsglaiptyv inapggygkt pvnpeyvldi neneviistw qgktfnyphr
 421 nn
```

The nucleotide and amino acid sequences (SEQ ID NOs:11 and 12) of the *Alkaliphilus metalliredigenes* QYMF polypeptide are:

```
   1 gtgaatcata ccgatacaac aaacagtcgt caaatttcaa tcgatcgagc taagcatcta
  61 aaattaacca tacaggatta cttagagata aaagacctca ttcccaaagg attatctcgt
 121 caagtggaaa tcgaagcgaa aaagcaaaaa atcctatccc attttggtgc tactgaagat
 181 aattggaatg attggcaatg gcaattaagc aatcgaatat ctgatgttga taccttaaca
 241 aaaataatta agttagatga taaagaaatt gaagatataa aaaaagtagg acaagaattt
 301 agatggtcag tatcacccta ttacaccact ctaattgatg acaataataa gtattgtcca
 361 attaaactta tggctatacc ccatggctac gaaattgcca ataccaaagg agatacagat
 421 ccaatggcag aagagttcac gaatcctgct ggatcaatta cacgccgcta tcccgatcga
 481 ttaattatta atgtaaccaa tgaatgtgca atgtactgta gacattgtca acgaagaaga
 541 aacataggaa ctaatgatct ccatacatcc cgagaggttt acaagaatc gattgattat
 601 attcgtgata atcctgaaat ccgggatgta ttaattactg gtggcgacgc attgacccttt
 661 tctaatagta tgcttgattg gttattggga gaattacatg caattccatc cgtagactat
 721 attagattgg gctctcgtac attggtcact atgccccaaa gaatcacaga taagttgatc
 781 aatattctta aaaagtaccc acctattttt attaatacc actttaatca ccccatggag
 841 attacagaag agtccaaggc agcatgtgat agattatcca atgcgggcat tccattaggt
 901 aaccaagcag ttctccttaa tggcattaat aataataagt ttgtcatgag attacttaat
 961 cacgaactat taaaatgtcg tgttcgtcct tactatatat tccatgcgaa acatgttatt
1021 ggcactagtc attttaacac gtctgttgat gatggcatcg aaatcatgga gtacttaaga
1081 ggctacacat ctggtatggc aattccaacc tatatcatta tgcccctgg cggaaaagga
1141 aaaactccta tacttccaca atatctaatt tctagaggct ctcattctat taaaattaga
1201 acttgggatg gtgaagtgat tgattatcca aatcacccta caattccaat tgaagaaaca
1261 ctaaagtaa
```

```
   1 mnhtdttnsr qisidrakhl kltiqdylei kdlipkglsr qveieakkqk ilshfgated
  61 nwndwqwqls nrisdvdtlt kiiklddkei edikkvgqef rwsvspyytt liddnnkycp
 121 iklmaiphgy eiantkgdtd pmaeeftnpa gsitrrypdr liinvtneca mycrhcqrrr
 181 nigtndlhts revlqesidy irdnpeirdv litggdaltl snsmldwllg elhaipsvdy
 241 irlgsrtlvt mpqritdkli nilkkyppif inthfnhpme iteeskaacd rlsnagiplg
 301 nqavllngin nnkfvmrlln hellkcrvrp yyifhakhvi gtshfntsvd dgieimeylr
 361 gytsgmaipt yiinapggkg ktpilpqyli srgshsikir twdgevidyp nhptipieet
 421 lk
```

The nucleotide and amino acid sequences (SEQ ID NOs:13 and 14) of the *Caldicellulosiruptor saccharolyticus* DSM 8903 polypeptide are:

```
   1 atggaaaagt tagatgttat taacaacaga gaaagattcg aaaagttaaa agaagctatt
  61 aaagactact tagaggtcaa agacacaatc aaaactggca tagatgatga ggaaaagatt
 121 gaatatcaaa aaagaaagat tctttcctac tttggtgcaa gcgaaaagga ctgggaaaat
 181 tataagtggc agctgaaaaa tagaattacc tcggccaaaa tattaaaaga acttttaaac
 241 cttgatgaaa aagaagcaca gcaaatagaa gaagtagcca aaatttaccg ttttgcaatc
 301 tcaccttact atctctcttt gattgaccca agtgatcctc actgtccaat aaagaagcaa
 361 tcagtcccaa gctcatttga gcttatagaa aaggtgagc ttgacccaat ggacgaagag
 421 catacatccc ctacaaagat tattacacag cgctatcctg acaggctcat aataaaagtt
 481 acaaacatat gtgggatgtt ttgcagattc tgtcaaagaa gaagacttat tggtgagact
 541 gacacacacg catcgctgga tgatattacg gatgcaattg aatatgtagc acaaaatcca
 601 aatatcagag atgttctcat cacaggtggc gatgccctga tgctctctga tgagattttg
 661 gagtggattt taaggtcgct aaggcaaata cctcatgttg agataatcag aattggaaca
 721 agagcacctg tgacgttgcc acaaaggatt acaaaagagc ttgttgatat gctaaaaaag
 781 tatcacccta tttatgtaaa cacccacttt aaccacccac gtgagataac aaaagaatca
 841 aaaagagctt gtgagatgct tgcagatggc ggcattccgc ttggcaacca gatggttttg
 901 ttaaatgggg tcaacaacga caaatacgtt gtgagaaggc tcaatcaaca gcttttaaaa
 961 atccgagtaa agccatatta tatctttcat ccaaaaaggg taaaaggtac atcgcacttt
1021 tgggtgacaa ttgaagaggg tatggagatt attgaaagcc tcagaggaag aacctcaggc
1081 atggcaattc ccacatacat cataaatgct ccaaaaggca aggaaaaac accaattatg
1141 ccaaattatc ttctttactt tggtaaaggc aaggtagttt ttagaaactg ggaaggtgag
1201 gtttttgagg ttgagaatgg gtaa
```

```
   1 mekldvinnr erfeklkeai kdylevkdti ktgiddeeki eyqkrkilsy fgasekdwen
  61 ykwqlknrit sakilkelln ldekeaqqie evakiyrfai spyylslidp sdphcpikkq
 121 svpssfelie kgeldpmdee htsptkiitq rypdrliikv tnicgmfcrf cqrrrliget
 181 dthaslddit daieyvaqnp nirdvlitgg dalmlsdeil ewilrslrqi phveiirigt
 241 rapvtlpqri tkelvdmlkk yhpiyvnthf nhpreitkes kracemladg giplgnqmvl
 301 lngvnndkyv vrrlnqqllk irvkpyyifh pkrvkgtshf wvtieegmei ieslrgrtsg
 361 maiptyiina pkgkgktpim pnyllyfgkg kvvfrnwege vfeveng
```

The nucleotide and amino acid sequences (SEQ ID NOs:15 and 16) of the *Desulfotomaculum reducens* MI-1 polypeptide are:

```
   1 atgtctgttc atttaaagca agaagagttc cggctaagac aagaaaaacg aaaaattgct
  61 ctaaaaaggg caaggagtt aaaagctcgt atcactgatt atcttgagaa caaggatcaa
 121 attaaaaatg gttttgaggt gcaagaacag tacaatcggg caaaacaaac tttactaaat
 181 ttttttaatg cagataatga gcagtgggaa aattggcact ggcaaatggc aaatcgtatt
 241 aaagatgtta aagtaataag ccagttaata gatctttccc cggctgaaaa agaggccatt
 301 gaaaaagtgg ggcgccagta ccgttgggcg gtatcaccct attatatggc tctggcaatg
 361 gtaagtggtt ccggtggccc tgtttggtta caggctatac cctgtataga agaagtaaag
 421 gatcgttacg gtgtagaaga tcccatggga gaagaataca cttcacctgt ggaagggta
 481 acaagacgct acccagaccg tttgattatt aatgtaacaa atcaatgtgc tatgtattgt
 541 cgccactgcc aacgacgtag aaatatcggg gaaattgatg ttcacaaatc acgtaaggtt
 601 ttagaaggtg ccctgcagta tattagggaa ataaggaga taaggatgt attaataact
 661 ggtggggatg ctttattgtt atcagaccga caaattgaat ggctgctgac tgaattagat
 721 aatattcctc atgtggaaat taagagattg gaacacgta ctccggttac tatgccccaa
 781 agaattacac cggagttatg taagatttta gagaaccatc caccgattta tatcaacacc
 841 cagtttaatc atcctttgga agttacacca gaagcaaaaa aggcctgtga tatgttggta
 901 aaagcaggtg ttgttctagg taatcaagct gtactactaa aaaatataaa taaccaaccg
 961 gatgttatga agaggttaaa ccaaagtctc ctaaccattc gagttcgccc ttactatata
1021 ttccatgcta aagccgtaaa aggaaccaga cattttatca ctggagtaga tgacggcatt
1081 gctattatgg aacaattaag aggctatacc tcaggacttg ctgttcctac gtatatcatt
1141 aatgccccca atggttatgg taaaactcct gtacttcccc agtatattat tgagaataaa
1201 aatgatcaag ttacccttag aacctgggaa agaggatta ttccctataa tattagcgga
1261 aaacattag 1 msvhlkqeef rlrqekrkia lkrakelkar itdylenkdq ikngfevqeq ynrakqtlln
  61 ffnadneqwe nwhwqmanri kdvkvisqli dlspaekeai ekvgrqyrwa vspyymalam
 121 vsgsggpvwl qaipcieevk drygvedpmg eeytspvegv trrypdrlii nvtnqcamyc
 181 rhcqrrrnig eidvhksrkv legalgyire nkeirdvlit ggdalllsdr qiewllteld
 241 niphveikrl gtrtpvtmpq ritpelckil enhppiyint qfnhplevtp eakkacdmlv
 301 kagvvlgnqa vllkninnqp dvmkrlnqsl ltirvrpyyi fhakavkgtr hfitgvddgi
 361 aimeqlrgyt sglavptyii napngygktp vlpqyiienk ndqvtlrtwe kriipynisg
 421 kh
```

The nucleotide and amino acid sequences (SEQ ID NOs: 17 and 18) of the *Carboxydothermus hydrogenoformans* Z-2901 polypeptide are:

```
   1 atgaatagag caagaatttc gcagaaagat gaaggattga aacggcaaag agagcttacc 61 cggattggtc gtagtaggtt aagggaaaga aaaaaggttt tatcgggatt tgaagcctgg 121 gaaaaaattt taaaacaaaa agagaagatt ttaaaggtat taggtggaac ggaagaagac 181 tggcaggatt ggcgctggca gttgaaaaat cggataacaa cgccggaagt tttacgaaaa 241 attttgcctt taagcgacca ggtcctctgg gaacttgagg aggtcagtaa ggtttatcgc 301 tttgccattt cgccttatta tttgagcttg attgatcccg atgatcccga ttgcggtatt 361 aagaaacagt cgattccttc cattttggag gtttagatg ataccggtga acttgacccg 421 atgaatgaag cggggacttc gccggtggcg gcggttaccc ggcgttatcc ggaccgctta 481 ataattaatg ttaccaatat gtgcgggatg tattgccgtc actgtcagcg gcgaagaaat 541 atcggtgagg ttgaccggaa aactcccagg gagcagataa aagaagccct tctttacatc 601 cgggagcata agaaatccg ggatgtttta attaccggtg gggatgcact tctcttatcc 661 gatttggagc tggactggat attaaaagaa ctttccgaaa taccccatgt agaaattaaa 721 aggattggta cccgggtacc ggtgaccttg ccgcaaaggg ttaccgataa tctggttaaa 781 atattaaaaa aatacccgcc gatatatatc aatacccagt ttaaccatcc ccgggaggta 841 actcctgagg ccaaaaaagc ggtggataaa ttaattgaag cggggtggt attaggtaat 901 caggcggtgc ttttaaaagg ggtaaatgac aatcccgtaa ttatggagaa attgaaccat 961 gagcttttaa aaattcgggt acggccgtac tatatcttcc aggcgaagag ggtacgggga 1021 acgatgcatt ttgttcccaa gattgaagac ggattaagga taatggaaag cttgcgggc 1081 tatacctcgg gactggcagt gccgtattat atcgtcaacg cgcctggagg ctttgggaaa 1141 attccgcttt tacccagta tttaattgaa ctctcggaag aagaagcagt tttacgcaac 1201 tgggaaggcc ggataattag atatccgaat aattaa 1 mnrarisqkd eglkrqrelt rigrsrlrer kkvlsgfeaw ekilkqkeki lkvlggteed 61 wqdwrwqlkn rittpevlrk ilplsdqvlw eleevskvyr faispyylsl idpddpdcgi 121 kkqsipsile vlddtgeldp mneagtspva avtrrypdrl iinvtnmcgm ycrhcqrrrn 181 igevdrktpr eqikeallyi rehkeirdvl itggdallls dleldwilke lseiphveik 241 rigtrvpvtl pqrvtdnlvk ilkkyppiyi ntqfnhprev tpeakkavdk lieagvvlgn 301 qavllkgvnd npvimeklnh ellkirvrpy yifqakrvrg tmhfvpkied glrimeslrg 361 ytsglavpyy ivnapggfgk ipllpqylie lseeeavlrn wegriirypn n
```

Thus, the present invention contemplates the use of clostridial enzyme sequences to identify glutamate 2,3-aminomutase from other species. The present invention further contemplates variants of such glutamate 2,3-aminomutases, and the use of such enzymes to preparre β-glutamate.

In one screening approach, polynucleotide molecules having nucleotide sequences disclosed herein can be used to screen genomic or cDNA libraries. Screening can be performed with clostridial glutamate 2,3-aminomutase polynucleotides that are either DNA or RNA molecules, using standard techniques. See, for example, Ausubel et al. (eds.), SHORT PROTOCOLS IN MOLECULAR BIOLOGY, pages 6-1 to 6-11 (John Wiley & Sons, Inc. 1995). Genomic and cDNA libraries can be prepared using well-known methods.

See, for example, Ausubel et al. (eds.), SHORT PROTOCOLS IN MOLECULAR BIOLOGY, pages 5-1 to 5-6 (John Wiley & Sons, Inc. 1995).

Additional glutamate 2,3-aminomutase genes can also be obtained using the polymerase chain reaction (PCR) with oligonucleotide primers having nucleotide sequences that are based upon the nucleotide sequences of the glutamate 2,3-aminomutase genes of *Clostridium, Thermoanaerobacter, Desulfitobacterium, Moorella, Syntrophomonas,* as described herein. General methods for screening libraries with PCR are provided by, for example, Yu et al., "Use of the Polymerase Chain Reaction to Screen Phage Libraries," in METHODS IN MOLECULAR BIOLOGY, Vol. 15: PCR PROTOCOLS: CURRENT METHODS AND APPLICA- TIONS, White (ed.), pages 211-215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in METHODS IN MOLECULAR BIOLOGY, Vol. 15: PCR PROTOCOLS: CURRENT METHODS AND APPLICATIONS, White (ed.), pages 317-337 (Humana Press, Inc. 1993).

Anti-glutamate 2,3-aminomutase antibodies can also be used to isolate DNA sequences that encode enzymes from cDNA libraries. For example, the antibodies can be used to screen λgt11 expression libraries, or the antibodies can be used for immunoscreening following hybrid selection and translation. See, for example, Ausubel et al. (eds.), SHORT PROTOCOLS IN MOLECULAR BIOLOGY, 3rd Edition, pages 6-12 to 6-16 (John Wiley & Sons, Inc. 1995); and Margolis et al., "Screening λ expression libraries with antibody and protein probes," in DNA CLONING 2: EXPRESSION SYSTEMS, 2nd Edition, Glover et al. (eds.), pages 1-14 (Oxford University Press 1995).

Furthermore, the identification of glutamate 2,3-aminomutases is simplified by using known conserved regions in the DNA sequences of genes encoding the enzymes. By matching the conserved sequences with potential glutamate 2,3-aminomutases, positive identification can be achieved. These conserved sequences include CXXXCRXCXR (SEQ ID NO: 19)—the iron sulfur center residues; S(T)GGD(E) (SEQ ID NO: 20)—S-adenosyl-L-methionine binding domain, and GXXXPXXXXXXXXXXXK (SEQ ID NO: 21)—pyridoxal 5'-phosphate binding domain. (The standard one-letter codes are used to represent the various amino acids of the conserved sequences; X may be any of the 20 naturally occurring amino acids.) In addition, conserved active site residues (in glutamate 2,3-aminomutase from *Cl. difficile*) important for binding to glutamate include 325 PXYXXXXKXXXG 336 (SEQ ID NO: 22) and 364 PXXXXNXXXXXK 376 (SEQ ID NO: 23). In contrast, the corresponding sequences of lysine 2,3-aminomutase from *C. subterminale* SB4 are respectively: 286 PXYXXXXDXXXG 297 (SEQ ID NO: 24) and 325 PXXXXDXXXXXK 337 (SEQ ID NO: 25). As glutamate 2,3-aminomutase does not catalyze the conversion of L-lysine to β-lysine, it is believed that the change of K for D and N for D in the active site of glutamate 2,3-aminomutase is responsible in large part for the change in substrate specificity compared to lysine 2,3-aminomutase. In variants of glutamate 2,3-aminomutase as described above include each of these conserved sequence motifs.

6. The Use of glutamate 2,3-Aminomutase to Produce β-glutamic acid

A. Production of β-Glutamate Using Purified Enzyme

Recombinant glutamate 2,3-aminomutase can be purified from host cells as described above, and used to prepare β-glutamic acid. β-glutamic acid can be prepared in batchwise reactors using soluble glutamate 2,3-aminomutase. The glutamate 2,3-aminomutase can then be mixed with the cofactors including, but not limited to: (1) ferrous sulfate or ferric ammonium sulfate; (2) pyridoxal phosphate; (3) dehydrolipoic acid, glutathione, or dithiothreitol; (4) S-adenosylmethionine; and (5) sodium dithionite, and α-glutamic acid at an appropriate pH at a temperature between 25° C. to 37° C., until the production of β-glutamic acid is at equilibrium.

Alternatively, enantiomerically pure β-glutamic acid can be obtained by continuous processing using immobilized glutamate 2,3-aminomutase. Glutamate 2,3-aminomutase can be packed in a column and activated by the addition of cofactors and a solution containing α-glutamic acid at an appropriate pH can be passed through the column at a rate that allows completion of the reaction during contact with the enzyme. The effluent from the column will contain the β-glutamic acid.

Both of the above methods will produce an equilibrium mixture of α-amino acid and β-amino acid in which the predominant species is β-amino acid. If higher purity β-glutamic acid is desired, the L-glutamic acid can be separated from the β-glutamic acid by any number of means well known in the art, including high performance chromatography procedures, such as ion exchange chromatography at an appropriate pH to take advantage of the differences in acidities of the carboxylic acid groups and the α- and β-ammonium groups.

B. Production of β-Amino Acid Using Recombinant Host Cells

In an alternative approach, β-glutamate is produced by fermentation using recombinant host cells that over-express cloned glutamate 2,3-aminomutase. General methods for high level production of amino acids from cultured bacteria are well-known to those of skill in the art. See, for example, Daugulis, *Curr. Opin. Biotechnol.* 5:192 (1994); Lee, TIBTECH 14:98 (1996).

The gene for glutamate 2,3-aminomutase can be incorporated into an *E. coli* plasmid that carries necessary markers and *E. coli* regulatory elements for overexpression of genes. When codon usage for the glutamate 2,3-aminomutase gene cloned from Clostridia is inappropriate for expression in *E. coli*, the host cells can be cotransformed with vectors that encode species of tRNA that are rare in *E. coli* but are frequently used by Clostridia. For example, cotransfection of the gene dnaY, encoding tRNA$^{ArgAGA/AGG}$, a rare species of tRNA in *E. coli*, can lead to high-level expression of heterologous genes in *E. coli*. Brinkmann et al., *Gene* 85:109 (1989) and Kane, *Curr. Opin. Biotechnol.* 6:494 (1995). Heterologous host cells expressing glutamate 2,3-aminomutase can be cultured with favorable energy, carbon and nitrogen sources under conditions in which α-amino acid in the medium is absorbed by the cells and converted intracellularly into β-amino acid by glutamate 2,3-aminomutase. Unused β-amino acid will be excreted into the growth medium. β-amino acid can then be purified from the medium by any methods well known in the art, including high performance chromatography procedures previously described.

The present invention, thus generally described, will be understood more readily by reference to the following examples, which are provided by way of illustration and are not intended to be limiting of the present invention.

EXAMPLES

Example 1

Cloning and Expression of Recombinant *Clostridium difficile* glutamate 2,3-aminomutase The DNA and translated amino acid sequ containing significant sequence identity (>60%) to the amino acid sequence of lysine 2,3-aminomutase from *Clostridium subterminale* SB4 (U.S. Pat. No. 6,248,874 B1) was obtained from the Sanger Institute genomic database (reverse complement of *Clostridium difficile* Strain 630 nucleotide sequence—Positions 2610029-2608761) following a search and subsequent sequence alignment study. *C. difficile* chromosomal DNA (obtained from American Tissue Type Cell Collection # 9689D) was used to clone the gene using PCR techniques.

Genomic DNA was dissolved in TE buffer (10 mM Tris-HCl, with 1 mM EDTA) buffer at pH 8.0 to a concentration of 0.5 µg/µl. The PCR reaction mixture (100 µl total volume) contained: *C. difficile* chromosomal DNA—1 µg; cloned Pfu DNA polymerase reaction buffer (Stratagene, La Jolla, Calif.); dNTPs—0.2 mM each; oligonucleotide primers (Primer A-5'-ACACATATGAATGAACAAACTA-GAATATCCTTAG (SEQ ID NO: 26) and Primer B-5'-TGACTCGAGTTAATCCTGTGCTTGTTCTTTTATAAG (SEQ ID NO: 27)) 25 pmoles each; cloned Pfu DNA polymerase (Stratagene, La Jolla, Calif.)—5 units. All samples were overlayered with mineral oil and subjected to 30 cycles of 1 min. at 94° C., 30 sec. at 37° C., 15 sec. at 50° C., and 2 min. at 72° C. After thermocycling, DNA formed during the PCR process was further purified by agarose electrophoresis (2% agarose, Promega Corp., Madison, Wis.) in TAE buffer (0.04 M Tris-acetate at pH 8.0 with 1 mM EDTA). Following identification and excision of the appropriately sized (1272 base pairs) ethidium bromide stained band, DNA was extracted from the agarose using the GenElute Minus EtBr spin column (Sigma #5-6501, St. Louis, Mo.), concentrated by precipitation with ethanol, and resuspended in TE buffer at pH 8.0.

The purified PCR product was blunt-end ligated to PCR Blunt II TOPO vector (Invitrogen #K2800, Carlsbad, Calif.) using 0.5 µl PCR insert product to 1 µl vector according to manufacturer's specifications. The ligated DNA was used to transform TOP10 One Shot *E. coli* cells (Invitrogen) which were subsequently plated on LB+kanamycin (50 µg/ml) plates and cultured overnight. Individual colonies were chosen and subcloned in LB+kanamycin (Fisher #BP906-5) (50 µg/ml) media for plasmid purification. Plasmid DNA was purified using Qiagen Plasmid mini kit (Qiagen, Inc., Santa Clarita, Calif.). To confirm the nucleotide sequence, the inserted gene was sequenced in entirety in four colonies by the automated ABI Prism Dye Terminator Cycle sequencing procedure (Perkin-Elmer, Norwalk, Conn.) by the University of Wisconsin Biotechnology Center (Madison, Wis.).

Purified PCR Blunt II TOPO+gene insert plasmid was subjected to restriction digestion. For the gene insert, 10 µg of plasmid DNA was cut with NdeI (New England Biolabs, Beverly, Mass.)—20 units and XhoI (Promega Corp., Madison, Wis.)—10 units in a total volume of 100 µl for 1 hour. at 37° C. The insert DNA was separated from the plasmid DNA by agarose gel electrophoresis (2% agarose in TAE buffer) and purified and concentrated as previously described. The expression vector, pET23a(+) (Novagen, Madison, Wis.) was similarly cut with NdeI and XhoI, dephosphorylated at the 5' end with calf-intestine alkaline phosphatase (Promega Corp.)—1 unit for 30 min. at 37° C., purified by agarose gel electrophoresis, and concentrated by ethanol precipitation (as previously described). The pET-23a(+) insert and the pET-23a(+) cut vector were ligated with T4 DNA ligase. To 3 ng of insert DNA were added 10 ng of cut vector in T4 DNA ligase buffer (Promega Corp.)+T4 DNA ligase (Promega Corp.)—3 units in a total volume of 10 µl and incubated for 16 hours. at 14° C. Competent *E. coli* (Epicurian coli XL2-Blue MRF', Stratagene) were transformed with 2 µl ligation mix and plated on LB+carbenicillin (Sigma #C1389) (100 µg/ml) plates and plasmid DNA isolated as described previously. The pET23a(+) gene insert was sequenced in entirety including both regions of the start and stop codon to confirm the correctness of the construct.

For protein expression, the pET23a(+) gene insert expression vector was transformed into competent *E.coli* BL21 (DE3) CodonPlus RILP cells (Stratagene, La Jolla, Calif.). This cell line is a λDE3 lysogen carrying the gene for T7 RNA polymerase under control of IPTG. For transformation, 100 µl of competent cells were treated with 54 ng of plasmid DNA Cells were heat shocked for 20 sec. at 42° C. After transformation, 10 µl of cells were plated on LB+carbenicillin (100 µg/ml)+chloramphenicol (Sigma #C-0378) (34 µ/ml) plates and grown overnight at 37° C. Individual colonies were subcultured in LB media containing carbenicillin (100 µg/ml) and chloramphenicol (34 µ/ml) to prepare frozen stocks. Cells from frozen stocks were subsequently used to streak LB plates containing carbenicillin (100 µg/ml) and chloramphenicol (34 µg/ml). Individual colonies were selected, grown in LB media containing carbenicillin (100 µg/ml) and chloramphenicol (34 µg/ml) for approximately 6 hours at 37° C., and used to inoculate 2 liter shake flasks each containing 1 liter of LB medium with ampicillin (Fisher #BP1760-25) (100 µg/ml) and chloramphenicol (34 µg/ml) and supplemented with 100 µM $FeCl_3$. Cells were cultured overnight (16 hours) at 37° C. with slow shaking (100 RPM). After 16 hours IPTG (Inalco, San Louis Obispo, Calif. #1758-1400) was added to a concentration of 1 mM, and culturing was continued for an additional 4 hours at 37° C. prior to harvesting by centrifugation. Cells were harvested by centrifugation at 6,000×$g_{av}$ for 10 min., and small portions were frozen in liquid nitrogen and stored at −70° C. until used for enzyme purification. Approximately 40 grams (wet weight) of cells were harvested from 10 liters of growth medium.

For purification of glutamate 2,3-aminomutase, all steps except centrifugation were conducted in an anaerobic chamber (Coy, Grass Lake, Mich.) at room temperature. To prevent oxygen contamination, liquid suspensions were sealed into centrifuge bottles inside the anaerobic chamber before centrifugation at 4° C. outside the chamber. Cells were thawed in 70 ml standard buffer (SB) [0.03 M sodium EPPS (Sigma #E9502) at pH 8.0, 40 µM $FeSO_4$ (J T Baker #2070-1), 40 µM pyridoxal-5'-phosphate (Sigma #P9255), 1 mM L-glutamate, 1 mM DTT (Inalco #1758-9030), and 1 mM PMSF (Sigma #P7626)] prior to sonication using the standard tip of the Sonic Dismembrator (Misonix, Farmingdale, N.Y., Model #3000) (setting 8 for six 30 sec. intervals at 4-8° C.). Following sonication, cells were centrifuged at 20,000×$g_{av}$ for 30 min. The supernatant fluid was subjected sequentially first to streptomycin sulfate (Sigma #S6501) treatment (3% at 4° C.) to remove nucleic acids, and then to ammonium sulfate treatment (70% saturation at 4° C.) to precipitate proteins. Each precipitation was followed by centrifugation at 20,000×$g_{av}$ for 20 min at 4° C.

The protein pellet after ammonium sulfate precipitation was dissolved in SB+1 M ammonium sulfate and applied to a phenyl-Sepharose 6 Fast Flow (high substitution) (Amersham Biosciences, Piscataway, N.J.) column (2.5×25 cm) previously equilibrated with the same buffer. The enzyme was adsorbed to the column and was eluted with a linear gradient formed from two liters each of 1.) SB+1 M ammonium sulfate and 2.) SB. The gradient starting at 1 M ammonium sulfate and decreasing linearly was operated at a flow rate of 2.5 ml/min. Glutamate 2,3-aminomutase emerged toward the end of the gradient as a yellow-brown band of protein. The desired fractions were identified and pooled, and the protein was precipitated by addition of solid ammonium sulfate (70% saturation 4° C.) and centrifugation as previously described. The precipitated protein was redissolved in 750 ml of SB and applied to a Q-Sepharose Fast Flow (Amersham Biosciences) column (2.5×25 cm) column previously equilibrated with SB buffer. Bound protein was eluted with a linear gradient composed of two liters each of 1.) SB and 2.) SB+0.5 M NaCl and operated at a flow rate of 2.5 ml/min.

Glutamate 2,3-aminomutase emerged in the latter half of the gradient as a yellow-brown protein band that was collected and concentrated by ammonium sulfate precipitation (70% saturation at 4° C.) and centrifugation at 20,000×$g_{av}$ for 20 min. The protein pellet was dissolved in 6 ml of SB buffer and passed through a Sephacryl S200 HR (Amersham Biosciences) column (2.5×25 cm) equilibrated with SB at a flow rate of 2 ml/min. The protein band was collected and concentrated using Centricon YM10 (Amicon, Bedford, Mass.) spin concentrators to a protein concentration of 20 mg/ml, frozen as droplets in liquid nitrogen, and stored in liquid nitrogen until used for analysis.

Example 2

Quantitative Analysis of Purified Glutamate 2,3-aminomutase

The gene product of the C. difficile gene prepared according to Example 1 was analyzed using the following procedures.

SDS PAGE electrophoresis. SDS polyacrylamide gel electrophoresis was conducted according to the method of Laemmli (24) using Tris-glycine buffer {0.025M Tris, 0.19 M glycine, 0.1% SDS (sodium dodecyl sulfate)} and 10-20% polyacrylamide gels (Ready Gel #161-1106, Bio-Rad, Hercules, Calif.).

Measurement of Protein Concentration by Amino Acid Analysis: Method. The protein concentration of the purified C. difficile glutamate 2,3-aminomutase was measured by amino acid analysis following complete hydrolysis in 6 N HCl at 110° C. Protein (5 μl) was added to hydrolysis tubes (Pierce Chemical Co., Rockford, Ill.) containing 700 μl 6N HCl. To one half the tubes, 25 μl of amino acid standard solution (2.5 mM each amino acid—Pierce Chemical Co—#20088) was added in addition to protein. Tubes were sealed in vacuo and heated for 24, 48, and 72 hours at 110° C. Following hydrolysis, samples were transferred to 2 ml microcentrifuge tubes and concentrated to dryness by vacuum centrifugation. The dried samples and amino acid standards were derivatized with PITC (Pierce Chemical Co., Rockford, Ill.) and separated by HPLC according to the method of Heinrikson and Meredith (20). Dried samples were dissolved in 100 μl of coupling buffer, concentrated to dryness by vacuum centrifugation, redissolved in 100 μl coupling buffer plus 10 microliters of PITC, allowed to react for 30 min at room temperature, concentrated to dryness as above, and dissolved in 1 ml water prior to injection and separation by HPLC using a Beckman Gold HPLC. The PITC derivative of each amino acid was separated by HPLC chromatography using a C18 reverse phase column (Phenomenex Gemini 5μ, 4.6 mm×25 cm, #G-4435-EO), flow rate 1 ml/min, room temperature, sample injection volume 50 μl. The eluted compounds were detected by spectrophotometry at a wavelength of 254 nm. The PITC-amino acids were separated with a complex linear gradient starting with 0.05 M ammonium acetate in water (buffer A) and 0.10 M ammonium acetate in 44% water, 46% acetonitrile, and 10% methanol (buffer B). The gradient established was 0% Buffer B in 5 min, 0-10% Buffer B in 40 min, 10-35% Buffer B in 35 min, 35-55% Buffer B in 35 min, 55-100% Buffer B in 10 min. The PITC derivatives of the amino acids emerged from the column at the following retention times in minutes: Asx—13, Glx—18, Ser—36, Gly—39, His—54, Thr—56, Ala—58, Arg—60, Pro—62, Tyr—84, Val—85, Met—89, Ile—98, Leu—99, Phe—108 and Lys—117.

Cofactor analysis. Iron content was measured by the method of Kennedy et al (21). Sulfide analysis was conducted by the method of Beinert (22). Pyridoxal 5'-phosphate was measured by the method of Wada and Snell (23).

Glutamate 2,3-aminomutase Activity Measurements. Enzyme assays were conducted in an anaerobic chamber (Coy, Grass Lake, Mich.) at 37° C. Recombinantly produced glutamate 2,3-aminomutase (0.15 μM—subunit) was mixed with the following components: A) EPPS, 60 mM pH 8.0, Na salt; B) S-(5'-adenosyl)-L-methionine (Sigma) 250 μM; sodium hydrosulfite (Sigma #G-1251; also known as sodium dithionite) 65 μM; C) L-glutamate (Sigma #G1251) or β-glutamate (Sigma #G-1763) 20 mM. At various time intervals (0-3 min), 45 μl of reaction mix was added to 15 μl of 2N perchloric acid to stop the reaction. Samples were centrifuged at 14,000×g for 10 min. The supernatant fluids were treated with PITC according to the method of Heinrikson and Meredith (20). Samples were dissolved in 100 μl of coupling buffer, concentrated to dryness by vacuum centrifugation, redissolved in 400 μl coupling buffer plus 20 μl of PITC, allowed to react for 30 min at room temperature, concentrated to dryness as above, and dissolved in either 0.5 or 1.0 ml water prior to injection (50 or 100 μl). The PITC derivative of L-glutamate was separated from the β-glutamate derivative by HPLC chromatography (20) using a C18 reverse phase column (Phenomenex Gemini 5μ, 4.6 mm×25 cm, #G-4435-E0), flow rate 1 ml/min, room temperature. The PITC-amino acids were separated with a linear gradient composed of 0.05 M ammonium acetate in water (buffer A) and 0.1 M ammonium acetate in 44% water, 46% acetonitrile, and 10% methanol (buffer B). The gradient established was 0-10% Buffer B in 20 min, 10-100% Buffer B in 10 min. The PITC derivative of L-glutamate emerged at a retention time of 14.8-15.0 min whereas the PITC derivative of β-glutamate emerged at 15.5-15.7 min. Concentrations of L-glutamate or β-glutamate were measured using an amino acid standard solution (Pierce Chemical Co., #20088). For enzyme activity measurements at selected time points, the peak area of either L-glutamate or β-glutamate was divided by the total peak area (L-glutamate+β-glutamate) and multiplied by the starting concentration of either L-glutamate or β-glutamate to obtain molar concentrations. Enzyme kinetic parameters were determined by varying the concentration of L-glutamate (0.6-20 mM). Two separate analyses were conducted at two concentrations of enzyme (0.75 and 0.15 μM—subunit) with remaining conditions as stated above. Initial velocities were measured and used to calculate kinetic parameters ($V_{max}$ and $K_m$) by the nonlinear least squares curve fitting method of Cleland (25).

Measurement of the Equilibrium Constant for Conversion of L-Glutamate into β-Glutamate Catalyzed by Glutamate 2,3-aminomutase. Assays were conducted as previously described (see activity measurements above) except at 24° C. Initial concentrations of either L-glutamate or β-glutamate were set at 0.6 to 20 mM. Initial enzyme concentrations were either 0.75 μM or 0.15 μM. After approximately 4 hours at 24° C., an additional aliquot of enzyme was added to make the final enzyme concentration either 1.5 μM or 0.3 μM, and the reaction was allowed to proceed for an additional 16 hours at 24° C. The reaction was stopped with 0.55 N perchloric acid, and the amino acids were derivatized with PITC as previously described. Following HPLC separation of the PITC derivatized L-glutamate and β-glutamate, the simple ratio of the peak areas of the two compounds was calculated based on the equivalent extinction coefficient of the two compounds (20).

Electron Paramagnetic Resonance (EPR) spectroscopy of C. difficile Glutamate 2,3-aminomutase. Enzyme as isolated (180 μM-subunit) was quickly mixed at 24° C. and frozen at −150° C. (total time <30 sec) with the following components: Tris (Sigma #252859) (Tris-sulfate) at 80 mM and pH 8.0; S-(5'-adenosyl)-L-methionine, 1 mM; sodium dithionite, 1 mM. In addition, each solution contained one of the following: A) L-glutamate at 50 mM; B) β-glutamate at 50 mM; C) (2-$^{13}$C)-DL-glutamate (Aldrich, Milwaukee, Wis., #48,657-4) at 100 mM; D) (2,3,3,4,4-d$_5$)-L-glutamate (Aldrich-Isotech #616281) at 50 mM; E) L-glutamate 50 mM with S-(5'-adenosyl)-L-methionine omitted; F) L-Glutamate at 50 mM with sodium dithionite omitted. Following freezing, samples were evaluated at 77° K by EPR using a Varian model E3 spectrometer with the following settings: Field center 3260 Gauss; Scan width 200 Gauss; Microwave frequency 9.1 GHz; Microwave power 5 milliWatts; Modulation frequency 100 kHz; Modulation amplitude 2.0 Gauss; Time constant 0.3 sec; Scan time 240 sec. Gain 80,000 (A,B,E, F), 320,000 (C), 40,000 (D).

UV-Visible Spectrophotometry of *Cl. difficile* Glutamate 2,3-aminomutase. The UV-Visible absorption spectrum of the purified enzyme (0.45 mg/ml) in 0.02M sodium EPPS buffer at pH 8.0 was measured anaerobically with a Hewlett-Packard Diode Array Spectrophotometer (Model 8452A).

Cloning the *C. difficile* gene with a suitable plasmid expression vector, pET23a(+) (Novagen) clearly demonstrated high expression in *E. coli* cells (FIG. 1). As shown in column 2, SDS polyacrylamide gel electrophoresis (PAGE) of a cellular extract isolated from *E. coli* cells disrupted by sonication following induction of recombinant protein synthesis indicated one predominant band at approximately 50 KDa with many minor bands from other cellular proteins. The size of the major protein is comparable to the calculated molecular weight of 48.9 KDa for the gene product based on amino acid content. Purification of the recombinant protein by conventional column chromatography yielded approximately 200 mg of purified protein from 40 gms (wet weight) of *E. coli* cells. As shown in lane 3 of FIG. 1, the purification procedure produces a highly purified protein with less than 5% contaminating protein. The high purity of the recombinant protein shown by SDS PAGE, estimated to be ~95%, is supported by the results of amino acid analysis of the purified protein (Table 1). The data on amino acid content data agree with the expected number of each amino acid measured from the predicted amino acid sequence (SEQ ID #2).

TABLE 1

Estimation of Protein Concentration by Amino Acid Analysis

| Amino Acid | No | Protein Concentration (mM) - Subunit | | |
|---|---|---|---|---|
| | | 24 hours | 48 hours | 72 hours |
| GLY | 21 | 0.41 | 0.42 | 0.49 |
| HIS | 9 | 0.44 | 0.44 | 0.44 |
| ALA | 16 | 0.44 | 0.47 | 0.47 |
| ARG | 23 | 0.44 | 0.47 | 0.46 |
| PRO | 18 | 0.41 | 0.42 | 0.40 |
| GLX | 56 | 0.45 | 0.48 | 0.50 |
| TYR | 20 | 0.46 | 0.46 | 0.46 |
| VAL | 19 | 0.43 | 0.43 | 0.45 |
| MET | 11 | 0.44 | 0.43 | 0.42 |
| ILE | 41 | 0.44 | 0.46 | 0.42 |
| LEU | 38 | 0.44 | 0.45 | 0.47 |
| PHE | 6 | 0.45 | 0.44 | 0.45 |
| LYS | 37 | 0.41 | 0.41 | 0.40 |
| Protein Concentration (Mean ± SD, n = 39) 440 ± 24 µM | | | | |
| SER | 17 | 0.42 | 0.39 | 0.37 |
| THR | 27 | 0.40 | 0.35 | 0.32 |
| ASX | 50 | 0.54 | 0.71 | 0.69 |
| CYS | 8 | NA* | NA* | NA |
| TRP | 5 | NA* | NA* | NA |

*NA Not available

Amino acid analysis also allowed for an accurate measurement of protein concentration of the recombinant protein (Table 1). All amino acids with the exception of Ser, Thr, Asx, Cys, and Trp were used to measure protein concentration following complete acid hydrolysis and amino acid analysis by HPLC procedure. Ser and Thr were found to decrease with extended hydrolysis as expected (26). Asx (Asp+Asn) increased at 48 and 72 hours hydrolysis due to the conversion of cysteine to cysteic acid. In the HPLC separation, the PITC derivative of cysteic acid has the same retention time as the PITC derivative of aspartic acid. Cys and Trp were destroyed by acid hydrolysis and could not be measured by this procedure. Based on this protein analysis, the cofactor content of the purified recombinant protein is: 2.9±0.14 Fe/subunit; 2.5±0.13 S$^{2-}$/subunit; and 1.1±0.05 pyridoxal-5'-phosphate/subunit.

Figure 2A:
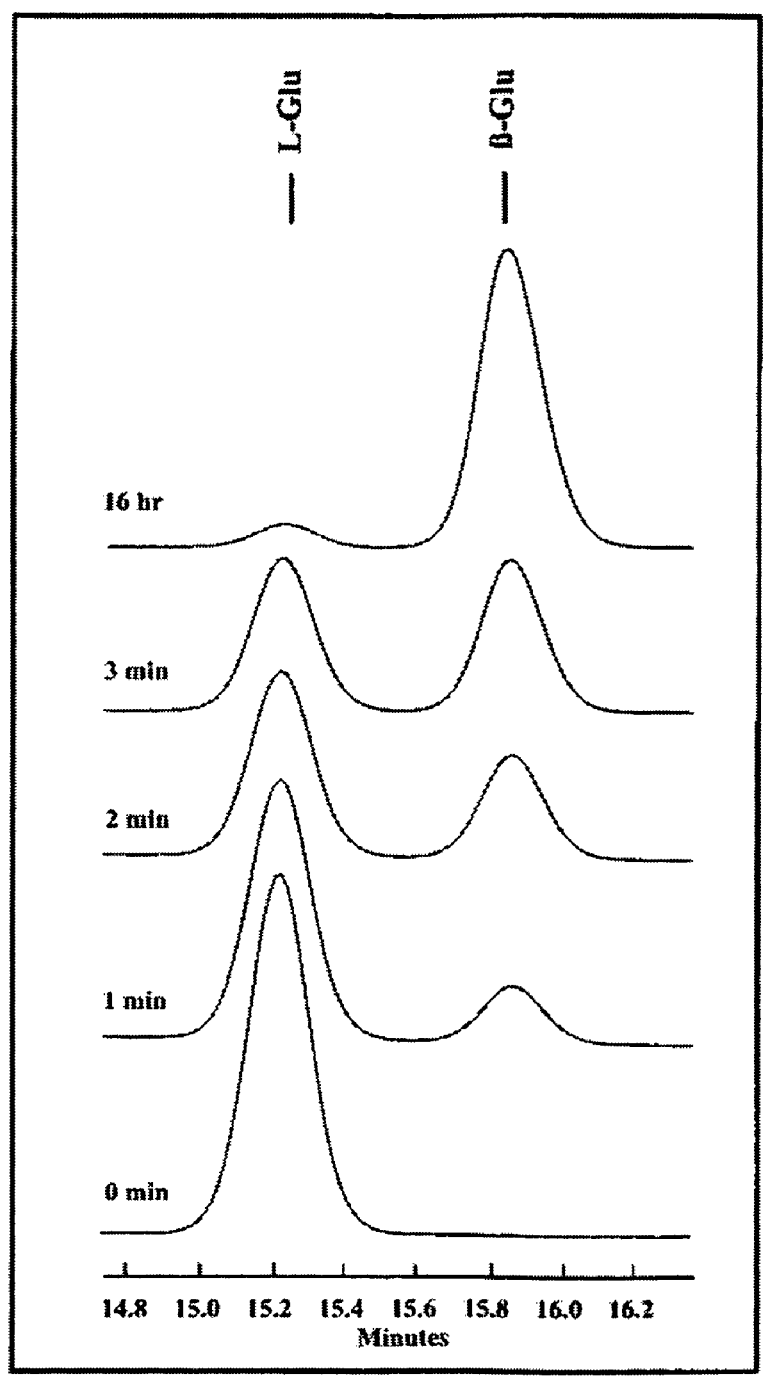
FIG. 2. Interconversion of L-glutamate and β-glutamate by *C. difficile* glutamate 2,3-aminomutase. Separation and identification by HPLC. Assay conditions as described in the Examples: A. L-glutamate as substrate. Initial conditions: L-glutamate—5 mM, enzyme 3.7 μM (subunit). B. β-glutamate as substrate. Initial conditions: β-glutamate—5 mM, enzyme 3.7 μM (subunit).
Figure 2B:
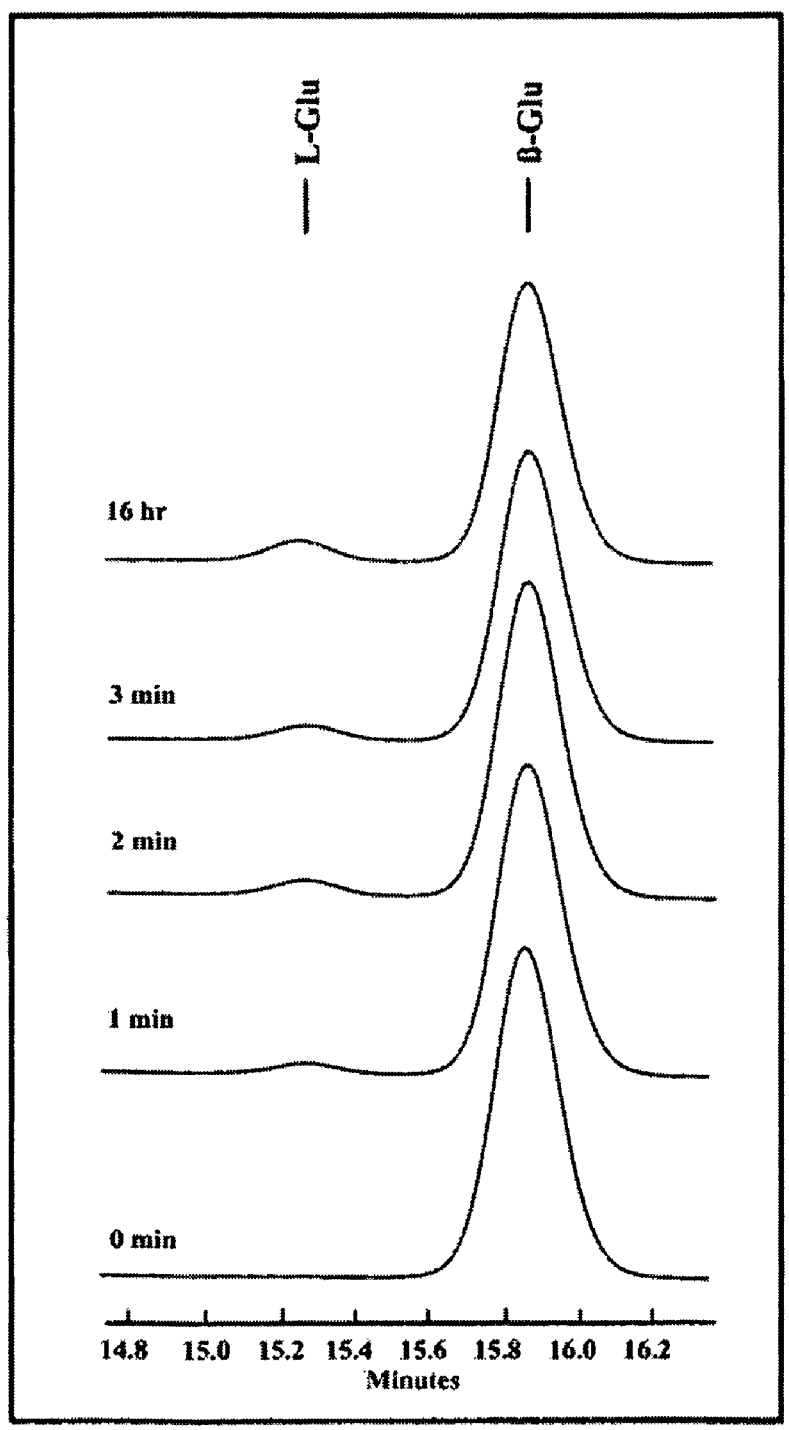

As shown in FIGS. 2A and 2B, the recombinant protein displays L-glutamate 2,3-aminomutase activity. PITC-derivatized L-glutamate and β-glutamate are separable by HPLC. FIG. 2A shows HPLC chromatograms that demonstrate conversion of L-glutamate to β-glutamate within minutes at 37° C. in solutions containing purified recombinant protein. Similarly, FIG. 2B shows that the enzyme catalyzes the reverse reaction from β-glutamate to L-glutamate. The products of both the forward and reverse reactions were identified by addition of increasing amounts of L-glutamate and β-glutamate standards to the unknowns. Co-chromatography produced a single symmetrical peak in each case. Both reactions starting with different substrates led to the same end point, equilibrium in which β-Glu is favored to L-glutamate by a ratio of approximately 16 to 1 (Table 2).

TABLE 2

Measurement of the Equilibrium Constant for L-Glutamate: β-Glutamate Catalyzed by *C. difficile* Glutamate 2,3-aminomutase at 24° C.

| [L-Glutamate] mM (start) | $K_{eq}$ | [β-Glutamate] mM (start) | $K_{eq}$ |
|---|---|---|---|
| [Enzyme] = 1.5 µM (subunit) | | | |
| 22.9 | 15.3 | 22.9 | 15.9 |
| 12.4 | 15.6 | 12.3 | 16.4 |
| 6.6 | 15.6 | 6.2 | 16.4 |
| 3.1 | 16.0 | 3.1 | 16.3 |
| 1.4 | 15.2 | 1.4 | 15.8 |
| 0.6 | 14.2 | 0.6 | 15.3 |
| [Enzyme] = 0.30 µM (subunit) | | | |
| 22.1 | 15.5 | 24.3 | 16.1 |
| 12.9 | 16.3 | 12.3 | 16.6 |
| 6.4 | 15.9 | 6.2 | 15.7 |
| 3.2 | 15.9 | 3.1 | 16.2 |
| 1.6 | 15.7 | 1.4 | 15.6 |
| 0.8 | 14.8 | 0.6 | 15.6 |
| $K_{eq}$ [β-Glutamate]/[L-Glutamate] = 15.7 ± 0.5   Mean ± SD (n = 24) | | | |

Figure 3:
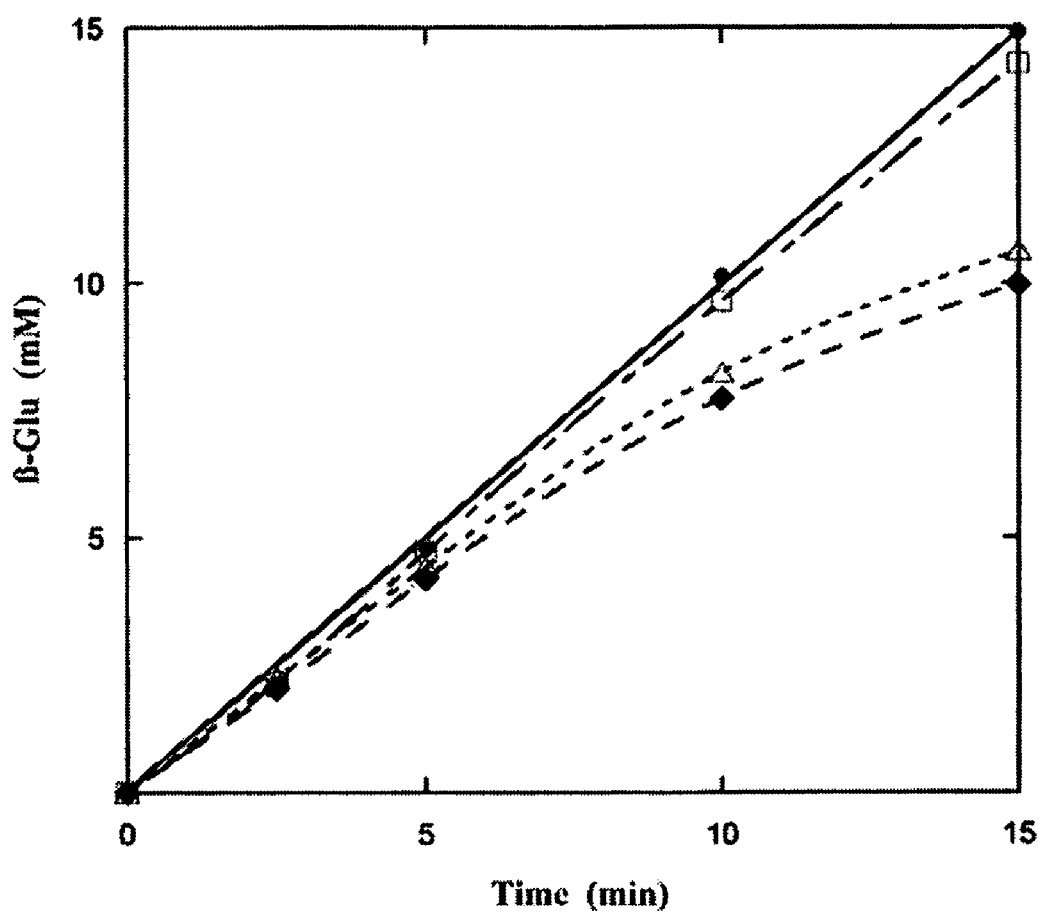
FIG. 3. Effect of Sodium Dithionite Concentration on the Activity of Purified *C. difficile* Glutamate 2,3-aminomutase. Assay conditions as described in the Examples except the following: L-glutamate, 50 mM; S-(5'-adenosyl)-L-methionine, 250 μM; enzyme, 3.7 μM; and sodium dithionite concentrations: ♦ - - - ♦, 3.3 mM; Δ - - - Δ, 0.67 mM; □— - —□, 0.17 mM; ●—●, 0.067 mM.
Figure 4:
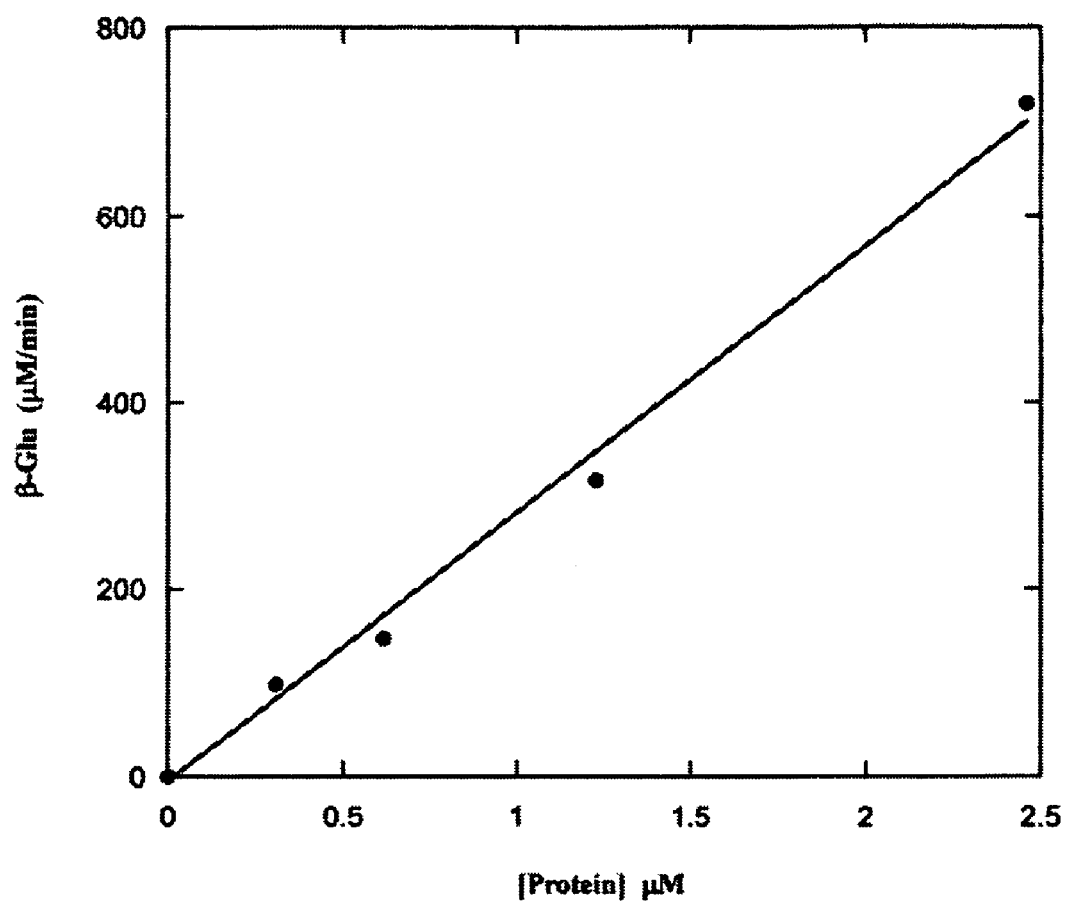
FIG. 4. Protein Concentration vs. Glutamate 2,3-Aminomutase Activity. Purified glutamate 2,3-aminomutase was used as isolated. Assay conditions as described in the Examples except the following: L-glutamate 50 mM, S-(5'-adenosyl)-L-methionine 250 μM, and sodium dithionite 0.067 mM.
Figure 5:
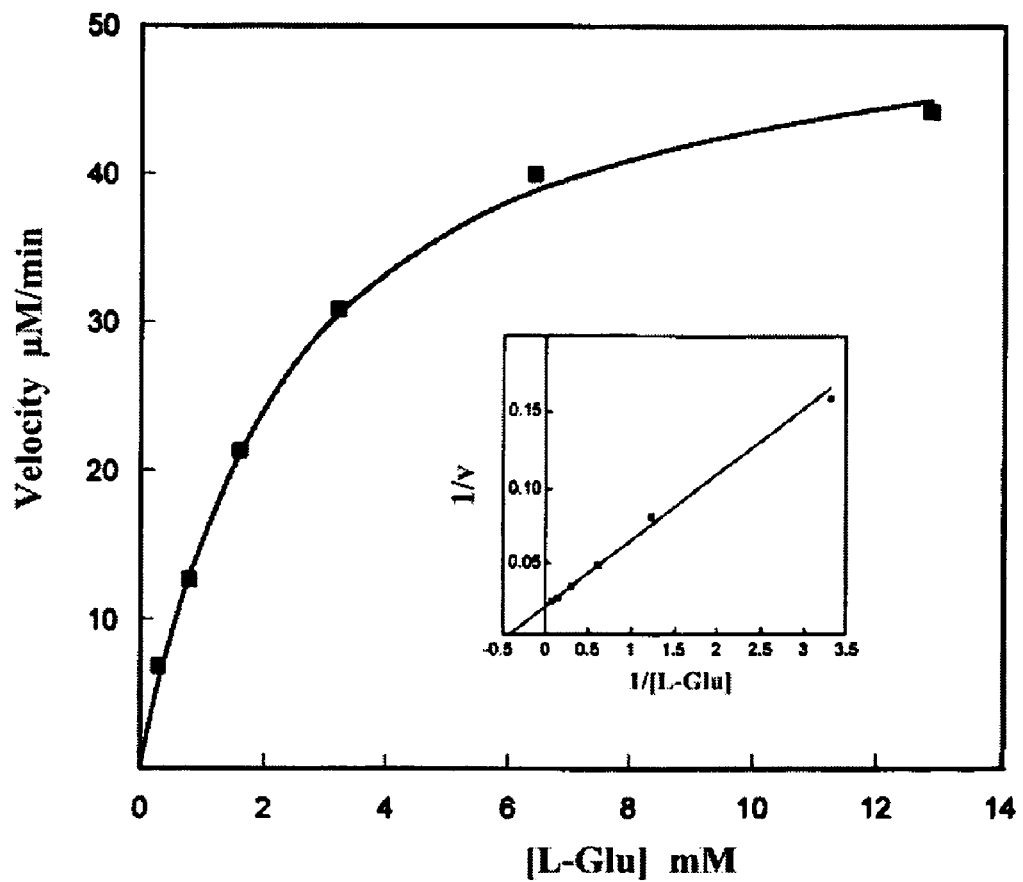
FIG. 5. Glutamate 2,3-aminomutase Activity vs. L-Glutamate Concentration. Enzyme kinetic parameters were determined by varying the concentration of L-glutamate (0.6-20 mM) following assay conditions described in the Examples. Enzyme concentration was 0.15 μM. Initial velocities were measured, and curve fitting was done by the nonlinear least squares curve fitting method of Cleland (25). Insert: double reciprocal (Lineweaver Burk) plot of saturation data.

Properties of the enzyme catalyzed reaction are shown in Table 3A. Enzyme activity measured at 20 mM for either substrate indicates very significant rates in the forward and reverse directions: 20 mM L-glutamate reacts to produce β-glutamate at a rate of 5.9 μmoles min$^{-1}$ (mg protein)$^{-1}$, and 20 mM β-glutamate reacts to produce L-glutamate at a rate of 2.3 μmoles min$^{-1}$ (mg protein)$^{-1}$. The in vitro reaction depends on the addition of S-(5'-adenosyl)-L-methionine as a cofactor and sodium dithionite as a reducing agent. Although dithionite is necessary for this reaction, an excess can be inhibitory (FIG. 3). A progressive loss over time of enzyme activity was observed at higher levels of dithionite (>70 μM) A slight increase (20%) in enzyme activity was observed when purified enzyme was subjected to reductive incubation, a reductive process utilizing a thiol agent, L-cysteine and iron to restore full activity lost during purification (Table 3). Activity was found to be proportional to enzyme concentration (FIG. 4).

TABLE 3

Activity and Kinetic Parameters of Purified *C. difficile* Glutamate 2,3-aminomutase at 37° C.

A. Enzyme Activity

| Substrate | SAM | Dithionite | Specific Activity (μmoles · min$^{-1}$ · mg$^{-1}$ Protein) |
|---|---|---|---|
| L-Glutamate* | + | + | 5.9 |
| L-Glutamate* | + | − | 0.16 |
| L-Glutamate* | − | + | <0.01 |
| β-Glutamate* | + | + | 2.3 |

*Concentration of substrates - 20 mM

B. Kinetic Parameters

| | $K_m$ (L-Glutamate) mM | $V_{max}$* | $k_{cat}$ s$^{-1}$ | $k_{cat}/K_m$ M$^{-1}$·s$^{-1}$ |
|---|---|---|---|---|
| Assay 1 | 2.2 ± 0.16 | 7.5 ± 0.18 | 6.2 | 2840 |
| Assay 2 | 2.3 ± 0.18 | 7.3 ± 0.19 | 6.0 | 2550 |

*μmoles · β-Glutamate min$^{-1}$ (mg protein)$^{-1}$

Kinetic parameters in the forward direction were measured (Table 3B). The Michaelis constant ($K_m$) for L-glutamate is 2 mM, and the maximum velocity at 37° C. is 7 μmoles of β-glutamate min$^{-1}$ (mg protein)$^{-1}$. The value of $k_{cat}$ is 6 s$^{-1}$ and that of $k_{cat}/K_m$ is 2500 M$^{-1}$s$^{-1}$ under the conditions of Table 3, indicating efficient enzymatic catalysis. These values are within the same order of magnitude to those reported for *C. subterminale* SB4 lysine 2,3-aminomutase (27).

Figure 7:
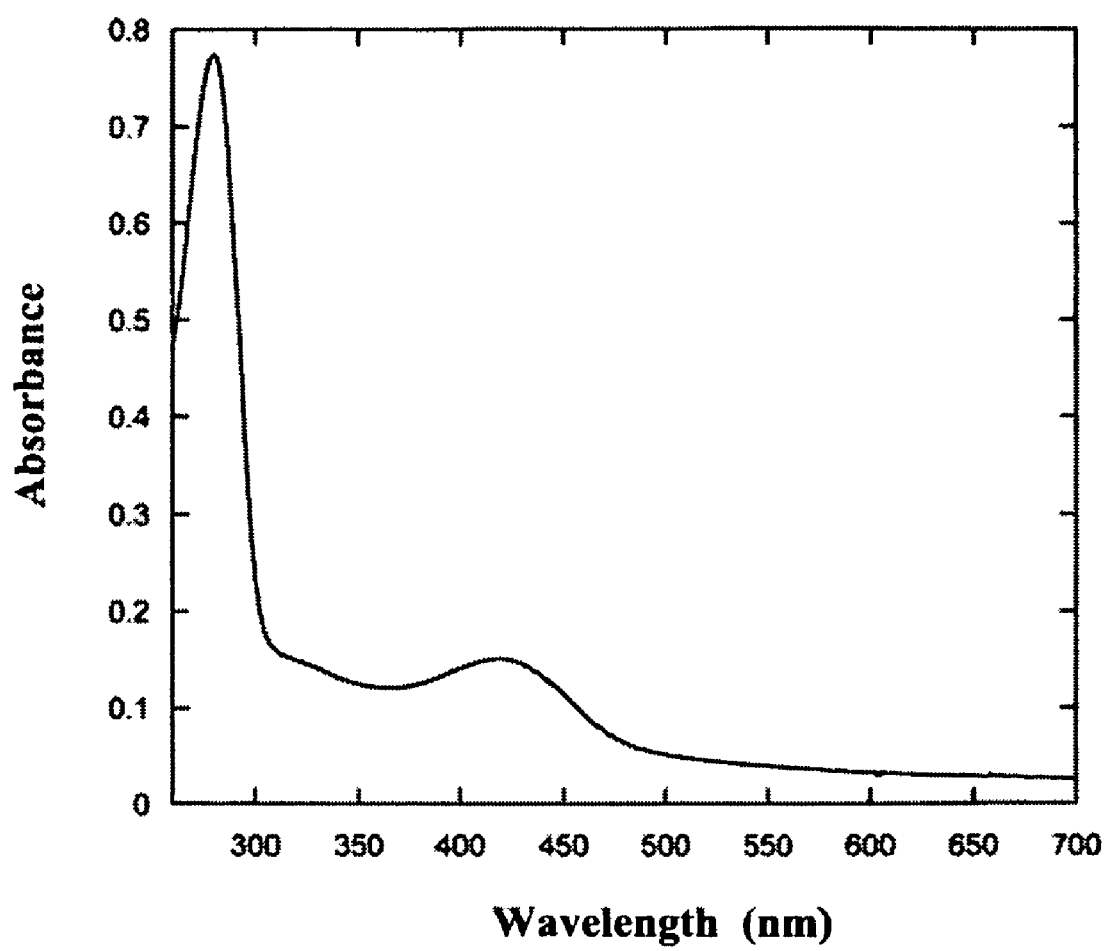
FIG. 7. UV-Visible Spectrophotometry of *C. difficile* Glutamate 2,3-aminomutase. Purified enzyme as isolated (0.45 mg/ml) in 0.02M sodium EPPS pH 8.0 buffer was evaluated anaerobically with a Hewlett-Packard Diode Array Spectrophotometer (Model 8452A).

The purified recombinant enzyme (FIG. 7) exhibits spectroscopic properties resembling lysine 2,3-aminomutase from *C. subterminale* SB4. The UV-Visible absorption spectrum of the purified enzyme displays two prominent peaks at 280 and 420 nm typical of absorption due to amino acid components (Phe and Tyr) at 280 nm and the internal aldimine of pyridoxal-5'-phosphate at 420 nm. Furthermore a broad overlapping absorption band is observed decreasing from 300 nm to 700 nm representative of iron-sulfur cluster absorption.

EPR spectroscopy of the purified enzyme in the presence of either L-glutamate or β-glutamate and S-(5'-adenosyl)-L-methionine and reduced by dithionite (FIG. 6A, B) reveals the presence of a radical species analogous to the product-related radical reported for the reaction of *C. subterminale* SB4 lysine 2,3-aminomutase with L-lysine (13). The splittings in the EPR signal result from nuclear hyperfine coupling of the C2-hydrogen atom with the unpaired electron on C2. FIG. 6D shows that when deuterium labeled [2,3,3,4,4-d$_5$]-L-glutamate was used, the signal collapses into a single, broadened line. This results from the 6-fold smaller splitting constant for deuterium relative to hydrogen. The spectrum shown in FIG. 6C proves that the EPR signal originates from a radical with the unpaired electron centered on C2 of β-glutamate. FIG. 6C shows significant signal broadening and changes in the splitting pattern when L-[2-$^{13}$C]glutamate is substituted for L-glutamate. As in enzyme activity measurements, no EPR signal can be observed when either S-(5'-adenosyl)-L-methionine or dithionite are omitted (FIG. 6E, F).

Figure 6:
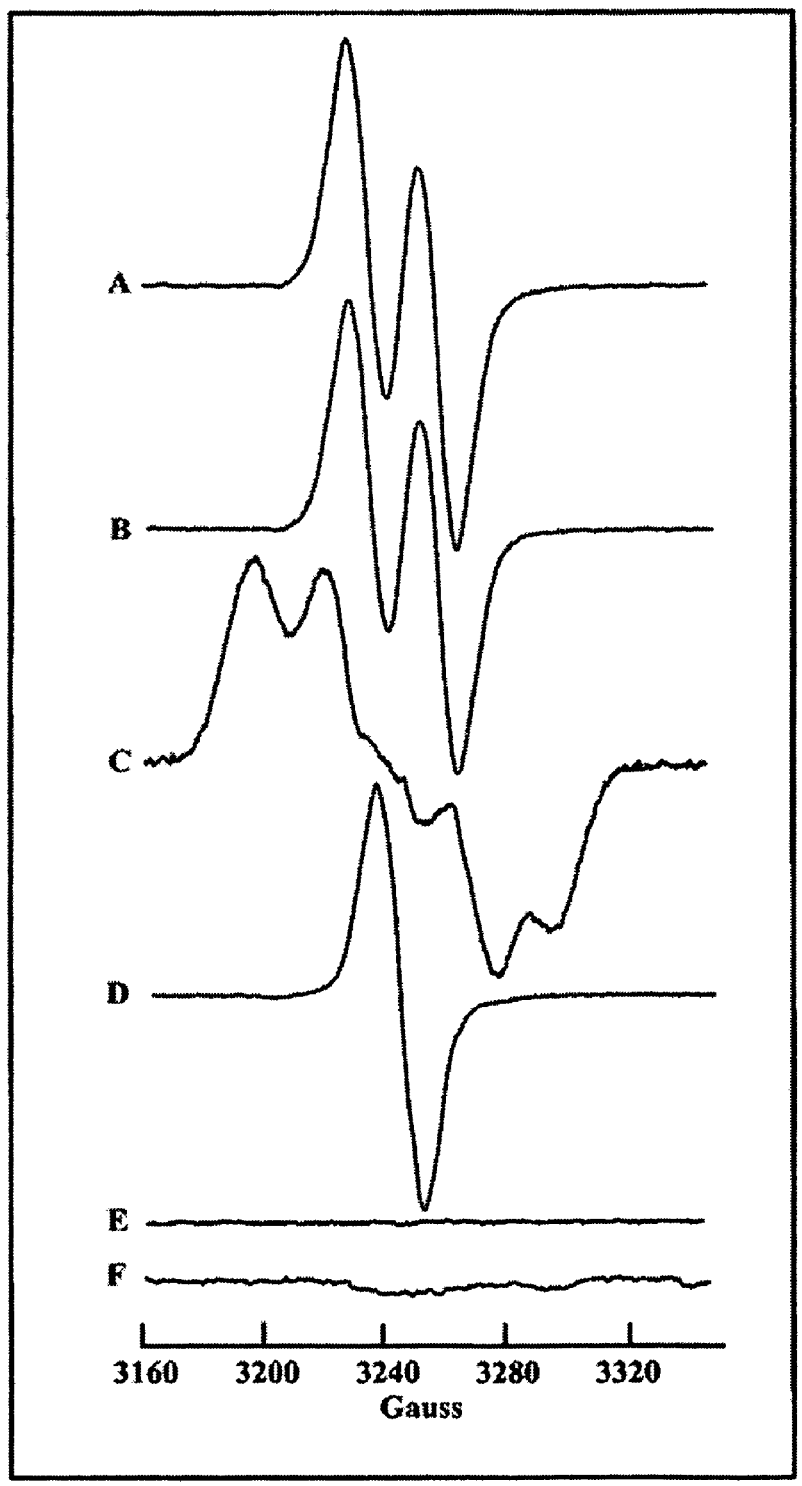
FIG. 6. Electron Paramagnetic Resonance (EPR) spectroscopy of *C. difficile* Glutamate 2,3-aminomutase. See Example 2 for description of sample preparation. A) L-glutamate 50 mM, B) β-glutamate 50 mM, C) (2-13C)-DL-glutamate 100 mM; D) (2,3,3,4,4-$d_5$)-L-glutamate 50 mM, E) L-glutamate 50 mM S-(5'-adenosyl)-L-methionine omitted, F) L-glutamate 50 mM, sodium dithionite omitted.

Glutamate 2,3-aminomutase expressed by *E. coli* in aerobic shake flasks is active inside the *E. coli* cell. This is known by the fact that analysis of the protein-free cell extract from *E. coli* expressing the enzyme shows the presence of both L-glutamate and β-glutamate, predominantly β-glutamate. PITC-derivatization of the cell extract and HPLC analysis clearly shows the PITC-derivatives of both amino acids, with PITC-β-glutamate as the dominant species. The predominance of β-glutamate also shows that the reaction in vivo is near equilibrium, in accord with the equilibrium constant in Table The coenzyme requirements of glutamate 2,3-aminomutase are the same as those of lysine 2,3-aminomutase, and the amino acid sequences of the two enzymes are similar. While not wishing to be bound by theory, on this basis, it is believed that the two enzymes are likely to act by similar chemical mechanisms, while displaying different substrate specificities. In support of this proposition, the free radical observed by EPR spectroscopy in the steady state of the reaction of glutamate 2,3-aminomutase is analogous to that observed in the reaction of lysine 2,3-aminomutase. The two free radicals display spin on C2 of the carbon skeletons of the two respective substrates. The two free radicals are the product-related radicals in the radical isomerization mechanism established for the action of lysine 2,3-aminomutase. This mechanism is adapted to the reaction of glutamate 2,3-aminomutase in FIG. 8. The mechanism is the same as that for lysine 2,3-aminomutase, with the substitution of a carboxymethyl group ($^-$OOC—CH$_2$—) in L-glutamate for the aminopropyl group ($^+$H$_3$N—CH$_2$CH$_2$CH$_2$—) in L-lysine. The EPR spectrum of the free radical observed in the steady state of the reaction of glutamate 2,3-aminomutase in FIG. 6 is radical 3 in FIG. 8.

Figure 8:
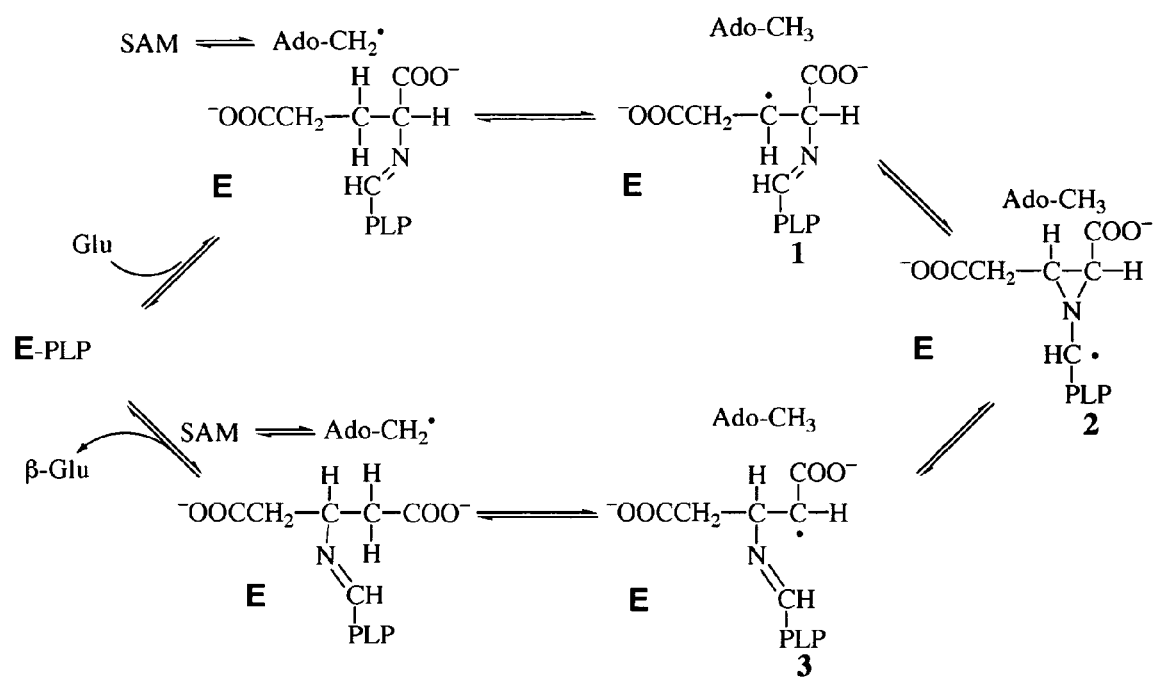
FIG. 8. The likely chemical mechanism for the action of glutamate 2,3-aminomutase.

Thus, again while not wishing to be bound by theory, it is believed that the chemical mechanism in FIG. 8 is initiated by the reversible cleavage of S-(5'-adenosyl)-L-methionine into the 5-deoxyadenosyl radical and methionine at the active site of glutamate 2,3-aminomutase. This is likely brought about by electron transfer from the [4Fe-4S]$^{1+}$ cluster by the same mechanism as in the action of lysine 2,3-aminomutase (10, 11, 15-17).

Example 3

Cloning, Expression and Analysis of Glutamate 2,3-aminomutase from Other Species Based on the nucleic acid sequences obtained from the genomic database (SEQ ID NOs: 3,5,7,9), synthetic genes optimized for expression in *E. coli* hosts were obtained from Genscript Corp., Piscataway, N.J. Each of these genes was supplied ligated to the pUC57 plasmid containing NdeI and XhoI restriction sites for future cloning in the appropriate *E. coli* expression vector. The synthetic genes had the following nucleic acid sequences, each of which codes for the identical protein indicated in SEQ ID Nos: 4, 6, 8, and 10, respectively:

*Thermoanaerobacter tengcongensis* (SEQ ID NO: 28)

```
   1 ATGAGCTCCA CCGGTAGCCT GACTGTGGAA GAAAACGTA AAATTGCCCT GCAGCGCGCA
  61 GAGGAGCTGA AAAGAAAAT CGAACCATAC CTGCGTGCCA GCGAGAAAAT CGAAACAGGA
 121 TTTAAACTGA GCGAAAAGTT TCGTGAAAAC AAAGAAAAGA TCAAGAACCT GTTTGGCGCA
 181 ACTGAAGAAG AATGGAACGA TTGGCGCTGG CAGATCCGCA ACCGCATTTC AGATGTGGAG
 241 ACCCTGAAGA AAATTGTTAA CCTGAGCGAA GAAGAAATTG AAAACATTAA GCGCGTCAGT
 301 ACTCGCTATC GTTGGGCAAT TCGCCGTAT TATGCATCGC TGATGGACCC GGATAACCCT
 361 TTTTGCCCGA TTCGCATGCG CGCAATCCCG TCTATCAAAG AACTGACAGA TAAATATGGC
 421 GTGCCAGATC CGATGGCGGA GGAATATACG TCCCCGGCGC CGCTGATTAC TCGCCGTTAT
 481 CCGGATCGTC TGATTATCAA CGTGACCAAT CAATGTGGCA TGTTTTGCCG TCACTGTCAG
 541 CGTCGCCGCA ATATCGGCGA AGTGGACTAC CCGGCGAAAC ATGAAGATAT TGAAGCGGCG
 601 CTGGAATATA TCCGTAATAA TCCAGAGATC CGTGATGTTC TGATCACGGG CGGCGATCCA
 661 CTGACCCTGG AAGACGAAAA GATTGACTGG ATTCTGAGCG AACTGGATAA AATTCCGCAC
 721 GTGGAAATTA GCGCATCGG TACCGCGGCT CCAGTGACGT TCCCGCAACG TATTACCGAC
 781 GAACTGTGTA AAATTCTGAC GAAACATCTG CCGCTGTATA TCAACACACA ATTTAACCAT
 841 CCGAAAGAGG TTACCGAAGA GGCGAAAGAA GCCTGTTTTA AACTGGCGCG TGCGGGTGTG
 901 GCTCTGGGCA TCAGGCGGT ACTGCTGAAA GGCATCAATA ACGATCCACA TGTCATGAAG
 961 AAACTGAATC ATGAACTGCT GCGCATCATG GTCAAACCTT ATTATATTTT CCACGCGAAA
1021 TCTGTGCAAG GTACTACACA TTTTGTGACC ACCGTTCAGG ATGGCCTGGA ATTTATGGAG
1081 CAGCTGCGCG TTATACTAG TGGTCTGGCG ATCCCGTGGT ATATCATTAA CGCACCGGAA
1141 GGTCATGGTA AAACTCCGAT CGTTCCGCAG TACCTGCTGA TGGTAGGAAA GGAATACGTT
1201 CTGATCCGCA ATTGGGAAGG TAAAGTGTTT GAATATCCGA ACGGTTTCCC GGATGATTAA
```

*Desulfitobacterium hafniense* DCB-2
(SEQ ID NO: 29)

```
   1 ATGGCGATTG AATTTCTGCC GCCGAATCCG CGTCAGGCGA GCCAGGCGCG CGCGCTGGAA
  61 CTGAAACAGA AAGTGCAGAG CTATAATAAA CGTAAAGAAA CCATTCCGTG CGGCCTGGCG
 121 CTGAGCGAAG AATTTAACGA AAACCGTGAT TTTATTCTGG ATCAGCTGGA TGCGGATCTG
 181 GAACATTGGC AGGATTGGAA ATGGCAGCTG AAAAACCGCA TTCAGGATGC GGAAAATCTG
 241 AGCACCCTGC TGCCGCTGAC CCCGAAACAG CGCCATGAAA TTAATGAAGT GGGCAAAGCG
 301 TATCGTTGGG CGGTGAGCCC GTATTATCTG AGCCTGATTG ATAAAGATGA TCCGCAGGAT
 361 CCGATTCGCC TGCAGAGCCT GCCGAGCGTG GAAGAAATTC TGGATGATAG CGGTGAAGCG
 421 GATCCGATGG GCGAAGAATA TACCAGCCCG GCGCCGTGCA TTACCCGCCG CTATCCGGAT
 481 CGCCTGATTA TTAATGTTAC CAACCTGTGC GCGATGTATT GCCGTCATTG CCAGCGCCGC
 541 CGTAATATTG GCGAAATTGA TCTGCATGAA ACCCGTGCGA ACCTGGAAGC GGCGCTGGAT
 601 TATATTCGTA GCAACCCGGA AATTCGCGAT GTGCTGGTGA CCGGTGGCGA TGCGCTGCTG
 661 CTGAGCGATC AGATGCTGGA TTGGCTGCTG GGCGAACTGC ATGAAATTAA ACATGTGGAA
 721 ATTAAACGCA TTGGCACCCG TGTGCCGGTG ACCCTGCCGA TGCGCATTAC CGATGAACTG
 781 TGTGCGATTC TGGAAAAATA TCCGCCGCTG TATATTAACA CCCAGTTTAA CCATCCGCAG
 841 GAAGTGACCG AAGAACCAA AAAGCGGCG GATCGCCTGA TTAAAGCGGG CGTTATTCTG
 901 GGCAATCAGG CGGTTCTGCT GAAAGGCATT AACGATCAGC CGGAAATTAT GAACGTCTG
 961 AACCAGGAAC TGCTGAAAAT TCGTGTGCGC CCGTATTATA TTTTTCATGC GAAAAACGTG
1021 AAAGGCACCA GCCATTTTAT TCCGCGTATT CAGGATGGCC TGCGCATTAT GGAAAACCTG
```

-continued

```
1081 CGTGGTTATA CCAGCGGTCT GGCGATTCCG ACCTATATTA TTAACGCGCC GGGTGGTGGC

1141 GGCAAAACCC CGATTCTGCC GCAGTATCTG ATTAGCCTGA ACGATGAAGA AGCGGTGATT

1201 CGTACCTGGG AAGGCAAAGT GGTGCATTAT CCGAATCATT AA
```

Moorella thermoacetica (ATCC 39073)
(SEQ ID NO: 30)
```
   1 ATGGGTCGTG AAGCGAAACG CGAAATTGCG CTGGATCGTG CGGCGGAACT GAAAGCGCGT

61 ATTGTGGATT ATCTGGAAGA ACGTGAAAAA ATTGCGAGCG GCCTGGAAGC GGCCGCGGAA

121 ATCGAAGCCA GCAAACAGCG CATCCTGGCC TATTTTGGTG CGGGCGAAGC CGAATGGCAG

181 GATTGGCGTT GGCAGCTGAC CCATCGCATT ACCAGCGTGG CGACCCTGGC GGAACTGATT

241 CCGCTGACCG AAGCCGAAAA AGAAGCCATT CTGAAAGTTG AACGTACCTA TCGCTGGGCG

301 GTGAGCCCGT ATTATCTGAG CCTGATGGGC CCGGAACCGG ATTGTCCGAT CCGTCGTCAG

361 GCGCTGCCGA GCGCCGCGGA ACTGGAAGAT AACCATGGCG TGCTGGATCC GATGGATGAA

421 GAACTGACCA GCCCGGCGCC GGCCATTACC CGTCGTTATC CGGATCGCCT GATTATTAAC

481 GTGACCAACC AGTGTGCGAT GTATTGCCGC CATTGCCAGC GTCGCCGTAA TATCGGTGAA

541 GTGGATCGTA GCCGTAGCCG TCGTGAACTG AACAGGCCC TGCAGTATAT TCGTCAGAAT

601 GAAGAAATTC GTGATGTTCT GATTACCGGT GGTGATGCGC TGATGCTGAG CGATGCGATG

661 ATTGATTGGC TGCTGACCGA ACTGGATAAC ATTCCGCATG TTGAAATCAA CGCCTGGGT

721 ACCCGTGTGC CGGTGACCAT GCCGCAGCGT ATCACCCCGG AACTGTGCCG TGTTCTGGCC

781 AAACATCCGC CGATCTATCT GAATACCCAG TTTAATCATC CGCGCGAAGT TACCGCGGCG

841 GCGAAAGAAG CGTGTGATCG CCTGGTGCAG GCGGGCGTGG TTCTGGGTAA CCAGGCGGTT

901 CTGCTGAAAG CGTGAATAA CCATCCGTTT GTGATGCGTA AACTGAATCA GGAACTGCTG

961 AAAATCCGTG TTCGCCCGTA TTATATCTTT CATGCGAAAC CGGTGAAAGG CACCACCCAT

1021 TTCATTACCA GCATTGAAGA AGGTGTGGAA ATTATGGATA AACTGCGTGG CTATACCAGC

1081 GGTCTGGCGG TGCCGACCTA TCATTAAT GCGCCGCATG GTCTGGGCAA AACCCCGATC

1141 CTGCCGCAGT ATGTTATCGC GCGTAACGAT CACCAGGTGA TTCTGCGTAC CTGGGAAAAA

1201 CGCATTATCT TCTATAGCAA CCTGGGCCGC CAGAAAGAAC AGGCGTAA
```

Syntrophomonas wolfei (str. Goettingen)
(SEQ ID NO: 31)
```
   1 ATGCTGCTGC GCAAGATCT GATTAACGAA GAAATTCGCG AAATGAAACG CGAAGTGAGC

61 CTGCGTCGTG CGGATGAACT GAAACAGGAA ATTAGCGATT ATCTGGATAT TGAAAGCACC

121 ATTGAAACCG GTATGCGTCT GCATGAACGC AACCTGCATA ACAAAGAACA TATTCTGAAA

181 TATTTTGAAG TGAGCGAAAA CGATTGGGAT AACTGGGCGT GGCAGATGCG TAACCGTATT

241 AATGATGGTA ACGTGCTGGC GAGCATTCTG GGCCTGAATG AATTTGAAGT TCAGACCATT

301 AAACGTGTGA GCAAAAAAGT GCGTTGGGCG ATTAGCCCGT ATTATCTGAG CCTGATTGAT

361 TTTGAAAATT ATGCGGCGAG CCCGATTTAT AAACAGAGCG TGCCGAGCCT GCATGAAATT

421 ATTGAATGCA AAGGTGAAGA TGATCCGATG GGTGAAGAAA TGAGCAGCCC GGCGCCGCGT

481 ATTACCCGTC GTTATCCGGA TCGTCTGATT ATTAATGTTA CCAATCAGTG CGCGATGTAT

541 TGCCGCCATT GTCAGCGCCG CCGTAATTTT GGTGAAACCG ATAACCATGC GGCGCATAAA

601 GATCTGGAAG CGGCGCTGCA GTATATTAAA AATAATAGCG AAATTCGTGA TGTGCTGATT

661 ACCGGCGGTG ATGCGCTGAT GCTGAGCGAT CGCACCCTGG ATTGGCTGCT GGGTGAACTG

721 GATGCGATTA GCCATGTGGA AATTAAACGC ATTGGCACCC GTACCCCGGT GACCCTGCCG

781 CAGCGTATTA CCGCGAACCT GTGCGCGGTG CTGAAACGCC ATACCCCGAT TTATATTAAT
```

```
 841 ACCCAGTTTA ACAGCCCGCT GGAAGTGACC CCGGAAGCGA AACAGGCGTG CGATCGCCTG

901 ATTGAAGCGG GCGTGGTTCT GGGTAATCAG GCGGTGCTGC TGAAAGGCAT TAACGATAAC

961 GTGCATGTGA TGAAAAAACT GAATCAGGAA CTGCTGAAAA TTCGTGTGCG TCCGTATTAT

1021 CTGTTTCAGG CGAAAGAAGT GAAAGGCACC ACCCATTTTA TTAGCCCGGT TAACACCGGT

1081 CTGGATATTA TGAAACATCT GCGTGGTTAT ACCAGCGGCC TGGCGATTCC GACCTATGTT

1141 ATTAATGCGC CGGGTGGTTA TGGTAAAACC CCGGTGAATC CGGAATATGT GCTGGATATT

1201 AATGAAAATG AAGTGATTAT TAGCACCTGG CAGGGTAAAA CCTTTAACTA TCCGCATCGT

1261 AACAACTAA
``` pUC57 plasmids containing the synthetic genes were subjected to restriction digestion. For each gene insert, 10 μg of plasmid DNA was cut with NdeI (New England Biolabs, Beverly, Mass.)—20 units and XhoI (Promega Corp., Madison, Wis.)—10 units in a total volume of 100 μl for 1 hour. at 37° C. The insert DNA was separated from the plasmid DNA by agarose gel electrophoresis (2% agarose in TAE buffer). Following identification and excision of the appropriately sized ethidium bromide stained band (approximately 1200 bp), DNA was extracted from the agarose using the GenElute Minus EtBr spin column (Sigma #5-6501, St. Louis, Mo.), concentrated by precipitation with ethanol, and resuspended in TE buffer at pH 8.0. The expression vector, pET21a(+) (Novagen, Madison, Wis.) was similarly cut with NdeI and XhoI, dephosphorylated at the 5' end with calf-intestine alkaline phosphatase (Promega Corp.)—1 unit for 30 min. at 37° C., purified by agarose gel electrophoresis, and concentrated by ethanol precipitation (as previously described). The pET-21a(+) insert and the pET-21a(+) cut vector were ligated with T4 DNA ligase. To 3 ng of insert DNA were added 10 ng of cut vector in T4 DNA ligase buffer (Promega Corp.)+T4 DNA ligase (Promega Corp.)—3 units in a total volume of 10 μl and incubated for 16 hours. at 14° C. Competent E. coli (Epicurian coli XL2-Blue MRF', Stratagene) were transformed with 2 μl ligation mix and plated on LB+carbenicillin (Sigma #C1389) (100 μg/ml) plates and cultured overnight. Individual colonies were chosen and subcloned in LB+carbenicillin (100 μg/ml) media for plasmid purification. Plasmid DNA was purified using Qiagen Plasmid mini kit (Qiagen, Inc., Santa Clarita, Calif.). The pET21a(+) synthetic gene inserts were sequenced in entirety including both regions of the start and stop codon to confirm the correctness of the constructs. The pET21a(+) gene insert expression vectors and pET21a(+) vector without recombinant gene (Control) were transformed into competent E.coli BL21(DE3) (Gold) cells (Stratagene, La Jolla, Calif.). 100 μl of competent cells were treated with 25 ng of plasmid DNA. Cells were heat shocked for 20 sec. at 42° C. After transformation, 10 μl of cells were plated on LB+carbenicillin (100 μg/ml) plates and grown overnight at 37° C. Individual colonies were subcultured in LB media containing carbenicillin (100 μg/ml) to prepare frozen stocks.

For protein expression, cells from frozen stocks were subsequently used to streak LB plates containing carbenicillin (100 μg/ml). Individual colonies were selected, grown in LB media containing carbenicillin (100 μg/ml) for approximately 6 hours at 37° C., and used to inoculate 2 liter shake flasks each containing 1 liter of LB medium with ampicillin (Fisher #BP1760-25) (100 μg/ml) and supplemented with 100 μM $FeCl_3$. Cells were cultured overnight (16 hours) at 37° C. with slow shaking (100 RPM). After 16 hours IPTG (Inalco, San Louis Obispo, Calif. #1758-1400) was added to a concentration of 1 mM, and culturing was continued for an additional 4 hours at 37° C. prior to harvesting by centrifugation. Cells were harvested by centrifugation at 6,000×$g_{av}$ for 10 min., and small portions were frozen in liquid nitrogen and stored at −70° C. until used for enzyme purification. Approximately 40 grams (wet weight) of cells were harvested from 10 liters of growth medium.

For preparation of cell extracts, all steps except centrifugation were conducted in an anaerobic chamber (Coy, Grass Lake, Mich.) at room temperature. To prevent oxygen contamination, liquid suspensions were sealed into centrifuge bottles inside the anaerobic chamber before centrifugation at 4° C. outside the chamber. Cells were thawed in 50 ml standard buffer (SB) [0.03 M sodium EPPS (Sigma #E9502) at pH 8.0, 40 μM $FeSO_4$ (J T Baker #2070-1), 40 μM pyridoxal-5'-phosphate (Sigma #P9255), 1 mM DTT (Inalco #1758-9030), and 1 mM PMSF (Sigma #P7626)] prior to sonication using the standard tip of the Sonic Dismembrator (Misonix, Farmingdale, N.Y., Model #3000) (setting 8 for six 30 sec. intervals at 4-8° C.). Following sonication, cells were centrifuged at 20,000×$g_{av}$ for 30 min. The supernatant fluids of each cell extract were snap frozen in liquid nitrogen and stored in liquid nitrogen until used for enzyme assay.

Glutamate 2,3-aminomutase Activity Measurements of Cell Extracts. Enzyme assays for cell extracts of homologous glutamate 2,3-aminomutase proteins were conducted in an anaerobic chamber (Coy, Grass Lake, Mich.) at 37° C. or 65° C. Cell extracts were mixed with the following components: A) EPPS, 60 mM pH 8.0, Na salt; B) S-(5'-adenosyl)-L-methionine (Sigma) 150 μM; sodium hydrosulfite (Sigma #G-1251) 200 μM; C) L-glutamate (Sigma #G1251) 50 mM. At various time intervals (0-15 min), 35 μl of reaction mix was added to 15 μl of 2 N perchloric acid to stop the reaction. Samples were centrifuged at 14,000×g for 10 min. The supernatant fluids were treated with PITC and subjected to HPLC analysis as described in Example 2.

Glutamate 2,3-aminomutase activity was measured in extracts of E. coli cells containing plasmid expression vectors with homologous recombinant genes from Desulfitobacterium hafniense, eSyntrophomonas wolfei, Thermoanaerobacter tengcongensis, and Moorella thermoacetica (Table 4). No glutamate 2,3-aminomutase activity was measured in E. coli cell extracts containing the pET21a(+) expression vector without the above recombinant genes. Therefore the above homologous genes code for glutamate 2,3-aminomutase proteins. The different activities measured are a reflection of the kinetic properties and the amount of protein expression of each enzyme in the cell extracts.

TABLE 4

E. coli plasmid vector-based expression of homologous glutamate 2,3-aminomutase genes. Glutamate 2,3-aminomutase activity in E. coli cell extracts.

| Bacterial source | Specific Acitivity nmoles β-Glu min$^{-1}$ mg$^{-1}$ Protein |
|---|---|
| *Desulfitobacterium hafniense* | 2.5* |
| *Syntrophomonas wolfei* | 0.62* |
| *Thermoanaerobacter tengcongensis* | 31.4+ |
| *Moorella thermoacetica* | 18.5+ |
| Control (Plasmid without gene) | 0 |

*Assay temperature - 37 deg C.
+Assay temperature - 65 deg C.

REFERENCES

1. Frey, P. A. (2001) Ann. Rev. Biochem. 70, 121-148.
2. Chen, D., Ruzicka, F. J. and Frey, P. A. (2000) Biochem. J. 348, 539-549.
3. Prabhakaran, P. C., Woo, N-T., Yorgey, P. S. and Gould, S. J. (1988) J. Am. Chem. Soc. 110, 5785-5791.
4. Poston, J. M. (1980) J. Biol. Chem. 255, 10067-10072.
5. Steele, C. L., Chen. Y., Dougherty, B. A., Hofstead, S., Lam, K. S., Li, W., and Xing, Z. (2003) U.S. Patent AN 2003:633941.
6. Walker, K. D., Klettke, K., Akiyama, T., and Croteau, R. (2004) J. Biol. Chem. 279, 53947-53954.
7. Christenson, S. D., Liu, W., Toney, M. D., and Shen, B. (2003) J. Am. Chem. Soc. 125, 6062-6063.
8. Jackowski, S. (1982) J. Bacteriol. 149, 916-922.
9. Moss, M. and Frey, P. A. (1987) J. Biol. Chem. 262, 14859-14862.
10. Frey, P. A. and Magnusson, O. Th. (2003 Chem. Rev. 103, 2129-2148.
11. Lieder, K. W., Booker, S., Ruzicka, F. J., Beinert, H., Reed, G. H., and Frey, P. A. (1998) Biochemistry 37, 2578-2585.
12. Lepore, B. W., Ruzicka, F. J., Frey, P. A. and Ringe, D. (2005) Proc. Natl. Acad. Sci. USA in press.
13. Ballinger, M. D., Frey, P. A. and Reed, G. A. (1992) Biochemistry 31, 10782-10789.
14. Magnusson, O. Th., Reed, G. H. and Frey, P. A. (2001) Biochemistry 40, 7773-7782.
15. Chen, D., Walsby, C. J., Hoffman, B. M. and Frey, P. A. (2003) J. Am. Chem. Soc. 125, 1178-11789.
16. Ballinger, M. D., Frey, P. A. and Reed, G. A. (1995) Biochemistry 34, 1008610093.
17. Cosper, N. J., Booker, S. J., Ruzicka, F. J., Frey, P. A., and Scott, R. A. (2000) Biochemistry 39, 15668-15673.
18. Robertson, D. E., Noll, D. And Roberts, M. F. (1992) J. Biol. Chem. 267, 14893-14901.
19. Sowers, K., Robertson, D. E., Noll, D., Gunsalus, R. P., and Roberts, M. F. (1990) Proc. Natl. Acad. Sci. USA 87, 9083-9087.
20. Heinrikson, R. L. and Meredith, S. C. (1984) Anal. Biochem. 136, 65-74.
21. Kennedy, M. C., Kent, T. A., Emptage, M., Merkle, H., Beinert, H., and Munck, E. (1984) J. Biol. Chem. 259, 14463-14471.
22. Beinert, H. (1983) Anal. Biochem. 131, 373-378.
23. Wada, H. And Snell, E. E. (1961) J. Biol. Chem. 236, 2089-2095.
24. Laemmli, U. K. (1970) 227, 680-682.
25. Cleland, W. W. (1979) Methods Enzymol. 63, 102-138.
26. Ozols, J. (1990) Meth. Enzymol. 182, 587-600.
27. Petrovich, R. M., Ruzicka, F. J., Reed, G. H., and Frey, P. A. (1992) Biochemistry 31, 10774-10781.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. An isolated DNA molecule encoding a polypeptide having glutamate 2,3-aminomutase activity, wherein the DNA molecule comprises a sequence selected from the group consisting of
   a) a DNA sequence encoding a polypeptide having at least 80% sequence identity to the amino acid sequence of SEQ ID NO: 2, wherein the polypeptide comprises the following amino acid sequences: CXXXCRXCXR (SEQ ID NO: 19), S/(T)GGE/(D) (SEQ ID NO: 20), GXXXPXXXXXXXXXXXK (SEQ ID NO: 21), PXYXXXXKXXXG (SEQ ID NO: 22), and PXXXX-NXXXXXXK (SEQ ID NO: 23);
   b) a DNA sequence comprising SEQ ID NO: 1; and
   c) a DNA sequence which is degenerate to the sequence of (b) due to the genetic code.

2. An expression vector comprising the DNA molecule of claim 1.

3. The expression vector of claim 2 wherein the DNA molecule is operably linked to one or more control sequences which direct the production of the polypeptide in a host cell.

4. A recombinant host cell comprising the DNA molecule of claim 1.

5. A recombinant host cell comprising the expression vector of claim 2.

6. The recombinant host cell of claim 5 wherein the recombinant host cell is a prokaryotic cell.

7. The recombinant host cell of claim 6 wherein the cell is a bacterial cell.

8. The recombinant host cell of claim 6 wherein the cell is an *E. coli* cell.

9. A method of producing a polypeptide having glutamate 2,3-aminomutase activity comprising culturing the recombinant host cell of claim 6.

10. The method of claim 9 further comprising isolating the polypeptide produced from the recombinant host cell.

11. The isolated DNA molecule of claim 1 wherein the DNA sequence encoding the polypeptide has at least 95% sequence identity to the amino acid sequence of SEQ ID NO: 2.

12. An isolated DNA molecule encoding a polypeptide having glutamate 2,3-aminomutase activity, wherein the DNA molecule comprises a sequence encoding a polypeptide having at least 95% sequence identity to the amino acid sequence of SEQ ID NO: 2.

13. A recombinant host cell comprising the DNA molecule of claim 12.

14. An expression vector comprising the DNA molecule of claim 12.

15. The expression vector of claim 14 wherein the DNA molecule is operably linked to one or more control sequences which direct the production of the polypeptide in a host cell.

16. A recombinant host cell comprising the expression vector of claim 15.

17. The recombinant host cell of claim 16 wherein the recombinant host cell is a prokaryotic cell.

18. The recombinant host cell of claim 17 wherein the cell is a bacterial cell.

19. The recombinant host cell of claim 18 wherein the cell is an *E. coli* cell.

20. A method of producing a polypeptide having glutamate 2,3-aminomutase activity comprising culturing the recombinant host cell of claim 16.

21. The method of claim 20 further comprising isolating the polypeptide produced from the recombinant host cell.

* * * * *